(12) United States Patent
Wagner et al.

(10) Patent No.: US 10,723,796 B2
(45) Date of Patent: Jul. 28, 2020

(54) T CELL RECEPTORS AND IMMUNE THERAPY USING THE SAME

(71) Applicant: Immatics Biotechnologies GmbH, Tuebingen (DE)

(72) Inventors: Claudia Wagner, Tuebingen (DE); Leonie Alten, Tuebingen (DE); Sebastian Bunk, Tuebingen (DE); Dominik Maurer, Moessingen (DE)

(73) Assignee: IMMATICS BIOTECHNOLOGIES GMBH, Tuebingen (DE)

( * ) Notice: Subject to any disclaimer, the term of this patent is extended or adjusted under 35 U.S.C. 154(b) by 0 days.

(21) Appl. No.: 16/403,269

(22) Filed: May 3, 2019

(65) Prior Publication Data

US 2019/0256590 A1  Aug. 22, 2019

Related U.S. Application Data

(63) Continuation of application No. 16/023,731, filed on Jun. 29, 2018.

(60) Provisional application No. 62/527,844, filed on Jun. 30, 2017.

(30) Foreign Application Priority Data

Jun. 30, 2017 (DE) .................. 10 2017 114 737

(51) Int. Cl.
| | | |
|---|---|---|
| C07K 16/38 | (2006.01) | |
| C07K 14/725 | (2006.01) | |
| C07K 16/26 | (2006.01) | |
| C07K 14/81 | (2006.01) | |
| C07K 16/28 | (2006.01) | |
| C12N 5/0783 | (2010.01) | |
| C12N 15/85 | (2006.01) | |

(52) U.S. Cl.
CPC .......... *C07K 16/26* (2013.01); *C07K 14/7051* (2013.01); *C07K 14/8135* (2013.01); *C07K 16/2833* (2013.01); *C07K 16/38* (2013.01); *C12N 5/0636* (2013.01); *C12N 15/85* (2013.01); *C07K 2317/30* (2013.01); *C07K 2317/32* (2013.01); *C07K 2317/565* (2013.01); *C07K 2317/62* (2013.01); *C12N 2015/8518* (2013.01)

(58) Field of Classification Search
None
See application file for complete search history.

(56) References Cited

U.S. PATENT DOCUMENTS

| | | | |
|---|---|---|---|
| 10,004,792 B2 | 6/2018 | Mahr et al. | |
| 10,058,598 B2 | 8/2018 | Mahr et al. | |
| 10,098,937 B2 | 10/2018 | Mahr et al. | |
| 10,098,938 B2 | 10/2018 | Mahr et al. | |
| 10,117,917 B2 | 11/2018 | Mahr et al. | |
| 10,143,730 B2 | 12/2018 | Mahr et al. | |
| 10,143,731 B2 | 12/2018 | Mahr et al. | |
| 10,179,165 B2 | 1/2019 | Mahr et al. | |
| 2016/0152681 A1* | 6/2016 | Hinrichs ............ | C07K 14/7051 424/93.71 |
| 2016/0159880 A1* | 6/2016 | Giulianotti ............. | C07K 16/00 435/69.1 |
| 2017/0165338 A1 | 6/2017 | Mahr et al. | |
| 2017/0189504 A1 | 7/2017 | Mahr et al. | |
| 2017/0189507 A1 | 7/2017 | Mahr et al. | |
| 2017/0189512 A1 | 7/2017 | Mahr et al. | |
| 2018/0360936 A1 | 12/2018 | Mahr et al. | |
| 2018/0360937 A1 | 12/2018 | Mahr et al. | |
| 2019/0015492 A1 | 1/2019 | Mahr et al. | |

FOREIGN PATENT DOCUMENTS

| | | |
|---|---|---|
| WO | 2017/064198 A1 | 4/2017 |
| WO | 2017/089765 A1 | 6/2017 |
| WO | 2017/089781 A2 | 6/2017 |
| WO | 2017/097699 A1 | 6/2017 |

OTHER PUBLICATIONS

Janeway et al., Immunobiology, 5th Ed., Garland Science, pp. 106-108 and 260-263, (2001) (Year: 2001).*
Manning et al., Immunity, vol. 8, 413-425, Apr. 1998. (Year: 1998).*
Piepenbrink et al., Nature, 2013; 4:1948. (Year: 2013).*
Garcia et al., Cell, vol. 122, 333-336, Aug. 12, 2005. (Year: 2005).*
Portolano et al., J Immunol. Feb. 1, 1993;150(3):880-7. (Year: 1993).*
Goyarts et al. (Mol Immunol. Jul. 1998;35(10):593-607). (Year: 1998).*
Peters et al., Arch Pathol Lab Med. 2011;135:44-54. (Year: 2011).*
Brown et al., Leukemia Research 36 (2012) 14-22. (Year: 2012).*
Chen et al. (Proteins 2009; 77:209-219). (Year: 2009).*
Popovic et al. (Blood. 2011; 118(4):946-954). (Year: 2011).*
Sandberg et al., Proc Natl Acad Sci USA. Feb. 8, 2005;102(6):2052-7. (Year: 2005).*

(Continued)

*Primary Examiner* — Zachary S Skelding
(74) *Attorney, Agent, or Firm* — McBee Moore & Vanik IP, LLC

(57) ABSTRACT

The present invention pertains to antigen recognizing constructs against tumor associated antigens (TAA), in particular the TAA Serine protease inhibitor Kazal-type 2 (SPINK2). The invention in particular provides novel T cell receptor (TCR) based molecules which are selective and specific for the tumor expressed antigen of the invention. The TCR of the invention, and SPINK2 binding fragments derived therefrom, are of use for the diagnosis, treatment and prevention of SPINK2 expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

20 Claims, 33 Drawing Sheets
(12 of 33 Drawing Sheet(s) Filed in Color)
Specification includes a Sequence Listing.

(56) References Cited

OTHER PUBLICATIONS

Marie-Paule Lefranc, Methods Mol Biol. 2014;1184:59-107. (Year: 2014).*
Search Report for German Application 10 2017 114 737.3, dated Mar. 21, 2018.
Chen, et al., "serine protease inhibitor Kazal-type 2 isoform 1 precursor [*Homo sapiens*]," NCBI Reference Sequence: NP_001258647.1, Mar. 20, 2018, www.ncbi.nlm.nih.gov/proteinNP_001258647.
Tiller, et al., "Advances in Antibody Design," Annual Review of Biomedical Engineering, (2015), vol. 17: 191-216.
Hoefnagel, Juliette J. et al., "Distinct types of primary cutaneous large B-cell lymphoma identified by gene expression profiling", Blood, May 1, 2005, pp. 3671-3678, vol. 105, No. 9.

* cited by examiner

SEQUENCE LISTING

```
<160> NUMBER OF SEQ ID NOS: 159

<210> SEQ ID NO 1
<211> LENGTH: 6
<212> TYPE: PRT
<213> ORGANISM: Homo sapiens
```

```
<400> SEQUENCE: 1

Asp Ser Ser Ser Thr Tyr
1               5

<210> SEQ ID NO 2
<211> LENGTH: 3
<212> TYPE: PRT
<213> ORGANISM: Homo sapiens

<400> SEQUENCE: 2

Ile Phe Ser
1

<210> SEQ ID NO 3
<211> LENGTH: 13
<212> TYPE: PRT
<213> ORGANISM: Homo sapiens

<400> SEQUENCE: 3

Cys Ala Glu Ile Asp Asn Gln Gly Gly Lys Leu Ile Phe
1               5                  10

<210> SEQ ID NO 4
<211> LENGTH: 132
<212> TYPE: PRT
<213> ORGANISM: Homo sapiens

<400> SEQUENCE: 4

Met Lys Thr Phe Ala Gly Phe Ser Phe Leu Phe Leu Trp Leu Gln Leu
1               5                  10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
                100                 105                 110

Ile Asp Asn Gln Gly Gly Lys Leu Ile Phe Gly Gln Gly Thr Glu Leu
            115                 120                 125

Ser Val Lys Pro
        130

<210> SEQ ID NO 5
<211> LENGTH: 141
<212> TYPE: PRT
<213> ORGANISM: Homo sapiens

<400> SEQUENCE: 5

Asn Ile Gln Asn Pro Asp Pro Ala Val Tyr Gln Leu Arg Asp Ser Lys
1               5                  10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45
```

Val Leu Asp Met Arg Ser Met Asp Phe Lys Ser Asn Ser Ala Val Ala
            50                  55                  60

Trp Ser Asn Lys Ser Asp Phe Ala Cys Ala Asn Ala Phe Asn Asn Ser
 65                  70                  75                  80

Ile Ile Pro Glu Asp Thr Phe Phe Pro Ser Pro Glu Ser Ser Cys Asp
                    85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Leu Lys Val Ala
                115                 120                 125

Gly Phe Asn Leu Leu Met Thr Leu Arg Leu Trp Ser Ser
130                 135                 140

<210> SEQ ID NO 6
<211> LENGTH: 273
<212> TYPE: PRT
<213> ORGANISM: Homo sapiens

<400> SEQUENCE: 6

Met Lys Thr Phe Ala Gly Phe Ser Phe Leu Phe Leu Trp Leu Gln Leu
 1                   5                  10                  15

Asp Cys Met Ser Arg Gly Glu Asp Val Glu Gln Ser Leu Phe Leu Ser
                    20                  25                  30

Val Arg Glu Gly Asp Ser Ser Val Ile Asn Cys Thr Tyr Thr Asp Ser
                35                  40                  45

Ser Ser Thr Tyr Leu Tyr Trp Tyr Lys Gln Glu Pro Gly Ala Gly Leu
 50                  55                  60

Gln Leu Leu Thr Tyr Ile Phe Ser Asn Met Asp Met Lys Gln Asp Gln
 65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
                100                 105                 110

Ile Asp Asn Gln Gly Gly Lys Leu Ile Phe Gly Gln Gly Thr Glu Leu
                115                 120                 125

Ser Val Lys Pro Asn Ile Gln Asn Pro Asp Pro Ala Val Tyr Gln Leu
130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
                180                 185                 190

Ser Ala Val Ala Trp Ser Asn Lys Ser Asp Phe Ala Cys Ala Asn Ala
                195                 200                 205

Phe Asn Asn Ser Ile Ile Pro Glu Asp Thr Phe Phe Pro Ser Pro Glu
                210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
                260                 265                 270

Ser

<210> SEQ ID NO 7
<211> LENGTH: 5
<212> TYPE: PRT
<213> ORGANISM: Homo sapiens

<400> SEQUENCE: 7

Ser Gly His Asp Thr
1               5

<210> SEQ ID NO 8
<211> LENGTH: 6
<212> TYPE: PRT
<213> ORGANISM: Homo sapiens

<400> SEQUENCE: 8

Tyr Tyr Glu Glu Glu Glu
1               5

<210> SEQ ID NO 9
<211> LENGTH: 12
<212> TYPE: PRT
<213> ORGANISM: Homo sapiens

<400> SEQUENCE: 9

Cys Ala Ser Ser Gln Leu Asn Thr Glu Ala Phe Phe
1               5                   10

<210> SEQ ID NO 10
<211> LENGTH: 130
<212> TYPE: PRT
<213> ORGANISM: Homo sapiens

<400> SEQUENCE: 10

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Gln Leu Asn Thr Glu Ala Phe Phe Gly Gln Gly Thr Arg Leu Thr
        115                 120                 125

Val Val
    130

<210> SEQ ID NO 11
<211> LENGTH: 177
<212> TYPE: PRT
<213> ORGANISM: Homo sapiens

<400> SEQUENCE: 11

Glu Asp Leu Asn Lys Val Phe Pro Pro Glu Val Ala Val Phe Glu Pro
1               5                   10                  15

```
Ser Glu Ala Glu Ile Ser His Thr Gln Lys Ala Thr Leu Val Cys Leu
            20                  25                  30

Ala Thr Gly Phe Phe Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Val Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Phe

<210> SEQ ID NO 12
<211> LENGTH: 307
<212> TYPE: PRT
<213> ORGANISM: Homo sapiens

<400> SEQUENCE: 12

Met Gly Pro Gly Leu Leu Cys Trp Ala Leu Leu Cys Leu Leu Gly Ala
1               5                   10                  15

Gly Leu Val Asp Ala Gly Val Thr Gln Ser Pro Thr His Leu Ile Lys
            20                  25                  30

Thr Arg Gly Gln Gln Val Thr Leu Arg Cys Ser Pro Lys Ser Gly His
        35                  40                  45

Asp Thr Val Ser Trp Tyr Gln Gln Ala Leu Gly Gln Gly Pro Gln Phe
    50                  55                  60

Ile Phe Gln Tyr Tyr Glu Glu Glu Arg Gln Arg Gly Asn Phe Pro
65                  70                  75                  80

Asp Arg Phe Ser Gly His Gln Phe Pro Asn Tyr Ser Ser Glu Leu Asn
                85                  90                  95

Val Asn Ala Leu Leu Leu Gly Asp Ser Ala Leu Tyr Leu Cys Ala Ser
            100                 105                 110

Ser Gln Leu Asn Thr Glu Ala Phe Phe Gly Gln Gly Thr Arg Leu Thr
        115                 120                 125

Val Val Glu Asp Leu Asn Lys Val Phe Pro Pro Glu Val Ala Val Phe
    130                 135                 140

Glu Pro Ser Glu Ala Glu Ile Ser His Thr Gln Lys Ala Thr Leu Val
145                 150                 155                 160

Cys Leu Ala Thr Gly Phe Phe Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205
```

```
Arg Leu Arg Val Ser Ala Thr Phe Trp Gln Asn Pro Arg Asn His Phe
        210                 215                 220
Arg Cys Gln Val Gln Phe Tyr Gly Leu Ser Glu Asn Asp Glu Trp Thr
225                 230                 235                 240
Gln Asp Arg Ala Lys Pro Val Thr Gln Ile Val Ser Glu Ala Trp
            245                 250                 255
Gly Arg Ala Asp Cys Gly Phe Thr Ser Val Ser Tyr Gln Gln Gly Val
                260                 265                 270
Leu Ser Ala Thr Ile Leu Tyr Glu Ile Leu Leu Gly Lys Ala Thr Leu
        275                 280                 285
Tyr Ala Val Leu Val Ser Ala Leu Val Leu Met Ala Met Val Lys Arg
    290                 295                 300
Lys Asp Phe
305

<210> SEQ ID NO 13
<211> LENGTH: 6
<212> TYPE: PRT
<213> ORGANISM: Homo sapiens

<400> SEQUENCE: 13

Asp Arg Gly Ser Gln Ser
1               5

<210> SEQ ID NO 14
<211> LENGTH: 2
<212> TYPE: PRT
<213> ORGANISM: Homo sapiens

<400> SEQUENCE: 14

Ile Tyr
1

<210> SEQ ID NO 15
<211> LENGTH: 10
<212> TYPE: PRT
<213> ORGANISM: Homo sapiens

<400> SEQUENCE: 15

Cys Ala Val Asn Asn Ala Arg Leu Met Phe
1               5                   10

<210> SEQ ID NO 16
<211> LENGTH: 129
<212> TYPE: PRT
<213> ORGANISM: Homo sapiens

<400> SEQUENCE: 16

Met Lys Ser Leu Arg Val Leu Leu Val Ile Leu Trp Leu Gln Leu Ser
1               5                   10                  15
Trp Val Trp Ser Gln Gln Lys Glu Val Glu Gln Asn Ser Gly Pro Leu
                20                  25                  30
Ser Val Pro Glu Gly Ala Ile Ala Ser Leu Asn Cys Thr Tyr Ser Asp
            35                  40                  45
Arg Gly Ser Gln Ser Phe Phe Trp Tyr Arg Gln Tyr Ser Gly Lys Ser
        50                  55                  60
Pro Glu Leu Ile Met Phe Ile Tyr Ser Asn Gly Asp Lys Glu Asp Gly
65                  70                  75                  80
Arg Phe Thr Ala Gln Leu Asn Lys Ala Ser Gln Tyr Val Ser Leu Leu
```

```
            85                  90                  95

Ile Arg Asp Ser Gln Pro Ser Asp Ser Ala Thr Tyr Leu Cys Ala Val
            100                 105                 110

Asn Asn Ala Arg Leu Met Phe Gly Asp Gly Thr Gln Leu Val Val Lys
            115                 120                 125

Pro

<210> SEQ ID NO 17
<211> LENGTH: 141
<212> TYPE: PRT
<213> ORGANISM: Homo sapiens

<400> SEQUENCE: 17

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140

<210> SEQ ID NO 18
<211> LENGTH: 270
<212> TYPE: PRT
<213> ORGANISM: Homo sapiens

<400> SEQUENCE: 18

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Asn Ala Arg Leu Met Phe Gly Asp Gly Thr Gln Leu Val Val Lys
            115                 120                 125

Pro Asn Ile Gln Asn Pro Asp Pro Ala Val Tyr Gln Leu Arg Asp Ser
            130                 135                 140
```

```
Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 19
<211> LENGTH: 5
<212> TYPE: PRT
<213> ORGANISM: Homo sapiens

<400> SEQUENCE: 19

Ser Asn His Leu Tyr
1               5

<210> SEQ ID NO 20
<211> LENGTH: 6
<212> TYPE: PRT
<213> ORGANISM: Homo sapiens

<400> SEQUENCE: 20

Phe Tyr Asn Asn Glu Ile
1               5

<210> SEQ ID NO 21
<211> LENGTH: 13
<212> TYPE: PRT
<213> ORGANISM: Homo sapiens

<400> SEQUENCE: 21

Cys Ala Ser Ser Gly Gln Gly Ala Asn Glu Gln Tyr Phe
1               5                   10

<210> SEQ ID NO 22
<211> LENGTH: 132
<212> TYPE: PRT
<213> ORGANISM: Homo sapiens

<400> SEQUENCE: 22

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
```

```
            65                  70                  75                  80

Asp Asp Gln Phe Ser Val Glu Arg Pro Asp Gly Ser Asn Phe Thr Leu
                    85                  90                  95

Lys Ile Arg Ser Thr Lys Leu Glu Asp Ser Ala Met Tyr Phe Cys Ala
                100                 105                 110

Ser Ser Gly Gln Gly Ala Asn Glu Gln Tyr Phe Gly Pro Gly Thr Arg
                115                 120                 125

Leu Thr Val Thr
        130

<210> SEQ ID NO 23
<211> LENGTH: 179
<212> TYPE: PRT
<213> ORGANISM: Homo sapiens

<400> SEQUENCE: 23

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 24
<211> LENGTH: 311
<212> TYPE: PRT
<213> ORGANISM: Homo sapiens

<400> SEQUENCE: 24

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80
```

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gly Gln Gly Ala Asn Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 25
<211> LENGTH: 7
<212> TYPE: PRT
<213> ORGANISM: Homo sapiens

<400> SEQUENCE: 25

Thr Ser Glu Ser Asp Tyr Tyr
1               5

<210> SEQ ID NO 26
<211> LENGTH: 4
<212> TYPE: PRT
<213> ORGANISM: Homo sapiens

<400> SEQUENCE: 26

Gln Glu Ala Tyr
1

<210> SEQ ID NO 27
<211> LENGTH: 10
<212> TYPE: PRT
<213> ORGANISM: Homo sapiens

<400> SEQUENCE: 27

Cys Ala Tyr Leu Asn Tyr Gln Leu Ile Trp
1               5                   10

<210> SEQ ID NO 28
<211> LENGTH: 131
<212> TYPE: PRT
<213> ORGANISM: Homo sapiens

<400> SEQUENCE: 28

Met Ala Cys Pro Gly Phe Leu Trp Ala Leu Val Ile Ser Thr Cys Leu
1               5                   10                  15

Glu Phe Ser Met Ala Gln Thr Val Thr Gln Ser Gln Pro Glu Met Ser
            20                  25                  30

Val Gln Glu Ala Glu Thr Val Thr Leu Ser Cys Thr Tyr Asp Thr Ser
        35                  40                  45

Glu Ser Asp Tyr Tyr Leu Phe Trp Tyr Lys Gln Pro Pro Ser Arg Gln
    50                  55                  60

Met Ile Leu Val Ile Arg Gln Glu Ala Tyr Lys Gln Asn Ala Thr
65                  70                  75                  80

Glu Asn Arg Phe Ser Val Asn Phe Gln Lys Ala Ala Lys Ser Phe Ser
                85                  90                  95

Leu Lys Ile Ser Asp Ser Gln Leu Gly Asp Ala Ala Met Tyr Phe Cys
            100                 105                 110

Ala Tyr Leu Asn Tyr Gln Leu Ile Trp Gly Ala Gly Thr Lys Leu Ile
        115                 120                 125

Ile Lys Pro
    130

<210> SEQ ID NO 29
<211> LENGTH: 141
<212> TYPE: PRT
<213> ORGANISM: Homo sapiens

<400> SEQUENCE: 29

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 30
<211> LENGTH: 272
<212> TYPE: PRT
<213> ORGANISM: Homo sapiens

<400> SEQUENCE: 30

Met Ala Cys Pro Gly Phe Leu Trp Ala Leu Val Ile Ser Thr Cys Leu

```
            1               5                   10                  15
        Glu Phe Ser Met Ala Gln Thr Val Thr Gln Ser Gln Pro Glu Met Ser
                        20                  25                  30

Val Gln Glu Ala Glu Thr Val Thr Leu Ser Cys Thr Tyr Asp Thr Ser
                        35                  40                  45

Glu Ser Asp Tyr Tyr Leu Phe Trp Tyr Lys Gln Pro Pro Ser Arg Gln
                        50                  55                  60

Met Ile Leu Val Ile Arg Gln Glu Ala Tyr Lys Gln Gln Asn Ala Thr
         65                  70                  75                  80

Glu Asn Arg Phe Ser Val Asn Phe Gln Lys Ala Ala Lys Ser Phe Ser
                        85                  90                  95

Leu Lys Ile Ser Asp Ser Gln Leu Gly Asp Ala Ala Met Tyr Phe Cys
                        100                 105                 110

Ala Tyr Leu Asn Tyr Gln Leu Ile Trp Gly Ala Gly Thr Lys Leu Ile
                        115                 120                 125

Ile Lys Pro Asp Ile Gln Asn Pro Asp Pro Ala Val Tyr Gln Leu Arg
                        130                 135                 140

Asp Ser Lys Ser Ser Asp Lys Ser Val Cys Leu Phe Thr Asp Phe Asp
        145                 150                 155                 160

Ser Gln Thr Asn Val Ser Gln Ser Lys Asp Ser Asp Val Tyr Ile Thr
                        165                 170                 175

Asp Lys Thr Val Leu Asp Met Arg Ser Met Asp Phe Lys Ser Asn Ser
                        180                 185                 190

Ala Val Ala Trp Ser Asn Lys Ser Asp Phe Ala Cys Ala Asn Ala Phe
                        195                 200                 205

Asn Asn Ser Ile Ile Pro Glu Asp Thr Phe Phe Pro Ser Pro Glu Ser
                        210                 215                 220

Ser Cys Asp Val Lys Leu Val Glu Lys Ser Phe Glu Thr Asp Thr Asn
        225                 230                 235                 240

Leu Asn Phe Gln Asn Leu Ser Val Ile Gly Phe Arg Ile Leu Leu Leu
                        245                 250                 255

Lys Val Ala Gly Phe Asn Leu Leu Met Thr Leu Arg Leu Trp Ser Ser
                        260                 265                 270

<210> SEQ ID NO 31
<211> LENGTH: 5
<212> TYPE: PRT
<213> ORGANISM: Homo sapiens

<400> SEQUENCE: 31

Ser Asn His Leu Tyr
1               5

<210> SEQ ID NO 32
<211> LENGTH: 6
<212> TYPE: PRT
<213> ORGANISM: Homo sapiens

<400> SEQUENCE: 32

Phe Tyr Asn Asn Glu Ile
1               5

<210> SEQ ID NO 33
<211> LENGTH: 13
<212> TYPE: PRT
<213> ORGANISM: Homo sapiens

<400> SEQUENCE: 33
```

```
Cys Ala Ser Ser Glu Met Thr Ala Val Gly Gln Tyr Phe
1               5                  10

<210> SEQ ID NO 34
<211> LENGTH: 132
<212> TYPE: PRT
<213> ORGANISM: Homo sapiens

<400> SEQUENCE: 34

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Met Thr Ala Val Gly Gln Tyr Phe Gly Pro Gly Thr Arg
        115                 120                 125

Leu Thr Val Thr
    130

<210> SEQ ID NO 35
<211> LENGTH: 179
<212> TYPE: PRT
<213> ORGANISM: Homo sapiens

<400> SEQUENCE: 35

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175
```

Ser Arg Gly

<210> SEQ ID NO 36
<211> LENGTH: 311
<212> TYPE: PRT
<213> ORGANISM: Homo sapiens

<400> SEQUENCE: 36

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Glu Met Thr Ala Val Gly Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 37
<211> LENGTH: 6
<212> TYPE: PRT
<213> ORGANISM: Homo sapiens

<400> SEQUENCE: 37

Asp Arg Gly Ser Gln Ser
1               5

<210> SEQ ID NO 38
<211> LENGTH: 2
<212> TYPE: PRT
<213> ORGANISM: Homo sapiens

<400> SEQUENCE: 38

Ile Tyr
1

<210> SEQ ID NO 39
<211> LENGTH: 11
<212> TYPE: PRT
<213> ORGANISM: Homo sapiens

<400> SEQUENCE: 39

Cys Ala Ala Phe Ser Gly Tyr Ala Leu Asn Phe
1               5                   10

<210> SEQ ID NO 40
<211> LENGTH: 130
<212> TYPE: PRT
<213> ORGANISM: Homo sapiens

<400> SEQUENCE: 40

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Phe Ser Gly Tyr Ala Leu Asn Phe Gly Lys Gly Thr Ser Leu Leu Val
        115                 120                 125

Thr Pro
    130

<210> SEQ ID NO 41
<211> LENGTH: 141
<212> TYPE: PRT
<213> ORGANISM: Homo sapiens

<400> SEQUENCE: 41

His Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
130                 135                 140

<210> SEQ ID NO 42
<211> LENGTH: 271
<212> TYPE: PRT
<213> ORGANISM: Homo sapiens

<400> SEQUENCE: 42

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
                35                  40                  45

Arg Gly Ser Gln Ser Phe Phe Trp Tyr Arg Gln Tyr Ser Gly Lys Ser
            50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Ala
            100                 105                 110

Phe Ser Gly Tyr Ala Leu Asn Phe Gly Lys Gly Thr Ser Leu Leu Val
            115                 120                 125

Thr Pro His Ile Gln Asn Pro Asp Pro Ala Val Tyr Gln Leu Arg Asp
130                 135                 140

Ser Lys Ser Ser Asp Lys Ser Val Cys Leu Phe Thr Asp Phe Asp Ser
145                 150                 155                 160

Gln Thr Asn Val Ser Gln Ser Lys Asp Ser Asp Val Tyr Ile Thr Asp
                165                 170                 175

Lys Thr Val Leu Asp Met Arg Ser Met Asp Phe Lys Ser Asn Ser Ala
            180                 185                 190

Val Ala Trp Ser Asn Lys Ser Asp Phe Ala Cys Ala Asn Ala Phe Asn
            195                 200                 205

Asn Ser Ile Ile Pro Glu Asp Thr Phe Phe Pro Ser Pro Glu Ser Ser
    210                 215                 220

Cys Asp Val Lys Leu Val Glu Lys Ser Phe Glu Thr Asp Thr Asn Leu
225                 230                 235                 240

Asn Phe Gln Asn Leu Ser Val Ile Gly Phe Arg Ile Leu Leu Leu Lys
                245                 250                 255

Val Ala Gly Phe Asn Leu Leu Met Thr Leu Arg Leu Trp Ser Ser
            260                 265                 270

<210> SEQ ID NO 43
<211> LENGTH: 5
<212> TYPE: PRT

```
<213> ORGANISM: Homo sapiens

<400> SEQUENCE: 43

Ser Asn His Leu Tyr
1               5

<210> SEQ ID NO 44
<211> LENGTH: 6
<212> TYPE: PRT
<213> ORGANISM: Homo sapiens

<400> SEQUENCE: 44

Phe Tyr Asn Asn Glu Ile
1               5

<210> SEQ ID NO 45
<211> LENGTH: 12
<212> TYPE: PRT
<213> ORGANISM: Homo sapiens

<400> SEQUENCE: 45

Cys Ala Ser Ser Gln Tyr Thr Gly Glu Leu Phe Phe
1               5                   10

<210> SEQ ID NO 46
<211> LENGTH: 131
<212> TYPE: PRT
<213> ORGANISM: Homo sapiens

<400> SEQUENCE: 46

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gln Tyr Thr Gly Glu Leu Phe Phe Gly Glu Gly Ser Arg Leu
        115                 120                 125

Thr Val Leu
    130

<210> SEQ ID NO 47
<211> LENGTH: 179
<212> TYPE: PRT
<213> ORGANISM: Homo sapiens

<400> SEQUENCE: 47

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
```

```
            35                  40                  45
Gly Lys Glu Val His Ser Gly Val Ser Thr Asp Pro Gln Pro Leu Lys
 50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 48
<211> LENGTH: 310
<212> TYPE: PRT
<213> ORGANISM: Homo sapiens

<400> SEQUENCE: 48

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
                20                  25                  30

Gln Met Gly Gln Glu Val Ile Leu Arg Cys Val Pro Ile Ser Asn His
            35                  40                  45

Leu Tyr Phe Tyr Trp Tyr Arg Gln Ile Leu Gly Gln Lys Val Glu Phe
 50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala
            100                 105                 110

Ser Ser Gln Tyr Thr Gly Glu Leu Phe Phe Gly Glu Gly Ser Arg Leu
        115                 120                 125

Thr Val Leu Glu Asp Leu Lys Asn Val Phe Pro Pro Glu Val Ala Val
    130                 135                 140

Phe Glu Pro Ser Glu Ala Glu Ile Ser His Thr Gln Lys Ala Thr Leu
145                 150                 155                 160

Val Cys Leu Ala Thr Gly Phe Tyr Pro Asp His Val Glu Leu Ser Trp
                165                 170                 175

Trp Val Asn Gly Lys Glu Val His Ser Gly Val Ser Thr Asp Pro Gln
            180                 185                 190

Pro Leu Lys Glu Gln Pro Ala Leu Asn Asp Ser Arg Tyr Cys Leu Ser
        195                 200                 205

Ser Arg Leu Arg Val Ser Ala Thr Phe Trp Gln Asn Pro Arg Asn His
    210                 215                 220

Phe Arg Cys Gln Val Gln Phe Tyr Gly Leu Ser Glu Asn Asp Glu Trp
```

```
                225                 230                 235                 240
Thr Gln Asp Arg Ala Lys Pro Val Thr Gln Ile Val Ser Ala Glu Ala
                    245                 250                 255

Trp Gly Arg Ala Asp Cys Gly Phe Thr Ser Glu Ser Tyr Gln Gln Gly
                    260                 265                 270

Val Leu Ser Ala Thr Ile Leu Tyr Glu Ile Leu Leu Gly Lys Ala Thr
                    275                 280                 285

Leu Tyr Ala Val Leu Val Ser Ala Leu Val Leu Met Ala Met Val Lys
                    290                 295                 300

Arg Lys Asp Ser Arg Gly
305                 310

<210> SEQ ID NO 49
<211> LENGTH: 6
<212> TYPE: PRT
<213> ORGANISM: Homo sapiens

<400> SEQUENCE: 49

Asp Arg Gly Ser Gln Ser
1               5

<210> SEQ ID NO 50
<211> LENGTH: 2
<212> TYPE: PRT
<213> ORGANISM: Homo sapiens

<400> SEQUENCE: 50

Ile Tyr
1

<210> SEQ ID NO 51
<211> LENGTH: 10
<212> TYPE: PRT
<213> ORGANISM: Homo sapiens

<400> SEQUENCE: 51

Cys Ala Val Asn Gly Gly Asp Met Arg Phe
1               5                   10

<210> SEQ ID NO 52
<211> LENGTH: 129
<212> TYPE: PRT
<213> ORGANISM: Homo sapiens

<400> SEQUENCE: 52

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
                20                  25                  30

Ser Val Pro Glu Gly Ala Ile Ala Ser Leu Asn Cys Thr Tyr Ser Asp
            35                  40                  45

Arg Gly Ser Gln Ser Phe Phe Trp Tyr Arg Gln Tyr Ser Gly Lys Ser
        50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110
```

```
Asn Gly Gly Asp Met Arg Phe Gly Ala Gly Thr Arg Leu Thr Val Lys
            115                 120                 125

Pro

<210> SEQ ID NO 53
<211> LENGTH: 141
<212> TYPE: PRT
<213> ORGANISM: Homo sapiens

<400> SEQUENCE: 53

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 54
<211> LENGTH: 270
<212> TYPE: PRT
<213> ORGANISM: Homo sapiens

<400> SEQUENCE: 54

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Phe Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Asn Gly Gly Asp Met Arg Phe Gly Ala Gly Thr Arg Leu Thr Val Lys
        115                 120                 125

Pro Asn Ile Gln Asn Pro Asp Pro Ala Val Tyr Gln Leu Arg Asp Ser
    130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
```

```
                    165                 170                 175
Thr Val Leu Asp Met Arg Ser Met Asp Phe Lys Ser Asn Ser Ala Val
                180                 185                 190

Ala Trp Ser Asn Lys Ser Asp Phe Ala Cys Ala Asn Ala Phe Asn Asn
            195                 200                 205

Ser Ile Ile Pro Glu Asp Thr Phe Phe Pro Ser Pro Glu Ser Ser Cys
        210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
                260                 265                 270

<210> SEQ ID NO 55
<211> LENGTH: 5
<212> TYPE: PRT
<213> ORGANISM: Homo sapiens

<400> SEQUENCE: 55

Ser Asn His Leu Tyr
1               5

<210> SEQ ID NO 56
<211> LENGTH: 6
<212> TYPE: PRT
<213> ORGANISM: Homo sapiens

<400> SEQUENCE: 56

Phe Tyr Asn Asn Glu Ile
1               5

<210> SEQ ID NO 57
<211> LENGTH: 13
<212> TYPE: PRT
<213> ORGANISM: Homo sapiens

<400> SEQUENCE: 57

Cys Ala Ser Ser Gly Gln Gly Ala Leu Glu Gln Tyr Phe
1               5                   10

<210> SEQ ID NO 58
<211> LENGTH: 132
<212> TYPE: PRT
<213> ORGANISM: Homo sapiens

<400> SEQUENCE: 58

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95
```

Lys Ile Arg Ser Thr Lys Leu Glu Asp Ser Ala Met Tyr Phe Cys Ala
            100                 105                 110

Ser Ser Gly Gln Gly Ala Leu Glu Gln Tyr Phe Gly Pro Gly Thr Arg
        115                 120                 125

Leu Thr Val Thr
    130

<210> SEQ ID NO 59
<211> LENGTH: 179
<212> TYPE: PRT
<213> ORGANISM: Homo sapiens

<400> SEQUENCE: 59

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 60
<211> LENGTH: 311
<212> TYPE: PRT
<213> ORGANISM: Homo sapiens

<400> SEQUENCE: 60

Met Asp Thr Trp Leu Val Cys Trp Ala Ile Phe Ser Leu Leu Lys Ala
1               5                   10                  15

Gly Leu Thr Glu Pro Glu Val Thr Gln Thr Pro Ser His Gln Val Thr
            20                  25                  30

Gln Met Gly Gln Glu Val Ile Leu Arg Cys Val Pro Ile Ser Asn His
        35                  40                  45

Leu Tyr Phe Tyr Trp Tyr Arg Gln Ile Leu Gly Gln Lys Val Glu Phe
    50                  55                  60

Leu Val Ser Phe Tyr Asn Asn Glu Ile Ser Glu Lys Ser Glu Ile Phe
65                  70                  75                  80

Asp Asp Gln Phe Ser Val Glu Arg Pro Asp Gly Ser Asn Phe Thr Leu
                85                  90                  95

Lys Ile Arg Ser Thr Lys Leu Glu Asp Ser Ala Met Tyr Phe Cys Ala

```
                100                 105                 110
Ser Ser Gly Gln Gly Ala Leu Glu Gln Tyr Phe Gly Pro Gly Thr Arg
        115                 120                 125

Leu Thr Val Thr Glu Asp Leu Lys Asn Val Phe Pro Pro Glu Val Ala
        130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
    210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 61
<211> LENGTH: 6
<212> TYPE: PRT
<213> ORGANISM: Homo sapiens

<400> SEQUENCE: 61

Asn Ser Met Phe Asp Tyr
1               5

<210> SEQ ID NO 62
<211> LENGTH: 3
<212> TYPE: PRT
<213> ORGANISM: Homo sapiens

<400> SEQUENCE: 62

Ile Ser Ser
1

<210> SEQ ID NO 63
<211> LENGTH: 15
<212> TYPE: PRT
<213> ORGANISM: Homo sapiens

<400> SEQUENCE: 63

Cys Ala Ala Ser Gly Leu Tyr Asn Gln Gly Gly Lys Leu Ile Phe
1               5                   10                  15

<210> SEQ ID NO 64
<211> LENGTH: 140
<212> TYPE: PRT
<213> ORGANISM: Homo sapiens
```

<400> SEQUENCE: 64

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

Asn Ser Pro Ser Leu Ser Val Gln Glu Gly Arg Ile Ser Ile Leu Asn
            35                  40                  45

Cys Asp Tyr Thr Asn Ser Met Phe Asp Tyr Phe Leu Trp Tyr Lys Lys
    50                  55                  60

Tyr Pro Ala Glu Gly Pro Thr Phe Leu Ile Ser Ile Ser Ser Ile Lys
65                  70                  75                  80

Asp Lys Asn Glu Asp Gly Arg Phe Thr Val Phe Leu Asn Lys Ser Ala
                85                  90                  95

Lys His Leu Ser Leu His Ile Val Pro Ser Gln Pro Gly Asp Ser Ala
            100                 105                 110

Val Tyr Phe Cys Ala Ala Ser Gly Leu Tyr Asn Gln Gly Gly Lys Leu
            115                 120                 125

Ile Phe Gly Gln Gly Thr Glu Leu Ser Val Lys Pro
            130                 135                 140

<210> SEQ ID NO 65
<211> LENGTH: 141
<212> TYPE: PRT
<213> ORGANISM: Homo sapiens

<400> SEQUENCE: 65

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
            115                 120                 125

Gly Phe Asn Leu Leu Met Thr Leu Arg Leu Trp Ser Ser
            130                 135                 140

<210> SEQ ID NO 66
<211> LENGTH: 281
<212> TYPE: PRT
<213> ORGANISM: Homo sapiens

<400> SEQUENCE: 66

Met Ala Met Leu Leu Gly Ala Ser Val Leu Ile Leu Trp Leu Gln Pro
1               5                   10                  15

Asp Trp Val Asn Ser Gln Gln Lys Asn Asp Gln Gln Val Lys Gln
            20                  25                  30

```
Asn Ser Pro Ser Leu Ser Val Gln Glu Gly Arg Ile Ser Ile Leu Asn
            35                  40                  45
Cys Asp Tyr Thr Asn Ser Met Phe Asp Tyr Phe Leu Trp Tyr Lys Lys
 50                  55                  60
Tyr Pro Ala Glu Gly Pro Thr Phe Leu Ile Ser Ile Ser Ser Ile Lys
 65                  70                  75                  80
Asp Lys Asn Glu Asp Gly Arg Phe Thr Val Phe Leu Asn Lys Ser Ala
                 85                  90                  95
Lys His Leu Ser Leu His Ile Val Pro Ser Gln Pro Gly Asp Ser Ala
                100                 105                 110
Val Tyr Phe Cys Ala Ala Ser Gly Leu Tyr Asn Gln Gly Gly Lys Leu
                115                 120                 125
Ile Phe Gly Gln Gly Thr Glu Leu Ser Val Lys Pro Asn Ile Gln Asn
                130                 135                 140
Pro Asp Pro Ala Val Tyr Gln Leu Arg Asp Ser Lys Ser Ser Asp Lys
145                 150                 155                 160
Ser Val Cys Leu Phe Thr Asp Phe Asp Ser Gln Thr Asn Val Ser Gln
                165                 170                 175
Ser Lys Asp Ser Asp Val Tyr Ile Thr Asp Lys Thr Val Leu Asp Met
                180                 185                 190
Arg Ser Met Asp Phe Lys Ser Asn Ser Ala Val Ala Trp Ser Asn Lys
                195                 200                 205
Ser Asp Phe Ala Cys Ala Asn Ala Phe Asn Asn Ser Ile Ile Pro Glu
                210                 215                 220
Asp Thr Phe Phe Pro Ser Pro Glu Ser Ser Cys Asp Val Lys Leu Val
225                 230                 235                 240
Glu Lys Ser Phe Glu Thr Asp Thr Asn Leu Asn Phe Gln Asn Leu Ser
                245                 250                 255
Val Ile Gly Phe Arg Ile Leu Leu Leu Lys Val Ala Gly Phe Asn Leu
                260                 265                 270
Leu Met Thr Leu Arg Leu Trp Ser Ser
                275                 280

<210> SEQ ID NO 67
<211> LENGTH: 5
<212> TYPE: PRT
<213> ORGANISM: Homo sapiens

<400> SEQUENCE: 67

Leu Gly His Asp Thr
1               5

<210> SEQ ID NO 68
<211> LENGTH: 6
<212> TYPE: PRT
<213> ORGANISM: Homo sapiens

<400> SEQUENCE: 68

Tyr Asn Asn Lys Glu Leu
1               5

<210> SEQ ID NO 69
<211> LENGTH: 14
<212> TYPE: PRT
<213> ORGANISM: Homo sapiens

<400> SEQUENCE: 69

Cys Ala Ser Ser Leu Gly Asp Arg Gly Tyr Glu Gln Tyr Phe
```

<210> SEQ ID NO 70
<211> LENGTH: 132
<212> TYPE: PRT
<213> ORGANISM: Homo sapiens

<400> SEQUENCE: 70

Met Gly Cys Arg Leu Leu Cys Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Leu Gly Asp Arg Gly Tyr Glu Gln Tyr Phe Gly Pro Gly Thr Arg
        115                 120                 125

Leu Thr Val Thr
    130

<210> SEQ ID NO 71
<211> LENGTH: 179
<212> TYPE: PRT
<213> ORGANISM: Homo sapiens

<400> SEQUENCE: 71

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 72
<211> LENGTH: 311
<212> TYPE: PRT
<213> ORGANISM: Homo sapiens

<400> SEQUENCE: 72

Met Gly Cys Arg Leu Leu Cys Val Val Phe Cys Leu Leu Gln Ala
1               5                   10                  15

Gly Pro Leu Asp Thr Ala Val Ser Gln Thr Pro Lys Tyr Leu Val Thr
            20                  25                  30

Gln Met Gly Asn Asp Lys Ser Ile Lys Cys Glu Gln Asn Leu Gly His
        35                  40                  45

Asp Thr Met Tyr Trp Tyr Lys Gln Asp Ser Lys Lys Phe Leu Lys Ile
    50                  55                  60

Met Phe Ser Tyr Asn Asn Lys Glu Leu Ile Ile Asn Glu Thr Val Pro
65                  70                  75                  80

Asn Arg Phe Ser Pro Lys Ser Pro Asp Lys Ala His Leu Asn Leu His
                85                  90                  95

Ile Asn Ser Leu Glu Leu Gly Asp Ser Ala Val Tyr Phe Cys Ala Ser
            100                 105                 110

Ser Leu Gly Asp Arg Gly Tyr Glu Gln Tyr Phe Gly Pro Gly Thr Arg
        115                 120                 125

Leu Thr Val Thr Glu Asp Leu Lys Asn Val Phe Pro Pro Glu Val Ala
    130                 135                 140

Val Phe Glu Pro Ser Glu Ala Glu Ile Ser His Thr Gln Lys Ala Thr
145                 150                 155                 160

Leu Val Cys Leu Ala Thr Gly Phe Tyr Pro Asp His Val Glu Leu Ser
                165                 170                 175

Trp Trp Val Asn Gly Lys Glu Val His Ser Gly Val Ser Thr Asp Pro
            180                 185                 190

Gln Pro Leu Lys Glu Gln Pro Ala Leu Asn Asp Ser Arg Tyr Cys Leu
        195                 200                 205

Ser Ser Arg Leu Arg Val Ser Ala Thr Phe Trp Gln Asn Pro Arg Asn
210                 215                 220

His Phe Arg Cys Gln Val Gln Phe Tyr Gly Leu Ser Glu Asn Asp Glu
225                 230                 235                 240

Trp Thr Gln Asp Arg Ala Lys Pro Val Thr Gln Ile Val Ser Ala Glu
                245                 250                 255

Ala Trp Gly Arg Ala Asp Cys Gly Phe Thr Ser Glu Ser Tyr Gln Gln
            260                 265                 270

Gly Val Leu Ser Ala Thr Ile Leu Tyr Glu Ile Leu Leu Gly Lys Ala
        275                 280                 285

Thr Leu Tyr Ala Val Leu Val Ser Ala Leu Val Leu Met Ala Met Val
    290                 295                 300

Lys Arg Lys Asp Ser Arg Gly
305                 310

<210> SEQ ID NO 73
<211> LENGTH: 6
<212> TYPE: PRT
<213> ORGANISM: Homo sapiens

<400> SEQUENCE: 73

Asp Ser Ser Ser Thr Tyr
1               5

<210> SEQ ID NO 74
<211> LENGTH: 3
<212> TYPE: PRT
<213> ORGANISM: Homo sapiens

<400> SEQUENCE: 74

Ile Phe Ser
1

<210> SEQ ID NO 75
<211> LENGTH: 12
<212> TYPE: PRT
<213> ORGANISM: Homo sapiens

<400> SEQUENCE: 75

Cys Ala Glu Ile Asn Asn Asn Ala Arg Leu Met Phe
1               5                   10

<210> SEQ ID NO 76
<211> LENGTH: 131
<212> TYPE: PRT
<213> ORGANISM: Homo sapiens

<400> SEQUENCE: 76

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
        50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ile Asn Asn Asn Ala Arg Leu Met Phe Gly Asp Gly Thr Gln Leu Val
        115                 120                 125

Val Lys Pro
    130

<210> SEQ ID NO 77
<211> LENGTH: 141
<212> TYPE: PRT
<213> ORGANISM: Homo sapiens

<400> SEQUENCE: 77

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
                20                  25                  30

Asn Val Ser Gln Ser Lys Asp Ser Asp Val Tyr Ile Thr Asp Lys Thr
            35                  40                  45

Val Leu Asp Met Arg Ser Met Asp Phe Lys Ser Asn Ser Ala Val Ala
        50                  55                  60

Trp Ser Asn Lys Ser Asp Phe Ala Cys Ala Asn Ala Phe Asn Asn Ser

```
                65                  70                  75                  80
Ile Ile Pro Glu Asp Thr Phe Phe Pro Ser Pro Glu Ser Ser Cys Asp
                    85                  90                  95

Val Lys Leu Val Glu Lys Ser Phe Glu Thr Asp Thr Asn Leu Asn Phe
                100                 105                 110

Gln Asn Leu Ser Val Ile Gly Phe Arg Ile Leu Leu Lys Val Ala
                115                 120                 125

Gly Phe Asn Leu Leu Met Thr Leu Arg Leu Trp Ser Ser
                130                 135                 140

<210> SEQ ID NO 78
<211> LENGTH: 272
<212> TYPE: PRT
<213> ORGANISM: Homo sapiens

<400> SEQUENCE: 78

Met Lys Thr Phe Ala Gly Phe Ser Phe Leu Phe Leu Trp Leu Gln Leu
1               5                   10                  15

Asp Cys Met Ser Arg Gly Glu Asp Val Glu Gln Ser Leu Phe Leu Ser
                20                  25                  30

Val Arg Glu Gly Asp Ser Ser Val Ile Asn Cys Thr Tyr Thr Asp Ser
            35                  40                  45

Ser Ser Thr Tyr Leu Tyr Trp Tyr Lys Gln Glu Pro Gly Ala Gly Leu
50                  55                  60

Gln Leu Leu Thr Tyr Ile Phe Ser Asn Met Asp Met Lys Gln Asp Gln
65                  70                  75                  80

Arg Leu Thr Val Leu Leu Asn Lys Lys Asp Lys His Leu Ser Leu Arg
                85                  90                  95

Ile Ala Asp Thr Gln Thr Gly Asp Ser Ala Ile Tyr Phe Cys Ala Glu
            100                 105                 110

Ile Asn Asn Asn Ala Arg Leu Met Phe Gly Asp Gly Thr Gln Leu Val
        115                 120                 125

Val Lys Pro Asn Ile Gln Asn Pro Asp Pro Ala Val Tyr Gln Leu Arg
130                 135                 140

Asp Ser Lys Ser Ser Asp Lys Ser Val Cys Leu Phe Thr Asp Phe Asp
145                 150                 155                 160

Ser Gln Thr Asn Val Ser Gln Ser Lys Asp Ser Asp Val Tyr Ile Thr
                165                 170                 175

Asp Lys Thr Val Leu Asp Met Arg Ser Met Asp Phe Lys Ser Asn Ser
            180                 185                 190

Ala Val Ala Trp Ser Asn Lys Ser Asp Phe Ala Cys Ala Asn Ala Phe
        195                 200                 205

Asn Asn Ser Ile Ile Pro Glu Asp Thr Phe Phe Pro Ser Pro Glu Ser
    210                 215                 220

Ser Cys Asp Val Lys Leu Val Glu Lys Ser Phe Glu Thr Asp Thr Asn
225                 230                 235                 240

Leu Asn Phe Gln Asn Leu Ser Val Ile Gly Phe Arg Ile Leu Leu Leu
                245                 250                 255

Lys Val Ala Gly Phe Asn Leu Leu Met Thr Leu Arg Leu Trp Ser Ser
            260                 265                 270

<210> SEQ ID NO 79
<211> LENGTH: 5
<212> TYPE: PRT
<213> ORGANISM: Homo sapiens
```

<400> SEQUENCE: 79

Pro Arg His Asp Thr
1               5

<210> SEQ ID NO 80
<211> LENGTH: 6
<212> TYPE: PRT
<213> ORGANISM: Homo sapiens

<400> SEQUENCE: 80

Phe Tyr Glu Lys Met Gln
1               5

<210> SEQ ID NO 81
<211> LENGTH: 13
<212> TYPE: PRT
<213> ORGANISM: Homo sapiens

<400> SEQUENCE: 81

Cys Ala Ser Ser Pro Asp Gln Asn Thr Gln Tyr Phe
1               5                  10

<210> SEQ ID NO 82
<211> LENGTH: 141
<212> TYPE: PRT
<213> ORGANISM: Homo sapiens

<400> SEQUENCE: 82

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Asp Gln Asn
        115                 120                 125

Thr Gln Tyr Phe Gly Pro Gly Thr Arg Leu Thr Val Leu
    130                 135                 140

<210> SEQ ID NO 83
<211> LENGTH: 179
<212> TYPE: PRT
<213> ORGANISM: Homo sapiens

<400> SEQUENCE: 83

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

```
Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
            130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 84
<211> LENGTH: 320
<212> TYPE: PRT
<213> ORGANISM: Homo sapiens

<400> SEQUENCE: 84

Met Leu Ser Pro Asp Leu Pro Asp Ser Ala Trp Asn Thr Arg Leu Leu
1               5                   10                  15

Cys His Val Met Leu Cys Leu Leu Gly Ala Val Ser Val Ala Ala Gly
                20                  25                  30

Val Ile Gln Ser Pro Arg His Leu Ile Lys Glu Lys Arg Glu Thr Ala
            35                  40                  45

Thr Leu Lys Cys Tyr Pro Ile Pro Arg His Asp Thr Val Tyr Trp Tyr
        50                  55                  60

Gln Gln Gly Pro Gly Gln Asp Pro Gln Phe Leu Ile Ser Phe Tyr Glu
65                  70                  75                  80

Lys Met Gln Ser Asp Lys Gly Ser Ile Pro Asp Arg Phe Ser Ala Gln
                85                  90                  95

Gln Phe Ser Asp Tyr His Ser Glu Leu Asn Met Ser Ser Leu Glu Leu
            100                 105                 110

Gly Asp Ser Ala Leu Tyr Phe Cys Ala Ser Ser Pro Pro Asp Gln Asn
            115                 120                 125

Thr Gln Tyr Phe Gly Pro Gly Thr Arg Leu Thr Val Leu Glu Asp Leu
            130                 135                 140

Lys Asn Val Phe Pro Pro Glu Val Ala Val Phe Glu Pro Ser Glu Ala
145                 150                 155                 160

Glu Ile Ser His Thr Gln Lys Ala Thr Leu Val Cys Leu Ala Thr Gly
                165                 170                 175

Phe Tyr Pro Asp His Val Glu Leu Ser Trp Trp Val Asn Gly Lys Glu
            180                 185                 190

Val His Ser Gly Val Ser Thr Asp Pro Gln Pro Leu Lys Glu Gln Pro
            195                 200                 205

Ala Leu Asn Asp Ser Arg Tyr Cys Leu Ser Ser Arg Leu Arg Val Ser
        210                 215                 220

Ala Thr Phe Trp Gln Asn Pro Arg Asn His Phe Arg Cys Gln Val Gln
225                 230                 235                 240
```

```
Phe Tyr Gly Leu Ser Glu Asn Asp Glu Trp Thr Gln Asp Arg Ala Lys
            245                 250                 255

Pro Val Thr Gln Ile Val Ser Ala Glu Ala Trp Gly Arg Ala Asp Cys
        260                 265                 270

Gly Phe Thr Ser Glu Ser Tyr Gln Gln Gly Val Leu Ser Ala Thr Ile
        275                 280                 285

Leu Tyr Glu Ile Leu Leu Gly Lys Ala Thr Leu Tyr Ala Val Leu Val
        290                 295                 300

Ser Ala Leu Val Leu Met Ala Met Val Lys Arg Lys Asp Ser Arg Gly
305                 310                 315                 320
```

<210> SEQ ID NO 85
<211> LENGTH: 6
<212> TYPE: PRT
<213> ORGANISM: Homo sapiens

<400> SEQUENCE: 85

```
Ser Ser Val Pro Pro Tyr
1               5
```

<210> SEQ ID NO 86
<211> LENGTH: 4
<212> TYPE: PRT
<213> ORGANISM: Homo sapiens

<400> SEQUENCE: 86

```
Tyr Thr Thr Gly
1
```

<210> SEQ ID NO 87
<211> LENGTH: 13
<212> TYPE: PRT
<213> ORGANISM: Homo sapiens

<400> SEQUENCE: 87

```
Cys Ala Val Arg Ile Phe Gly Asn Glu Lys Leu Thr Phe
1               5                   10
```

<210> SEQ ID NO 88
<211> LENGTH: 132
<212> TYPE: PRT
<213> ORGANISM: Homo sapiens

<400> SEQUENCE: 88

```
Met Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
        50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Arg Ile Phe Gly Asn Glu Lys Leu Thr Phe Gly Thr Gly Thr Arg Leu
        115                 120                 125
```

Thr Ile Ile Pro
    130

<210> SEQ ID NO 89
<211> LENGTH: 141
<212> TYPE: PRT
<213> ORGANISM: Homo sapiens

<400> SEQUENCE: 89

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 90
<211> LENGTH: 273
<212> TYPE: PRT
<213> ORGANISM: Homo sapiens

<400> SEQUENCE: 90

Met Leu Leu Leu Leu Val Pro Val Leu Glu Val Ile Phe Thr Leu Gly
1               5                   10                  15

Gly Thr Arg Ala Gln Ser Val Thr Gln Leu Gly Ser His Val Ser Val
            20                  25                  30

Ser Glu Gly Ala Leu Val Leu Leu Arg Cys Asn Tyr Ser Ser Ser Val
        35                  40                  45

Pro Pro Tyr Leu Phe Trp Tyr Val Gln Tyr Pro Asn Gln Gly Leu Gln
    50                  55                  60

Leu Leu Leu Lys Tyr Thr Thr Gly Ala Thr Leu Val Lys Gly Ile Asn
65                  70                  75                  80

Gly Phe Glu Ala Glu Phe Lys Lys Ser Glu Thr Ser Phe His Leu Thr
                85                  90                  95

Lys Pro Ser Ala His Met Ser Asp Ala Ala Glu Tyr Phe Cys Ala Val
            100                 105                 110

Arg Ile Phe Gly Asn Glu Lys Leu Thr Phe Gly Thr Gly Thr Arg Leu
        115                 120                 125

Thr Ile Ile Pro Asn Ile Gln Asn Pro Asp Pro Ala Val Tyr Gln Leu
    130                 135                 140

Arg Asp Ser Lys Ser Ser Asp Lys Ser Val Cys Leu Phe Thr Asp Phe
145                 150                 155                 160

Asp Ser Gln Thr Asn Val Ser Gln Ser Lys Asp Ser Asp Val Tyr Ile
                165                 170                 175

Thr Asp Lys Thr Val Leu Asp Met Arg Ser Met Asp Phe Lys Ser Asn
            180                 185                 190

Ser Ala Val Ala Trp Ser Asn Lys Ser Asp Phe Ala Cys Ala Asn Ala
            195                 200                 205

Phe Asn Asn Ser Ile Ile Pro Glu Asp Thr Phe Phe Pro Ser Pro Glu
            210                 215                 220

Ser Ser Cys Asp Val Lys Leu Val Glu Lys Ser Phe Glu Thr Asp Thr
225                 230                 235                 240

Asn Leu Asn Phe Gln Asn Leu Ser Val Ile Gly Phe Arg Ile Leu Leu
                245                 250                 255

Leu Lys Val Ala Gly Phe Asn Leu Leu Met Thr Leu Arg Leu Trp Ser
            260                 265                 270

Ser

<210> SEQ ID NO 91
<211> LENGTH: 5
<212> TYPE: PRT
<213> ORGANISM: Homo sapiens

<400> SEQUENCE: 91

Met Asp His Glu Asn
1               5

<210> SEQ ID NO 92
<211> LENGTH: 6
<212> TYPE: PRT
<213> ORGANISM: Homo sapiens

<400> SEQUENCE: 92

Ser Tyr Asp Val Lys Met
1               5

<210> SEQ ID NO 93
<211> LENGTH: 15
<212> TYPE: PRT
<213> ORGANISM: Homo sapiens

<400> SEQUENCE: 93

Cys Ala Ser Ser Leu Met Gly Glu Leu Thr Gly Glu Leu Phe Phe
1               5                   10                  15

<210> SEQ ID NO 94
<211> LENGTH: 133
<212> TYPE: PRT
<213> ORGANISM: Homo sapiens

<400> SEQUENCE: 94

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
            35                  40                  45

Glu Asn Met Phe Trp Tyr Arg Gln Asp Pro Gly Leu Gly Leu Arg Leu
        50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Met Gly Glu Leu Thr Gly Glu Leu Phe Phe Gly Glu Gly Ser
        115                 120                 125

Arg Leu Thr Val Leu
    130

<210> SEQ ID NO 95
<211> LENGTH: 179
<212> TYPE: PRT
<213> ORGANISM: Homo sapiens

<400> SEQUENCE: 95

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 96
<211> LENGTH: 312
<212> TYPE: PRT
<213> ORGANISM: Homo sapiens

<400> SEQUENCE: 96

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Leu Met Gly Glu Leu Thr Gly Glu Leu Phe Phe Gly Glu Gly Ser
        115                 120                 125

Arg Leu Thr Val Leu Glu Asp Leu Lys Asn Val Phe Pro Pro Glu Val
    130                 135                 140

Ala Val Phe Glu Pro Ser Glu Ala Glu Ile Ser His Thr Gln Lys Ala
145                 150                 155                 160

Thr Leu Val Cys Leu Ala Thr Gly Phe Tyr Pro Asp His Val Glu Leu
                165                 170                 175

Ser Trp Trp Val Asn Gly Lys Glu Val His Ser Gly Val Ser Thr Asp
            180                 185                 190

Pro Gln Pro Leu Lys Glu Gln Pro Ala Leu Asn Asp Ser Arg Tyr Cys
        195                 200                 205

Leu Ser Ser Arg Leu Arg Val Ser Ala Thr Phe Trp Gln Asn Pro Arg
    210                 215                 220

Asn His Phe Arg Cys Gln Val Gln Phe Tyr Gly Leu Ser Glu Asn Asp
225                 230                 235                 240

Glu Trp Thr Gln Asp Arg Ala Lys Pro Val Thr Gln Ile Val Ser Ala
                245                 250                 255

Glu Ala Trp Gly Arg Ala Asp Cys Gly Phe Thr Ser Glu Ser Tyr Gln
            260                 265                 270

Gln Gly Val Leu Ser Ala Thr Ile Leu Tyr Glu Ile Leu Leu Gly Lys
        275                 280                 285

Ala Thr Leu Tyr Ala Val Leu Val Ser Ala Leu Val Leu Met Ala Met
    290                 295                 300

Val Lys Arg Lys Asp Ser Arg Gly
305                 310

<210> SEQ ID NO 97
<211> LENGTH: 6
<212> TYPE: PRT
<213> ORGANISM: Homo sapiens

<400> SEQUENCE: 97

Asn Ser Ala Phe Gln Tyr
1               5

<210> SEQ ID NO 98
<211> LENGTH: 2
<212> TYPE: PRT
<213> ORGANISM: Homo sapiens

<400> SEQUENCE: 98

Thr Tyr
1

<210> SEQ ID NO 99
<211> LENGTH: 15
<212> TYPE: PRT
<213> ORGANISM: Homo sapiens

<400> SEQUENCE: 99

Cys Ala Met Met Gly Asp Thr Gly Thr Ala Ser Lys Leu Thr Phe
1               5                   10                  15

<210> SEQ ID NO 100
<211> LENGTH: 135
<212> TYPE: PRT

<213> ORGANISM: Homo sapiens

<400> SEQUENCE: 100

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

Leu Ser Val Pro Glu Gly Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
    50                  55                  60

Gly Pro Glu Leu Leu Met Tyr Thr Tyr Ser Ser Gly Asn Lys Glu Asp
65                  70                  75                  80

Gly Arg Phe Thr Ala Gln Val Asp Lys Ser Ser Lys Tyr Ile Ser Leu
                85                  90                  95

Phe Ile Arg Asp Ser Gln Pro Ser Asp Ser Ala Thr Tyr Leu Cys Ala
            100                 105                 110

Met Met Gly Asp Thr Gly Thr Ala Ser Lys Leu Thr Phe Gly Thr Gly
        115                 120                 125

Thr Arg Leu Gln Val Thr Leu
    130                 135

<210> SEQ ID NO 101
<211> LENGTH: 141
<212> TYPE: PRT
<213> ORGANISM: Homo sapiens

<400> SEQUENCE: 101

Asp Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140

<210> SEQ ID NO 102
<211> LENGTH: 276
<212> TYPE: PRT
<213> ORGANISM: Homo sapiens

<400> SEQUENCE: 102

Met Met Lys Ser Leu Arg Val Leu Leu Val Ile Leu Trp Leu Gln Leu
1               5                   10                  15

Ser Trp Val Trp Ser Gln Gln Lys Glu Val Glu Gln Asp Pro Gly Pro
            20                  25                  30

```
Leu Ser Val Pro Glu Ala Ile Val Ser Leu Asn Cys Thr Tyr Ser
        35                  40                  45

Asn Ser Ala Phe Gln Tyr Phe Met Trp Tyr Arg Gln Tyr Ser Arg Lys
 50                  55                  60

Gly Pro Glu Leu Leu Met Tyr Thr Tyr Ser Ser Gly Asn Lys Glu Asp
 65                  70                  75                  80

Gly Arg Phe Thr Ala Gln Val Asp Lys Ser Ser Lys Tyr Ile Ser Leu
                 85                  90                  95

Phe Ile Arg Asp Ser Gln Pro Ser Asp Ser Ala Thr Tyr Leu Cys Ala
            100                 105                 110

Met Met Gly Asp Thr Gly Thr Ala Ser Lys Leu Thr Phe Gly Thr Gly
            115                 120                 125

Thr Arg Leu Gln Val Thr Leu Asp Ile Gln Asn Pro Asp Pro Ala Val
        130                 135                 140

Tyr Gln Leu Arg Asp Ser Lys Ser Ser Asp Lys Ser Val Cys Leu Phe
145                 150                 155                 160

Thr Asp Phe Asp Ser Gln Thr Asn Val Ser Gln Ser Lys Asp Ser Asp
                165                 170                 175

Val Tyr Ile Thr Asp Lys Thr Val Leu Asp Met Arg Ser Met Asp Phe
            180                 185                 190

Lys Ser Asn Ser Ala Val Ala Trp Ser Asn Lys Ser Asp Phe Ala Cys
            195                 200                 205

Ala Asn Ala Phe Asn Asn Ser Ile Ile Pro Glu Asp Thr Phe Phe Pro
            210                 215                 220

Ser Pro Glu Ser Ser Cys Asp Val Lys Leu Val Glu Lys Ser Phe Glu
225                 230                 235                 240

Thr Asp Thr Asn Leu Asn Phe Gln Asn Leu Ser Val Ile Gly Phe Arg
                245                 250                 255

Ile Leu Leu Leu Lys Val Ala Gly Phe Asn Leu Leu Met Thr Leu Arg
            260                 265                 270

Leu Trp Ser Ser
            275

<210> SEQ ID NO 103
<211> LENGTH: 5
<212> TYPE: PRT
<213> ORGANISM: Homo sapiens

<400> SEQUENCE: 103

Met Asp His Glu Asn
1               5

<210> SEQ ID NO 104
<211> LENGTH: 6
<212> TYPE: PRT
<213> ORGANISM: Homo sapiens

<400> SEQUENCE: 104

Ser Tyr Asp Val Lys Met
1               5

<210> SEQ ID NO 105
<211> LENGTH: 12
<212> TYPE: PRT
<213> ORGANISM: Homo sapiens

<400> SEQUENCE: 105
```

Cys Ala Ser Ser Phe Gly Gly Tyr Glu Gln Tyr Phe
1               5                   10

<210> SEQ ID NO 106
<211> LENGTH: 130
<212> TYPE: PRT
<213> ORGANISM: Homo sapiens

<400> SEQUENCE: 106

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Phe Gly Gly Tyr Glu Gln Tyr Phe Gly Pro Gly Thr Arg Leu Thr
        115                 120                 125

Val Thr
    130

<210> SEQ ID NO 107
<211> LENGTH: 179
<212> TYPE: PRT
<213> ORGANISM: Homo sapiens

<400> SEQUENCE: 107

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 108
<211> LENGTH: 309
<212> TYPE: PRT
<213> ORGANISM: Homo sapiens

<400> SEQUENCE: 108

Met Gly Ile Arg Leu Leu Cys Arg Val Ala Phe Cys Phe Leu Ala Val
1               5                   10                  15

Gly Leu Val Asp Val Lys Val Thr Gln Ser Ser Arg Tyr Leu Val Lys
            20                  25                  30

Arg Thr Gly Glu Lys Val Phe Leu Glu Cys Val Gln Asp Met Asp His
        35                  40                  45

Glu Asn Met Phe Trp Tyr Arg Gln Asp Pro Gly Leu Gly Leu Arg Leu
    50                  55                  60

Ile Tyr Phe Ser Tyr Asp Val Lys Met Lys Glu Lys Gly Asp Ile Pro
65                  70                  75                  80

Glu Gly Tyr Ser Val Ser Arg Glu Lys Lys Glu Arg Phe Ser Leu Ile
                85                  90                  95

Leu Glu Ser Ala Ser Thr Asn Gln Thr Ser Met Tyr Leu Cys Ala Ser
            100                 105                 110

Ser Phe Gly Gly Tyr Glu Gln Tyr Phe Gly Pro Gly Thr Arg Leu Thr
        115                 120                 125

Val Thr Glu Asp Leu Lys Asn Val Phe Pro Pro Glu Val Ala Val Phe
130                 135                 140

Glu Pro Ser Glu Ala Glu Ile Ser His Thr Gln Lys Ala Thr Leu Val
145                 150                 155                 160

Cys Leu Ala Thr Gly Phe Tyr Pro Asp His Val Glu Leu Ser Trp Trp
                165                 170                 175

Val Asn Gly Lys Glu Val His Ser Gly Val Ser Thr Asp Pro Gln Pro
            180                 185                 190

Leu Lys Glu Gln Pro Ala Leu Asn Asp Ser Arg Tyr Cys Leu Ser Ser
        195                 200                 205

Arg Leu Arg Val Ser Ala Thr Phe Trp Gln Asn Pro Arg Asn His Phe
210                 215                 220

Arg Cys Gln Val Gln Phe Tyr Gly Leu Ser Glu Asn Asp Glu Trp Thr
225                 230                 235                 240

Gln Asp Arg Ala Lys Pro Val Thr Gln Ile Val Ser Ala Glu Ala Trp
                245                 250                 255

Gly Arg Ala Asp Cys Gly Phe Thr Ser Glu Ser Tyr Gln Gln Gly Val
            260                 265                 270

Leu Ser Ala Thr Ile Leu Tyr Glu Ile Leu Leu Gly Lys Ala Thr Leu
        275                 280                 285

Tyr Ala Val Leu Val Ser Ala Leu Val Leu Met Ala Met Val Lys Arg
290                 295                 300

Lys Asp Ser Arg Gly
305

<210> SEQ ID NO 109
<211> LENGTH: 6
<212> TYPE: PRT
<213> ORGANISM: Homo sapiens

<400> SEQUENCE: 109

Asp Arg Gly Ser Gln Ser

```
1               5

<210> SEQ ID NO 110
<211> LENGTH: 2
<212> TYPE: PRT
<213> ORGANISM: Homo sapiens

<400> SEQUENCE: 110

Ile Tyr
1

<210> SEQ ID NO 111
<211> LENGTH: 10
<212> TYPE: PRT
<213> ORGANISM: Homo sapiens

<400> SEQUENCE: 111

Cys Ala Val Gln Pro His Asp Met Arg Phe
1               5                   10

<210> SEQ ID NO 112
<211> LENGTH: 129
<212> TYPE: PRT
<213> ORGANISM: Homo sapiens

<400> SEQUENCE: 112

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Gln Pro His Asp Met Arg Phe Gly Ala Gly Thr Arg Leu Thr Val Lys
        115                 120                 125

Pro

<210> SEQ ID NO 113
<211> LENGTH: 141
<212> TYPE: PRT
<213> ORGANISM: Homo sapiens

<400> SEQUENCE: 113

Asn Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
```

```
            65                  70                  75                  80
Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Lys Val Ala
            115                 120                 125

Gly Phe Asn Leu Leu Met Thr Leu Arg Leu Trp Ser Ser
130                 135                 140

<210> SEQ ID NO 114
<211> LENGTH: 270
<212> TYPE: PRT
<213> ORGANISM: Homo sapiens

<400> SEQUENCE: 114

Met Lys Ser Leu Arg Val Leu Leu Val Ile Leu Trp Leu Gln Leu Ser
1               5                   10                  15

Trp Val Trp Ser Gln Gln Lys Glu Val Glu Gln Asn Ser Gly Pro Leu
            20                  25                  30

Ser Val Pro Glu Gly Ala Ile Ala Ser Leu Asn Cys Thr Tyr Ser Asp
        35                  40                  45

Arg Gly Ser Gln Ser Phe Phe Trp Tyr Arg Gln Tyr Ser Gly Lys Ser
    50                  55                  60

Pro Glu Leu Ile Met Ser Ile Tyr Ser Asn Gly Asp Lys Glu Asp Gly
65                  70                  75                  80

Arg Phe Thr Ala Gln Leu Asn Lys Ala Ser Gln Tyr Val Ser Leu Leu
                85                  90                  95

Ile Arg Asp Ser Gln Pro Ser Asp Ser Ala Thr Tyr Leu Cys Ala Val
            100                 105                 110

Gln Pro His Asp Met Arg Phe Gly Ala Gly Thr Arg Leu Thr Val Lys
            115                 120                 125

Pro Asn Ile Gln Asn Pro Asp Pro Ala Val Tyr Gln Leu Arg Asp Ser
130                 135                 140

Lys Ser Ser Asp Lys Ser Val Cys Leu Phe Thr Asp Phe Asp Ser Gln
145                 150                 155                 160

Thr Asn Val Ser Gln Ser Lys Asp Ser Asp Val Tyr Ile Thr Asp Lys
                165                 170                 175

Thr Val Leu Asp Met Arg Ser Met Asp Phe Lys Ser Asn Ser Ala Val
            180                 185                 190

Ala Trp Ser Asn Lys Ser Asp Phe Ala Cys Ala Asn Ala Phe Asn Asn
        195                 200                 205

Ser Ile Ile Pro Glu Asp Thr Phe Phe Pro Ser Pro Glu Ser Ser Cys
    210                 215                 220

Asp Val Lys Leu Val Glu Lys Ser Phe Glu Thr Asp Thr Asn Leu Asn
225                 230                 235                 240

Phe Gln Asn Leu Ser Val Ile Gly Phe Arg Ile Leu Leu Leu Lys Val
                245                 250                 255

Ala Gly Phe Asn Leu Leu Met Thr Leu Arg Leu Trp Ser Ser
            260                 265                 270

<210> SEQ ID NO 115
<211> LENGTH: 6
<212> TYPE: PRT
<213> ORGANISM: Homo sapiens
```

-continued

```
<400> SEQUENCE: 115

Gly Thr Ser Asn Pro Asn
1               5

<210> SEQ ID NO 116
<211> LENGTH: 5
<212> TYPE: PRT
<213> ORGANISM: Homo sapiens

<400> SEQUENCE: 116

Ser Val Gly Ile Gly
1               5

<210> SEQ ID NO 117
<211> LENGTH: 12
<212> TYPE: PRT
<213> ORGANISM: Homo sapiens

<400> SEQUENCE: 117

Cys Ala Trp Ser Gly Leu Val Ala Glu Gln Phe Phe
1               5                   10

<210> SEQ ID NO 118
<211> LENGTH: 128
<212> TYPE: PRT
<213> ORGANISM: Homo sapiens

<400> SEQUENCE: 118

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
                20                  25                  30

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
        50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Leu Val Ala Glu Gln Phe Phe Gly Pro Gly Thr Arg Leu Thr Val Leu
        115                 120                 125

<210> SEQ ID NO 119
<211> LENGTH: 179
<212> TYPE: PRT
<213> ORGANISM: Homo sapiens

<400> SEQUENCE: 119

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
                20                  25                  30

Ala Thr Gly Phe Tyr Pro Asp His Val Glu Leu Ser Trp Trp Val Asn
            35                  40                  45

Gly Lys Glu Val His Ser Gly Val Ser Thr Asp Pro Gln Pro Leu Lys
        50                  55                  60
```

```
Glu Gln Pro Ala Leu Asn Asp Ser Arg Tyr Cys Leu Ser Ser Arg Leu
 65                  70                  75                  80

Arg Val Ser Ala Thr Phe Trp Gln Asn Pro Arg Asn His Phe Arg Cys
                 85                  90                  95

Gln Val Gln Phe Tyr Gly Leu Ser Glu Asn Asp Glu Trp Thr Gln Asp
                100                 105                 110

Arg Ala Lys Pro Val Thr Gln Ile Val Ser Ala Glu Ala Trp Gly Arg
            115                 120                 125

Ala Asp Cys Gly Phe Thr Ser Glu Ser Tyr Gln Gln Gly Val Leu Ser
        130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 120
<211> LENGTH: 307
<212> TYPE: PRT
<213> ORGANISM: Homo sapiens

<400> SEQUENCE: 120

Met Leu Cys Ser Leu Leu Ala Leu Leu Leu Gly Thr Phe Phe Gly Val
1               5                   10                  15

Arg Ser Gln Thr Ile His Gln Trp Pro Ala Thr Leu Val Gln Pro Val
                20                  25                  30

Gly Ser Pro Leu Ser Leu Glu Cys Thr Val Glu Gly Thr Ser Asn Pro
            35                  40                  45

Asn Leu Tyr Trp Tyr Arg Gln Ala Ala Gly Arg Gly Leu Gln Leu Leu
        50                  55                  60

Phe Tyr Ser Val Gly Ile Gly Gln Ile Ser Ser Glu Val Pro Gln Asn
65                  70                  75                  80

Leu Ser Ala Ser Arg Pro Gln Asp Arg Gln Phe Ile Leu Ser Ser Lys
                85                  90                  95

Lys Leu Leu Leu Ser Asp Ser Gly Phe Tyr Leu Cys Ala Trp Ser Gly
            100                 105                 110

Leu Val Ala Glu Gln Phe Phe Gly Pro Gly Thr Arg Leu Thr Val Leu
        115                 120                 125

Glu Asp Leu Lys Asn Val Phe Pro Pro Glu Val Ala Val Phe Glu Pro
130                 135                 140

Ser Glu Ala Glu Ile Ser His Thr Gln Lys Ala Thr Leu Val Cys Leu
145                 150                 155                 160

Ala Thr Gly Phe Tyr Pro Asp His Val Glu Leu Ser Trp Trp Val Asn
                165                 170                 175

Gly Lys Glu Val His Ser Gly Val Ser Thr Asp Pro Gln Pro Leu Lys
            180                 185                 190

Glu Gln Pro Ala Leu Asn Asp Ser Arg Tyr Cys Leu Ser Ser Arg Leu
        195                 200                 205

Arg Val Ser Ala Thr Phe Trp Gln Asn Pro Arg Asn His Phe Arg Cys
210                 215                 220

Gln Val Gln Phe Tyr Gly Leu Ser Glu Asn Asp Glu Trp Thr Gln Asp
225                 230                 235                 240

Arg Ala Lys Pro Val Thr Gln Ile Val Ser Ala Glu Ala Trp Gly Arg
                245                 250                 255
```

```
Ala Asp Cys Gly Phe Thr Ser Glu Ser Tyr Gln Gln Gly Val Leu Ser
            260                 265                 270

Ala Thr Ile Leu Tyr Glu Ile Leu Leu Gly Lys Ala Thr Leu Tyr Ala
            275                 280                 285

Val Leu Val Ser Ala Leu Val Leu Met Ala Met Val Lys Arg Lys Asp
        290                 295                 300

Ser Arg Gly
305
```

<210> SEQ ID NO 121
<211> LENGTH: 6
<212> TYPE: PRT
<213> ORGANISM: Homo sapiens

<400> SEQUENCE: 121

```
Asp Ser Ala Ile Tyr Asn
1               5
```

<210> SEQ ID NO 122
<211> LENGTH: 3
<212> TYPE: PRT
<213> ORGANISM: Homo sapiens

<400> SEQUENCE: 122

```
Ile Gln Ser
1
```

<210> SEQ ID NO 123
<211> LENGTH: 15
<212> TYPE: PRT
<213> ORGANISM: Homo sapiens

<400> SEQUENCE: 123

```
Cys Ala Val Arg Pro Thr Ser Gly Gly Ser Tyr Ile Pro Thr Phe
1               5                   10                  15
```

<210> SEQ ID NO 124
<211> LENGTH: 133
<212> TYPE: PRT
<213> ORGANISM: Homo sapiens

<400> SEQUENCE: 124

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro
    130
```

<210> SEQ ID NO 125
<211> LENGTH: 141
<212> TYPE: PRT
<213> ORGANISM: Homo sapiens

<400> SEQUENCE: 125

```
Tyr Ile Gln Asn Pro Asp Pro Ala Val Tyr Gln Leu Arg Asp Ser Lys
1               5                   10                  15

Ser Ser Asp Lys Ser Val Cys Leu Phe Thr Asp Phe Asp Ser Gln Thr
            20                  25                  30

Asn Val Ser Gln Ser Lys Asp Ser Asp Val Tyr Ile Thr Asp Lys Thr
        35                  40                  45

Val Leu Asp Met Arg Ser Met Asp Phe Lys Ser Asn Ser Ala Val Ala
    50                  55                  60

Trp Ser Asn Lys Ser Asp Phe Ala Cys Ala Asn Ala Phe Asn Asn Ser
65                  70                  75                  80

Ile Ile Pro Glu Asp Thr Phe Phe Pro Ser Pro Glu Ser Ser Cys Asp
                85                  90                  95

Val Lys Leu Val Glu Lys Ser Phe Glu Thr Asp Thr Asn Leu Asn Phe
            100                 105                 110

Gln Asn Leu Ser Val Ile Gly Phe Arg Ile Leu Leu Leu Lys Val Ala
        115                 120                 125

Gly Phe Asn Leu Leu Met Thr Leu Arg Leu Trp Ser Ser
    130                 135                 140
```

<210> SEQ ID NO 126
<211> LENGTH: 274
<212> TYPE: PRT
<213> ORGANISM: Homo sapiens

<400> SEQUENCE: 126

```
Met Glu Thr Leu Leu Gly Leu Leu Ile Leu Trp Leu Gln Leu Gln Trp
1               5                   10                  15

Val Ser Ser Lys Gln Glu Val Thr Gln Ile Pro Ala Ala Leu Ser Val
            20                  25                  30

Pro Glu Gly Glu Asn Leu Val Leu Asn Cys Ser Phe Thr Asp Ser Ala
        35                  40                  45

Ile Tyr Asn Leu Gln Trp Phe Arg Gln Asp Pro Gly Lys Gly Leu Thr
    50                  55                  60

Ser Leu Leu Leu Ile Gln Ser Ser Gln Arg Glu Gln Thr Ser Gly Arg
65                  70                  75                  80

Leu Asn Ala Ser Leu Asp Lys Ser Ser Gly Arg Ser Thr Leu Tyr Ile
                85                  90                  95

Ala Ala Ser Gln Pro Gly Asp Ser Ala Thr Tyr Leu Cys Ala Val Arg
            100                 105                 110

Pro Thr Ser Gly Gly Ser Tyr Ile Pro Thr Phe Gly Arg Gly Thr Ser
        115                 120                 125

Leu Ile Val His Pro Tyr Ile Gln Asn Pro Asp Pro Ala Val Tyr Gln
    130                 135                 140

Leu Arg Asp Ser Lys Ser Ser Asp Lys Ser Val Cys Leu Phe Thr Asp
145                 150                 155                 160

Phe Asp Ser Gln Thr Asn Val Ser Gln Ser Lys Asp Ser Asp Val Tyr
                165                 170                 175

Ile Thr Asp Lys Thr Val Leu Asp Met Arg Ser Met Asp Phe Lys Ser
            180                 185                 190
```

```
Asn Ser Ala Val Ala Trp Ser Asn Lys Ser Asp Phe Ala Cys Ala Asn
        195                 200                 205

Ala Phe Asn Asn Ser Ile Ile Pro Glu Asp Thr Phe Phe Pro Ser Pro
210                 215                 220

Glu Ser Ser Cys Asp Val Lys Leu Val Glu Lys Ser Phe Glu Thr Asp
225                 230                 235                 240

Thr Asn Leu Asn Phe Gln Asn Leu Ser Val Ile Gly Phe Arg Ile Leu
                245                 250                 255

Leu Leu Lys Val Ala Gly Phe Asn Leu Leu Met Thr Leu Arg Leu Trp
                260                 265                 270

Ser Ser

<210> SEQ ID NO 127
<211> LENGTH: 5
<212> TYPE: PRT
<213> ORGANISM: Homo sapiens

<400> SEQUENCE: 127

Met Asn His Glu Tyr
1               5

<210> SEQ ID NO 128
<211> LENGTH: 6
<212> TYPE: PRT
<213> ORGANISM: Homo sapiens

<400> SEQUENCE: 128

Ser Val Gly Ala Gly Ile
1               5

<210> SEQ ID NO 129
<211> LENGTH: 14
<212> TYPE: PRT
<213> ORGANISM: Homo sapiens

<400> SEQUENCE: 129

Cys Ala Ser Ser Tyr Val Gly Asn Thr Gly Glu Leu Phe Phe
1               5                   10

<210> SEQ ID NO 130
<211> LENGTH: 132
<212> TYPE: PRT
<213> ORGANISM: Homo sapiens

<400> SEQUENCE: 130

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
                20                  25                  30

Lys Thr Gly Gln Ser Met Thr Leu Gln Cys Ala Gln Asp Met Asn His
            35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
                100                 105                 110
```

Ser Tyr Val Gly Asn Thr Gly Glu Leu Phe Phe Gly Glu Gly Ser Arg
    115                 120                 125

Leu Thr Val Leu
    130

<210> SEQ ID NO 131
<211> LENGTH: 179
<212> TYPE: PRT
<213> ORGANISM: Homo sapiens

<400> SEQUENCE: 131

Glu Asp Leu Lys Asn Val Phe Pro Pro Glu Val Ala Val Phe Glu Pro
1               5                   10                  15

Ser Glu Ala Glu Ile Ser His Thr Gln Lys Ala Thr Leu Val Cys Leu
            20                  25                  30

Ala Thr Gly Phe Tyr Pro Asp His Val Glu Leu Ser Trp Trp Val Asn
        35                  40                  45

Gly Lys Glu Val His Ser Gly Val Ser Thr Asp Pro Gln Pro Leu Lys
    50                  55                  60

Glu Gln Pro Ala Leu Asn Asp Ser Arg Tyr Cys Leu Ser Ser Arg Leu
65                  70                  75                  80

Arg Val Ser Ala Thr Phe Trp Gln Asn Pro Arg Asn His Phe Arg Cys
                85                  90                  95

Gln Val Gln Phe Tyr Gly Leu Ser Glu Asn Asp Glu Trp Thr Gln Asp
            100                 105                 110

Arg Ala Lys Pro Val Thr Gln Ile Val Ser Ala Glu Ala Trp Gly Arg
        115                 120                 125

Ala Asp Cys Gly Phe Thr Ser Glu Ser Tyr Gln Gln Gly Val Leu Ser
    130                 135                 140

Ala Thr Ile Leu Tyr Glu Ile Leu Leu Gly Lys Ala Thr Leu Tyr Ala
145                 150                 155                 160

Val Leu Val Ser Ala Leu Val Leu Met Ala Met Val Lys Arg Lys Asp
                165                 170                 175

Ser Arg Gly

<210> SEQ ID NO 132
<211> LENGTH: 311
<212> TYPE: PRT
<213> ORGANISM: Homo sapiens

<400> SEQUENCE: 132

Met Ser Ile Gly Leu Leu Cys Cys Ala Ala Leu Ser Leu Leu Trp Ala
1               5                   10                  15

Gly Pro Val Asn Ala Gly Val Thr Gln Thr Pro Lys Phe Gln Val Leu
            20                  25                  30

Lys Thr Gly Gln Ser Met Thr Leu Gln Cys Ala Gln Asp Met Asn His
        35                  40                  45

Glu Tyr Met Ser Trp Tyr Arg Gln Asp Pro Gly Met Gly Leu Arg Leu
    50                  55                  60

Ile His Tyr Ser Val Gly Ala Gly Ile Thr Asp Gln Gly Glu Val Pro
65                  70                  75                  80

Asn Gly Tyr Asn Val Ser Arg Ser Thr Thr Glu Asp Phe Pro Leu Arg
                85                  90                  95

Leu Leu Ser Ala Ala Pro Ser Gln Thr Ser Val Tyr Phe Cys Ala Ser
            100                 105                 110

```
Ser Tyr Val Gly Asn Thr Gly Glu Leu Phe Phe Gly Gly Ser Arg
            115                 120                 125
Leu Thr Val Leu Glu Asp Leu Lys Asn Val Phe Pro Pro Glu Val Ala
    130                 135                 140
Val Phe Glu Pro Ser Glu Ala Glu Ile Ser His Thr Gln Lys Ala Thr
145                 150                 155                 160
Leu Val Cys Leu Ala Thr Gly Phe Tyr Pro Asp His Val Glu Leu Ser
            165                 170                 175
Trp Trp Val Asn Gly Lys Glu Val His Ser Gly Val Ser Thr Asp Pro
            180                 185                 190
Gln Pro Leu Lys Glu Gln Pro Ala Leu Asn Asp Ser Arg Tyr Cys Leu
            195                 200                 205
Ser Ser Arg Leu Arg Val Ser Ala Thr Phe Trp Gln Asn Pro Arg Asn
    210                 215                 220
His Phe Arg Cys Gln Val Gln Phe Tyr Gly Leu Ser Glu Asn Asp Glu
225                 230                 235                 240
Trp Thr Gln Asp Arg Ala Lys Pro Val Thr Gln Ile Val Ser Ala Glu
            245                 250                 255
Ala Trp Gly Arg Ala Asp Cys Gly Phe Thr Ser Glu Ser Tyr Gln Gln
            260                 265                 270
Gly Val Leu Ser Ala Thr Ile Leu Tyr Glu Ile Leu Leu Gly Lys Ala
            275                 280                 285
Thr Leu Tyr Ala Val Leu Val Ser Ala Leu Val Leu Met Ala Met Val
            290                 295                 300
Lys Arg Lys Asp Ser Arg Gly
305                 310

<210> SEQ ID NO 133
<211> LENGTH: 9
<212> TYPE: PRT
<213> ORGANISM: Homo sapiens

<400> SEQUENCE: 133

Ala Leu Ser Val Leu Arg Leu Ala Leu
1               5

<210> SEQ ID NO 134
<211> LENGTH: 9
<212> TYPE: PRT
<213> ORGANISM: Homo sapiens

<400> SEQUENCE: 134

Ala Ala Ser Val Leu Arg Leu Ala Leu
1               5

<210> SEQ ID NO 135
<211> LENGTH: 9
<212> TYPE: PRT
<213> ORGANISM: Homo sapiens

<400> SEQUENCE: 135

Ala Leu Ala Val Leu Arg Leu Ala Leu
1               5

<210> SEQ ID NO 136
<211> LENGTH: 9
<212> TYPE: PRT
<213> ORGANISM: Homo sapiens

<400> SEQUENCE: 136
```

Ala Leu Ser Ala Leu Arg Leu Ala Leu
1               5

<210> SEQ ID NO 137
<211> LENGTH: 9
<212> TYPE: PRT
<213> ORGANISM: Homo sapiens

<400> SEQUENCE: 137

Ala Leu Ser Val Ala Arg Leu Ala Leu
1               5

<210> SEQ ID NO 138
<211> LENGTH: 9
<212> TYPE: PRT
<213> ORGANISM: Homo sapiens

<400> SEQUENCE: 138

Ala Leu Ser Val Leu Ala Leu Ala Leu
1               5

<210> SEQ ID NO 139
<211> LENGTH: 9
<212> TYPE: PRT
<213> ORGANISM: Homo sapiens

<400> SEQUENCE: 139

Ala Leu Ser Val Leu Arg Ala Ala Leu
1               5

<210> SEQ ID NO 140
<211> LENGTH: 9
<212> TYPE: PRT
<213> ORGANISM: Homo sapiens

<400> SEQUENCE: 140

Ala Leu Ser Val Leu Arg Leu Ala Ala
1               5

<210> SEQ ID NO 141
<211> LENGTH: 9
<212> TYPE: PRT
<213> ORGANISM: Homo sapiens

<400> SEQUENCE: 141

Thr Leu Ser Val Leu Arg Leu Ala Leu
1               5

<210> SEQ ID NO 142
<211> LENGTH: 9
<212> TYPE: PRT
<213> ORGANISM: Homo sapiens

<400> SEQUENCE: 142

Ala Thr Ser Val Leu Arg Leu Ala Leu
1               5

<210> SEQ ID NO 143
<211> LENGTH: 9
<212> TYPE: PRT
<213> ORGANISM: Homo sapiens

<400> SEQUENCE: 143

Ala Leu Thr Val Leu Arg Leu Ala Leu 1               5

<210> SEQ ID NO 144
<211> LENGTH: 9
<212> TYPE: PRT
<213> ORGANISM: Homo sapiens

<400> SEQUENCE: 144

Ala Leu Ser Thr Leu Arg Leu Ala Leu
1               5

<210> SEQ ID NO 145
<211> LENGTH: 9
<212> TYPE: PRT
<213> ORGANISM: Homo sapiens

<400> SEQUENCE: 145

Ala Leu Ser Val Thr Arg Leu Ala Leu
1               5

<210> SEQ ID NO 146
<211> LENGTH: 9
<212> TYPE: PRT
<213> ORGANISM: Homo sapiens

<400> SEQUENCE: 146

Ala Leu Ser Val Leu Thr Leu Ala Leu
1               5

<210> SEQ ID NO 147
<211> LENGTH: 9
<212> TYPE: PRT
<213> ORGANISM: Homo sapiens

<400> SEQUENCE: 147

Ala Leu Ser Val Leu Arg Thr Ala Leu
1               5

<210> SEQ ID NO 148
<211> LENGTH: 9
<212> TYPE: PRT
<213> ORGANISM: Homo sapiens

<400> SEQUENCE: 148

Ala Leu Ser Val Leu Arg Leu Thr Leu
1               5

<210> SEQ ID NO 149
<211> LENGTH: 9
<212> TYPE: PRT
<213> ORGANISM: Homo sapiens

<400> SEQUENCE: 149

Ala Leu Ser Val Leu Arg Leu Ala Thr
1               5

<210> SEQ ID NO 150
<211> LENGTH: 9
<212> TYPE: PRT
<213> ORGANISM: Homo sapiens

<400> SEQUENCE: 150

Ala Leu Met Asn Met Lys Leu Ala Leu
1               5

<210> SEQ ID NO 151
<211> LENGTH: 9
<212> TYPE: PRT
<213> ORGANISM: Homo sapiens

<400> SEQUENCE: 151

Ala Leu Ser Asp Leu Arg Cys Asn Leu
1               5

<210> SEQ ID NO 152
<211> LENGTH: 9
<212> TYPE: PRT
<213> ORGANISM: Homo sapiens

<400> SEQUENCE: 152

Ala Leu Ser Ser Leu Ile His Ala Leu
1               5

<210> SEQ ID NO 153
<211> LENGTH: 9
<212> TYPE: PRT
<213> ORGANISM: Homo sapiens

<400> SEQUENCE: 153

Ala Leu Ser Thr Leu Ala Leu Tyr Val
1               5

<210> SEQ ID NO 154
<211> LENGTH: 9
<212> TYPE: PRT
<213> ORGANISM: Homo sapiens

<400> SEQUENCE: 154

Ala Leu Ser Val Leu Ala Asp Phe Leu
1               5

<210> SEQ ID NO 155
<211> LENGTH: 9
<212> TYPE: PRT
<213> ORGANISM: Homo sapiens

<400> SEQUENCE: 155

Ala Leu Tyr Ala Ser Arg Leu Tyr Leu
1               5

<210> SEQ ID NO 156
<211> LENGTH: 9
<212> TYPE: PRT
<213> ORGANISM: Homo sapiens

<400> SEQUENCE: 156

Gly Leu Ser Asp Leu Arg Leu Glu Leu
1               5

<210> SEQ ID NO 157
<211> LENGTH: 9
<212> TYPE: PRT
<213> ORGANISM: Homo sapiens

<400> SEQUENCE: 157

Ile Val Ser Ser Leu Arg Leu Ala Tyr
1               5

<210> SEQ ID NO 158

```
<211> LENGTH: 9
<212> TYPE: PRT
<213> ORGANISM: Homo sapiens

<400> SEQUENCE: 158

Tyr Leu Asp Val Ile Arg Leu Leu Leu
1               5

<210> SEQ ID NO 159
<211> LENGTH: 9
<212> TYPE: PRT
<213> ORGANISM: Homo sapiens

<400> SEQUENCE: 159

Ser Leu Leu Met Trp Ile Thr Gln Val
1               5
```

T CELL RECEPTORS AND IMMUNE THERAPY USING THE SAME

CROSS-REFERENCE TO RELATED APPLICATIONS

This application is a continuation of U.S. patent application Ser. No. 16/023,731, filed 29 Jun. 2018, which claims priority to 62/527,844, filed 30 Jun. 2017 and German Patent Application No. 10 2017 114 737.3, filed 30 Jun. 2017. The disclosures of the priority applications are incorporated in their entirety herein by reference.

This application is also related to PCT/EP2018/067380, filed 28 Jun. 2018, the content of which is incorporated herein by reference in its entirety.

REFERENCE TO SEQUENCE LISTING SUBMITTED AS A COMPLIANT ASCII TEXT FILE (.TXT)

Pursuant to the EFS-Web legal framework and 37 CFR §§ 1.821-825 (see MPEP § 2442.03(a)), a Sequence Listing in the form of an ASCII-compliant text file (entitled "3000058-010002_Sequence_Listing_ST25.txt" created on 9 Apr. 2019, and 127,719 bytes in size) is submitted concurrently with the instant application, and the entire contents of the Sequence Listing are incorporated herein by reference.

FIELD OF THE INVENTION

The present invention pertains to antigen recognizing constructs against tumor associated antigens (TAA), in particular the TAA Serine protease inhibitor Kazal-type 2 (SPINK2). The invention in particular provides novel T cell receptor (TCR) based molecules which are selective and specific for the tumor expressed antigen of the invention. The TCR of the invention, and SPINK2 binding fragments derived therefrom, are of use for the diagnosis, treatment and prevention of SPINK2 expressing cancerous diseases. Further provided are nucleic acids encoding the antigen recognizing constructs of the invention, vectors comprising these nucleic acids, recombinant cells expressing the antigen recognizing constructs and pharmaceutical compositions comprising the compounds of the invention.

DESCRIPTION OF RELATED ART

Serine protease inhibitor Kazal-type 2 (SPINK2), is also known as acrosin-trypsin inhibitor, and is a protein that in humans is encoded by the SPINK2 gene. The encoded protein acts as a trypsin and acrosin inhibitor in the genital tract and is localized in the spermatozoa. The protein has been associated with the progression of lymphomas. Alternative splicing results in multiple transcript variants.

T-cell based immunotherapy targets represent peptide epitopes derived from tumor-associated or tumor-specific proteins, which are presented by molecules of the major histocompatibility complex (MHC). These tumor associated antigens (TAAs) can be peptides derived from all protein classes, such as enzymes, receptors, transcription factors, etc. which are expressed and, as compared to unaltered cells of the same origin, usually up-regulated in cells of the respective tumor.

Specific elements of the cellular immune response are capable of specifically recognizing and destroying tumor cells. The isolation of T-cells from tumor-infiltrating cell populations or from peripheral blood suggests that such cells play an important role in natural immune defense against cancer. CD8-positive T-cells in particular, which recognize class I molecules of the major histocompatibility complex (MHC)-bearing peptides of usually 8 to 10 amino acid residues derived from proteins or defective ribosomal products (DRiPs) located in the cytosol, play an important role in this response. The MHC-molecules of the human are also designated as human leukocyte-antigens (HLA).

There are two classes of MHC-molecules, MHC class I and MHC class II. Complexes of peptide and MHC class I are recognized by CD8-positive T-cells bearing the appropriate T-cell receptor (TCR), whereas complexes of peptide and MHC class II molecules are recognized by CD4-positive-helper-T-cells bearing the appropriate TCR. Since both types of response, CD8 and CD4 dependent, contribute jointly and synergistically to the anti-tumor effect, the identification and characterization of tumor-associated antigens and corresponding T cell receptors is important in the development of cancer immunotherapies such as vaccines and cell therapies.

In the MHC class I dependent immune reaction, peptides not only have to be able to bind to certain MHC class I molecules expressed by tumor cells, they subsequently also have to be recognized by T-cells bearing specific T-cell receptors (TCR). Therefore, TAAs are a starting point for the development of a T-cell based therapy including but not limited to tumor vaccines and cell therapies.

Approximately 90 percent of peripheral blood T cells express a TCR consisting of an α polypeptide and a β polypeptide. A small percentage of T cells (about 5% of total T cells) have been shown to express a TCR consisting of a γ polypeptide and a δ polypeptide. γδ T cells are found at their highest abundance in the gut mucosa, within a population of lymphocytes known as intraepithelial lymphocytes (IELs). The antigenic molecules that activate γδ T cells are still widely unknown. However, γδ T cells are not MHC restricted and seem to be able to recognize whole proteins rather than requiring peptides to be presented by MHC molecules on antigen presenting cells, although some recognize MHC class IB molecules. Human Vγ9/Vδ2 T cells, which constitute the major γδ T cell population in peripheral blood, are unique in that they specifically and rapidly respond to a small non-peptidic microbial metabolite, HMB-PP, an isopentenyl pyrophosphate precursor. Estimates of the percentages of T cells that may be found in peripheral blood from healthy donors are as follows: CD3+=70.78%±4.71; CD3+CD4=38.97%±5.66; CD3+CD8=28.955%±7.43; CD3+CD56+=5 0.22%±1.74; CD3−CD56+=10.305%±4.7; CD3+CD45RA=45.00%±7.19; CD3+CD45RO+=27.21%±7.34.

The chains of the T cell antigen receptor of a T cell clone are each composed of a unique combination of domains designated variable (V), [diversity (D),] joining (J), and constant (C). In each T cell clone, the combination of V, D and J domains of both the alpha and the beta chains or of both the delta and gamma chains participates in antigen recognition in a manner which is uniquely characteristic of that T cell clone and defines a unique binding site, also known as the idiotype of the T cell clone. In contrast, the C domain does not participate in antigen binding.

A TCR is a heterodimeric cell surface protein of the immunoglobulin super-family, which is associated with invariant proteins of the CD3 complex involved in mediating signal transduction. TCRs exist in αβ and γδ forms, which are structurally similar but have quite distinct anatomical locations and probably functions. The extracellular portion of native heterodimeric αβTCR and γδTCR each contain two polypeptides, each of which has a membrane-proximal constant domain, and a membrane-distal variable domain. Each of the constant and variable domains includes an intra-chain disulfide bond. The variable domains contain the highly polymorphic loops analogous to the complementarity determining regions (CDRs) of antibodies. The use of TCR gene therapy overcomes a number of current hurdles. It allows equipping patients' own T cells with desired specificities and generation of sufficient numbers of T cells in a short period of time, avoiding their exhaustion. The TCR will be transduced into central memory T cells or T cells with stem cell characteristics, which may ensure better persistence and function upon transfer. TCR-engineered T cells will be infused into cancer patients rendered lymphopenic by chemotherapy or irradiation, allowing efficient engraftment but inhibiting immune suppression.

While advances have been made in the development of molecular-targeting drugs for cancer therapy, there remains a need in the art to develop new anti-cancer agents that specifically target molecules highly specific to cancer cells. The present description addresses that need by providing novel SPINK2-001 TCRs, respective recombinant TCR constructs, nucleic acids, vectors and host cells that specifically bind TAA epitope(s) as disclosed; and methods of using such molecules in the treatment of cancer. The term TAA in context of the invention relates in particular to the protein SPINK2 and even more preferably to the epitope SPINK2-001 as also disclosed herein elsewhere.

SUMMARY

Antigen Recognizing Constructs

The object of the invention is solved in a first aspect by an antigen recognizing construct comprising at least one complementary determining region (CDR) 3 having at least 50%, 60%, 70%, 80%, 90%, 95%, 98%, 99%, or preferably 100% sequence identity to an amino acid sequence selected from SEQ ID NOs: 3, 9, 15, 21, 27, 33, 39, 45, 51, 57, 63, 69, 75, 81, 87, 93, 99, 105, 111, and 117.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF A PREFERRED EMBODIMENT

Figure 1:
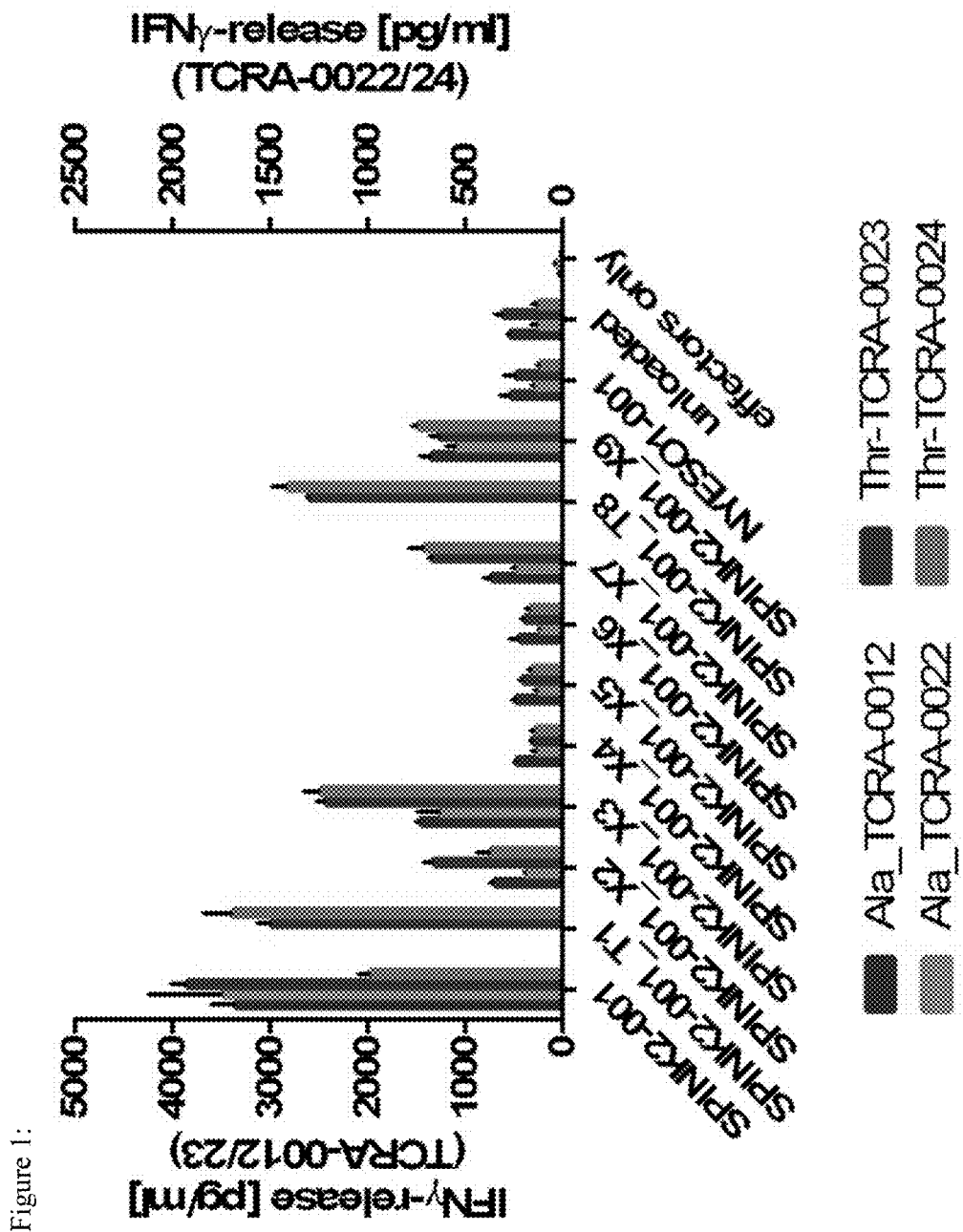
FIGS. 1-33 depict embodiments of the disclosure as described herein.

In some embodiments the antigen recognizing construct of the invention specifically binds to a TAA-peptide-HLA molecule complex, wherein the TAA peptide comprises, or alternatively consists of, a variant of the TAA which is at least 66%, preferably at least 77%, and more preferably at least 88% homologous (preferably at least 77% or at least 88% identical) to the amino acid sequence of the TAA of the invention, wherein said variant binds to an HLA class I or class II molecule and/or induces T-cells cross-reacting with said peptide, or a pharmaceutically acceptable salt thereof, wherein said peptide is not the underlying full-length polypeptide.

As used herein, the terms "identical" or percent "identity", when used anywhere herein in the context of two or more nucleic acid or protein/polypeptide sequences, refer to two or more sequences or subsequences that are the same or have (or have at least) a specified percentage of amino acid residues or nucleotides that are the same (i.e., at, or at least, about 60% identity, preferably at, or at least, 65%, 70%, 75%, 80%, 85%, 90%, 91%, 92%, 93% or 94%, identity, and more preferably at, or at least, about 95%, 96%, 97%, 98%, 99%, or higher identity over a specified region—preferably over their full length sequences—, when compared and aligned for maximum correspondence over the comparison window or designated region) as measured using a sequence comparison algorithms, or by manual alignment and visual inspection (see, e.g., NCBI web site). In a particular embodiment, for example when comparing the protein or nucleic acid sequence of an antigen recognizing construct of the invention to another protein/gene, the percentage identity can be determined by the Blast searches supported at the NCBI web site; in particular for amino acid identity, those using BLASTP with the following parameters: Expected threshold 10; Word size: 6; Matrix: BLOSUM62; Gap Costs: Existence: 11, Extension: 1; Neighboring words threshold: 11; Compositional adjustments: Conditional compositional score matrix adjustment.

In the context of the present invention it shall be understood that any embodiments referred to as "comprising" certain features of the invention, shall be understood to include in some more preferred embodiments the more restricted description of "consisting of" or "consisting essentially of" the very same features of the present invention.

In another additional or alternative embodiment, the antigen recognizing construct may further comprise a CDR1 and/or a CDR2 domain sequence. Within the variable domain, CDR1 and CDR2 are found in the variable (V) region of a polypeptide chain, and CDR3 includes some of V, all of diversity (D) and joining (J) regions. CDR3 is the most variable and is the main CDR responsible for specifically and selectively recognizing an antigen. CDR1 and CDR2 sequences may be selected from a CDR sequence of a human variable chain allele.

Native alpha-beta heterodimeric TCRs have an alpha chain and a beta chain. Each chain comprises variable, joining and constant regions, and the beta chain also usually contains a short diversity region between the variable and joining regions, but this diversity region is often considered as part of the joining region. Each variable region comprises three CDRs (Complementarity Determining Regions) embedded in a framework sequence, one being the hypervariable region named CDR3. There are several types of alpha chain variable (Vα) regions and several types of beta chain variable (Vβ) regions distinguished by their framework, CDR1 and CDR2 sequences, and by a partly defined CDR3 sequence. The Vα types are referred to in IMGT nomenclature by a unique TRAY number, Vβ types are referred to by a unique TRBV number. For more information on immunoglobulin antibody and TCR genes see the international ImMunoGeneTics information System®, Lefranc M-P et al (Nucleic Acids Res. 2015 January; 43(Database issue):D413-22; and http://www.imgt.org/).

Therefore, in one additional or alternative embodiment the antigen recognizing construct of the invention comprises CDR1, CDR2 and CDR3 sequences in a combination as provided in table 1 herein below, which display the respective variable chain allele together with the CDR3 sequence. Therefore, preferred are antigen recognizing constructs of the invention which comprise at least one, preferably, all three CDR sequences CDR1, CDR2 and CDR3. Preferably, an antigen recognizing construct of the invention comprises the respective CDR1 to CDR3 of one individual herein disclosed TCR variable region of the invention (see table 1 herein below and the example section).

The term "specificity" or "antigen specificity" or "specific for" a given antigen, as used herein means that the antigen recognizing construct can specifically bind to said antigen, preferably a TAA antigen, more preferably with high avidity, when said antigen is presented by HLA, preferably by HLA-A*02. For example, a TCR, as antigen recognizing construct, may be considered to have "antigenic specificity" for the TAA, if T cells expressing the TCR and contacted with a TAA presenting HLA secrete at least about 200 pg/ml or more (e.g., 250 pg/ml or more, 300 pg/ml or more, 400 pg/ml or more, 500 pg/ml or more, 600 pg/ml or more, 700 pg/ml or more, 1000 pg ml or more, 2,000 pg/ml or more, 2,500 pg/ml or more, 5,000 pg/ml or more) of interferon γ (IFN-γ) upon co-culture with target cells pulsed with a low concentration of a TAA antigen, such as the TAA epitopes and antigens provided herein below (e.g., about $10^{-11}$ mol/l, $10^{-10}$ mol/l, $10^{-9}$ mol/l, $10^{-8}$ mol/l, $10^{-7}$ mol/l, $10^{-6}$ mol/l, $10^{-5}$ mol/l). Alternatively, or additionally, a TCR may be considered to have "antigenic specificity" for the TAA, if T cells expressing the TCR secrete at least twice as much IFN-γ as the untransduced background level of IFN-γ upon co-culture with target cells pulsed with a low concentration of the TAA antigens. Such a "specificity" as described above can—for example—be analyzed with an ELISA.

In one alternative or additional embodiment of the invention, the antigen recognizing construct selectively binds to a TAA derived antigenic peptide; preferably wherein the TAA antigenic peptide is a protein epitope or peptide having an amino acid sequence shown in table 2 below, in particular the antigenic peptide is the SPINK2-001 peptide (SEQ ID NO: 133), or a variant thereof, wherein the variant is an amino acid deletion, addition, insertion or substitution of not more than three, preferably two and most preferably not more than one amino acid position. Preferred variants of SPINK2-001 are shown in table 2 below.

The term "selectivity" or "selective recognizing/binding" is understood to refer to the property of an antigen recognizing construct, such as a TCR or antibody, to selectively recognize or bind to preferably only one specific epitope and preferably shows no or substantially no cross-reactivity to another epitope. Preferably "selectivity" or "selective recognizing/binding" means that the antigen recognizing construct (e.g. a TCR) selectively recognizes or binds to preferably only one specific epitope and preferably shows no or substantially no cross-reactivity to another epitope, wherein said epitope is unique for one protein, such that the antigen recognizing construct shows no or substantially no cross-reactivity to another epitope and another protein.

The antigen recognizing construct according to the invention is preferably selected from an antibody, or derivative or fragment thereof, or a T cell receptor (TCR), or derivative or fragment thereof. A derivative or fragment of an antibody or TCR of the invention shall preferably retain the antigen binding/recognizing ability of the parent molecule, in particular its specificity and/or selectivity as explained above. Such binding functionality may be retained by the presence of a CDR3 region as defined herein.

In an embodiment of the invention, the inventive TCRs are able to recognize TAA antigens in a major histocompatibility complex (MHC) class I-dependent manner "MHC class I-dependent manner," as used herein, means that the TCR elicits an immune response upon binding to TAA antigens within the context of an MHC class I molecule. The MHC class I molecule can be any MHC class I molecule known in the art, e.g., HLA-A molecules. In a preferred embodiment of the invention, the MHC class I molecule is an HLA-A*02 molecule.

In an aspect, the TCR-elicited immune response or T-cell response may refer to the proliferation and activation of effector functions induced by a peptide in vitro or in vivo. For MHC class I restricted cytotoxic T cells, for example, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, for example, granzymes or perforins induced by peptide, or degranulation.

In an aspect, the TCR-elicited immune response or T-cell response may refer to the proliferation and activation of effector functions induced by a peptide in vitro or in vivo. For MHC class I restricted cytotoxic T cells, for example, effector functions may be lysis of peptide-pulsed, peptide-precursor pulsed or naturally peptide-presenting target cells, secretion of cytokines, preferably Interferon-gamma, TNF-alpha, or IL-2 induced by peptide, secretion of effector molecules, for example, granzymes or perforins induced by peptide, or degranulation.

The invention provides both single chain antigen recognizing construct and double chain recognizing constructs.

In an embodiment, the TCR alpha variable domain has at least one mutation relative to a TCR alpha domain shown in Table 1; and/or the TCR beta variable domain has at least one mutation relative to a TCR alpha domain shown in Table 1. In an embodiment, a TCR comprising at least one mutation in the TCR alpha variable domain and/or TCR beta variable domain has a binding affinity for, and/or a binding half-life for, a TAA peptide-HLA molecule complex, which is at least double that of a TCR comprising the unmutated TCR alpha domain and/or unmutated TCR beta variable domain.

The TCR alpha chains of the present description may further comprise a TCR alpha transmembrane domain and/or a TCR alpha intracellular domain. The TCR beta chains of the present description may further comprise a TCR beta transmembrane domain and/or a TCR beta intracellular domain.

The invention in particular provides a TCR as antigen recognizing construct, or fragment or derivative thereof. The TCR preferably is of human, which is understood as being generated from a human TCR locus and therefore comprising human TCR sequences. Furthermore, the TCR of the invention may be characterized in that it is of human origin and specifically recognizes a TAA antigen of the invention.

Another embodiment of the invention additionally or alternatively provides the antigen recognizing construct described above, which induces an immune response, preferably wherein the immune response is characterized by an increase in interferon (IFN) γ levels.

TCRs of the invention may be provided as single chain α or β, or γ and δ, molecules, or alternatively as double chain constructs composed of both the α and β chain, or γ and δ chain. Furthermore, if in context of the present invention any one, two or all CDR regions of a given TCR as described in the present invention, is grafted from one TCR chain type into another, it is in some embodiments preferred that such CDR originally derived from an α chain could be grafted into a γ or δ chain, and/or such CDR of a β chain could be grafted into a γ or δ chain framework. Thereby it is possible if starting with CDR sequences of an α/β TCR, one can obtain a γ/δ TCR, however, in two ways. One is by grafting the CDR from a into a γ framework and from 13 into a δ framework. A second, as described above, by grafting the CDR from an α into a δ framework, and from β into a γ framework. The person of skill is aware of the similarity of the framework regions between the α/β, and γ/δ TCR chains and thus, such embodiments are encompassed by the present invention (see also Lefranc M-P et al, Nucleic Acids Res. 2015 January; 43 (Database issue): D413-22; and http://www.imgt.org/).

The antigen recognizing construct of the invention may comprise a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID NOs: 3, 15, 27, 39, 51, 63, 75, 87, 99, and 111, and/or wherein the TCR or δ chain comprises a CDR3 having at least 50%, 60%, 70%, 80%, 90%, 95%, 98%, 99%, or 100% sequence identity to an amino acid sequence selected from SEQ ID NOs: 9, 21, 33, 45, 57, 69, 81, 93, 105, and 117.

Most preferably, in some additional embodiments, wherein the disclosure refers to antigen recognizing constructs comprising any one, two or all of the CDR1 to CDR3 regions of the herein disclosed TCR chains (see Table 1), such antigen recognizing constructs may be preferred, which comprise the respective CDR sequence of the invention with not more than three, two, and preferably only one, modified amino acid residues. A modified amino acid residue may be selected from an amino acid insertion, deletion or substitution. Most preferred is that the three, two, preferably only one modified amino acid residue is the first or last amino acid residue of the respective CDR sequence. If the modification is a substitution then it is preferable in some embodiments that the substitution is a conservative amino acid substitution.

If the antigen recognizing construct of the invention is composed of at least two amino acid chains, such as a double chain TCR, or antigen binding fragment thereof, the antigen recognizing construct may comprises in a first polypeptide chain the amino acid sequence according to SEQ ID NO: 3, and in a second polypeptide chain the amino acid sequence according to SEQ ID NO: 9; or in a first polypeptide chain the amino acid sequence according to SEQ ID NO: 15, and in a second polypeptide chain the amino acid sequence according to SEQ ID NO: 21; or in a first polypeptide chain the amino acid sequence according to SEQ ID NO: 27, and in a second polypeptide chain the amino acid sequence according to SEQ ID NO: 33; or in a first polypeptide chain the amino acid sequence according to SEQ ID NO: 39, and in a second polypeptide chain the amino acid sequence according to SEQ ID NO: 45; or in a first polypeptide chain the amino acid sequence according to SEQ ID NO: 51, and in a second polypeptide chain the amino acid sequence according to SEQ ID NO: 57; or in a first polypeptide chain the amino acid sequence according to SEQ ID NO: 63, and in a second polypeptide chain the amino acid sequence according to SEQ ID NO: 69; or in a first polypeptide chain the amino acid sequence according to SEQ ID NO: 75, and in a second polypeptide chain the amino acid sequence according to SEQ ID NO: 81; or in a first polypeptide chain the amino acid sequence according to SEQ ID NO: 87, and in a second polypeptide chain the amino acid sequence according to SEQ ID NO: 93; or in a first polypeptide chain the amino acid sequence according to SEQ ID NO: 99, and in a second polypeptide chain the amino acid sequence according to SEQ ID NO: 105; or in a first polypeptide chain the amino acid sequence according to SEQ ID NO: 111, and in a second polypeptide chain the amino acid sequence according to SEQ ID NO: 117. Any one of the aforementioned double chain TCR, or antigen binding fragments thereof, are preferred TCR of the present invention. In some embodiments, the CDR3 of the double chain TCR of the invention may be mutated. Mutations of the CDR3 sequences as provided above preferably include a substitution, deletion, addition, or insertion of not more than three, preferably two, and most preferably not more than one amino acid residue. In some embodiments, the first polypeptide chain may be a TCR α or γ chain, and the second polypeptide chain may be a TCR β or δ chain. Preferred is the combination of an αβ or γδ TCR.

The TCR, or the antigen binding fragment thereof, is in some embodiments composed of a TCR α and a TCR β chain, or γ and δ chain. Such a double chain TCR comprises within each chain variable regions, and the variable regions each comprise one CDR1, one CDR2 and one CDR3 sequence. The TCRs comprises the CDR1 to CDR3 sequences as comprised in the variable chain amino acid sequence of SEQ ID NOs: 4 and 10; or 16 and 22; or 28 and 34; or 40 and 46; or 52 and 58; or 64 and 70; or 76 and 82; or 88 and 94; or 100 and 106; or 112 and 118.

Some embodiments of the invention pertain to a TCR, or a fragment thereof, composed of a TCR α and a TCR β chain, wherein said TCR comprises the variable region sequences having at least 50%, 60%, 70%, 80%, 90%, 95%, 98%, 99%, or preferably 100% sequence identity to the amino acid sequence selected from the α and β chain according to SEQ ID NOs: 4 and 10; or 16 and 22; or 28 and 34; or 40 and 46; or 52 and 58; or 64 and 70; or 76 and 82; or 88 and 94; or 100 and 106; or 112 and 118.

The inventive TCRs may further comprise a constant region derived from any suitable species, such as any mammal, e.g., human, rat, monkey, rabbit, donkey, or mouse. In an embodiment of the invention, the inventive TCRs further comprise a human constant region. In some preferred embodiments, the constant region of the TCR of the invention may be slightly modified, for example, by the introduction of heterologous sequences, preferably mouse sequences, which may increase TCR expression and stability.

The inventive TCRs may further comprise modified T cell receptor (TCR) α or β chains, or heterodimers comprising the same, wherein in the variable domain of said modified α or β chain, an amino acid at position 44 according to the IMGT numbering is substituted with another suitable amino acid, in order to improve pairing of desired chains. According to one embodiment of said recombinant T cell receptor (TCR) heterodimer, in at least the α or β chain, the amino acid as present at position 44 in the variable domain is substituted by one amino acid selected from the group consisting of Q, R, D, E, K, L, W, and V.

According to another embodiment, the inventive TCRs may further include one of the preferred substitution pairs selected from the following lists:

αQ44D/βQ44R; αQ44R/βQ44D; αQ44E/βQ44K;
αQ44K/βQ44E; αQ44D/βQ44K; αQ44K/βQ44D;
αQ44E/βQ44R; αQ44R/βQ44E; αQ44L/βQ44W;
αQ44W/βQ44L; αQ44V/βQ44W; and αQ44W/βQ44V;

αW44D/βQ44R; αW44R/βQ44D; αW44E/βQ44K;
αW44K/βQ44E; αW44D/βQ44K; αW44K/βQ44D;
αW44E/βQ44R; αW44R/βQ44E; αW44L/βQ44W;
αW44/βQ44L; αW44V/βQ44W; and αW44/βQ44V;

αH44D/βQ44R; αH44R/βQ44D; αH44E/βQ44K;
αH44K/βQ44E; αH44D/βQ44K; αH44K/βQ44D;

αH44E/βQ44R; αH44R/βQ44E; αH44L/βQ44W; αH44W/βQ44L; αH44V/βQ44W; and αH44W/βQ44V;

αK44D/βQ44R; αK44R/βQ44D; αK44E/βQ44K; αK44/βQ44E; αK44D/βQ44K; αK44/βQ44D; αK44E/βQ44R; αK44R/βQ44E; αK44L/βQ44W; αK44W/βQ44L; αK44V/βQ44W; and αK44W/βQ44V;

αE44D/βQ44R; αE44R/βQ44D; αE44/βQ44K; αE44K/βQ44E; αE44D/βQ44K; αE44K/βQ44D; αE44/βQ44R; αE44R/βQ44E; αE44L/βQ44W; αE44W/βQ44L; αE44V/βQ44W; and αE44W/βQ44V;

αQ44D/βR44; αQ44R/βR44D; αQ44E/βR44K; αQ44K/βR44E; αQ44D/βR44K; αQ44K/βR44D; αQ44E/βR44; αQ44R/βR44E; αQ44L/βR44W; αQ44W/βR44L; αQ44V/βR44W; and αQ44W/βR44V;

αW44D/βR44; αW44R/βR44D; αW44E/βR44K; αW44K/βR44E; αW44D/βR44K; αW44K/βR44D; αW44E/βR44; αW44R/βR44E; αW44L/βR44W; αW44/βR44L; αW44V/βR44W; and αW44/βR44V;

αH44D/βR44; αH44R/βR44D; αH44E/βR44K; αH44K/βR44E; αH44D/βR44K; αH44K/βR44D; αH44E/βR44; αH44R/βR44E; αH44L/βR44W; αH44W/βR44L; αH44V/βR44W; and αH44W/βR44V;

αK44D/βR44; αK44R/βR44D; αK44E/βR44K; αK44/βR44E; αK44D/βR44K; αK44/βR44D; αK44E/βR44; αK44R/βR44E; αK44L/βR44W; αK44W/βR44L; αK44V/βR44W; and αK44W/βR44V;

αE44D/βR44; αE44R/βR44D; αE44/βR44K; αE44K/βR44E; αE44D/βR44K; αE44K/βR44D; αE44R/βR44E; αE44L/βR44W; αE44W/βR44L; αE44V/βR44W; and αE44W/βR44V.

In the above, e.g. "αQ44R/βQ44D" shall mean, for example, that, in the variable domain of the α chain, Q44 is substituted by R, while in the variable domain of the β chain, Q44 is substituted by D.

Some embodiments of the invention pertain to a TCR, or a fragment thereof, composed of a TCR α and a TCR β chain, wherein said TCR comprises the constant region having at least 50%, 60%, 70%, 80%, 90%, 95%, 98%, 99%, or preferably 100% sequence identity to an amino acid sequence selected from of the α and β chain according to SEQ ID NOs: 5 and 11; or 17 and 23; or 29 and 35; or 41 and 47; or 53 and 59; or 65 and 71; or 77 and 83; or 89 and 95; or 101 and 107; or 113 and 119.

The TCR α or γ chain of the invention may further comprise a CDR1 having at least 50%, 60%, 70%, 80%, 90%, 95%, 98%, 99%, or 100% sequence identity to an amino acid sequence selected from SEQ ID NOs: 1, 13, 25, 37, 49, 61, 73, 85, 97, and 109; and/or a CDR2 having at least 50%, 60%, 70%, 80%, 90%, 95%, 98%, 99%, or 100% sequence identity to an amino acid sequence selected from SEQ ID NOs: 2, 14, 26, 38, 50, 62, 74, 86, 98, and 110.

According to the invention the TCR β or δ chain may further comprise a CDR1 having at least 50%, 60%, 70%, 80%, 90%, 95%, 98%, 99%, or 100% sequence identity to an amino acid sequence selected from SEQ ID NOs: 7, 19, 31, 43, 55, 67, 79, 91, 103, and 115; and/or a CDR2 having at least 50%, 60%, 70%, 80%, 90%, 95%, 98%, 99%, or 100% sequence identity to an amino acid sequence selected from SEQ ID NOs: 8, 20, 32, 44, 56, 68, 80, 92, 104, and 116.

The antigen recognizing construct may in a further embodiment comprise a binding fragment of a TCR, and wherein said binding fragment comprises in one chain CDR1 to CDR3, optionally selected from the CDR1 to CDR3 sequences having the amino acid sequences of SEQ ID NOs: 1, 2, 3; or 7, 8, 9; or 13, 14, 15; or 19, 20, 21; or 25, 26, 27; or 31, 32, 33; or 37, 38, 39; or 43, 44, 45; or 49, 50, 51; or 55, 56, 57; or 61, 62, 63; or 67, 68, 69; or 73, 74, 75; or 79, 80, 81; or 85, 86, 87; or 91, 92, 93; or 97, 98, 99; or 103, 104, 105; or 109, 110, 111; or 115, 116, 117.

In further embodiments of the invention the antigen recognizing construct as described herein elsewhere is a TCR, or a fragment thereof, composed of at least one TCR α and one TCR β chain sequence, wherein said TCR α chain sequence comprises the CDR1 to CDR3 sequences having the amino acid sequences of SEQ ID NOs: 1 to 3, and said TCR β chain sequence comprises the CDR1 to CDR3 sequences having the amino acid sequences of SEQ ID NOs: 7 to 9; or wherein said TCR α chain sequence comprises the CDR1 to CDR3 sequences having the amino acid sequences of SEQ ID NOs: 13 to 15, and said TCR β chain sequence comprises the CDR1 to CDR3 sequences having the amino acid sequences of SEQ ID NOs: 19 to 21; or wherein said TCR α chain sequence comprises the CDR1 to CDR3 sequences having the amino acid sequences of SEQ ID NOs: 25 to 27, and said TCR β chain sequence comprises the CDR1 to CDR3 sequences having the amino acid sequences of SEQ ID NOs: 31 to 33; or wherein said TCR α chain sequence comprises the CDR1 to CDR3 sequences having the amino acid sequences of SEQ ID NOs: 37 to 39, and said TCR β chain sequence comprises the CDR1 to CDR3 sequences having the amino acid sequences of SEQ ID NOs: 43 to 45; or wherein said TCR α chain sequence comprises the CDR1 to CDR3 sequences having the amino acid sequences of SEQ ID NOs: 49 to 51, and said TCR β chain sequence comprises the CDR1 to CDR3 sequences having the amino acid sequences of SEQ ID NOs: 55 to 57; or wherein said TCR α chain sequence comprises the CDR1 to CDR3 sequences having the amino acid sequences of SEQ ID NOs: 61 to 63, and said TCR β chain sequence comprises the CDR1 to CDR3 sequences having the amino acid sequences of SEQ ID NOs: 67 to 69; or wherein said TCR α chain sequence comprises the CDR1 to CDR3 sequences having the amino acid sequences of SEQ ID NOs: 73 to 75, and said TCR β chain sequence comprises the CDR1 to CDR3 sequences having the amino acid sequences of SEQ ID NOs: 79 to 81; or wherein said TCR α chain sequence comprises the CDR1 to CDR3 sequences having the amino acid sequences of SEQ ID NOs: 85 to 87, and said TCR β chain sequence comprises the CDR1 to CDR3 sequences having the amino acid sequences of SEQ ID NOs: 91 to 93; or wherein said TCR α chain sequence comprises the CDR1 to CDR3 sequences having the amino acid sequences of SEQ ID NOs: 97 to 99, and said TCR β chain sequence comprises the CDR1 to CDR3 sequences having the amino acid sequences of SEQ ID NOs: 103 to 105; or wherein said TCR α chain sequence comprises the CDR1 to CDR3 sequences having the amino acid sequences of SEQ ID NOs: 109 to 111, and said TCR β chain sequence comprises the CDR1 to CDR3 sequences having the amino acid sequences of SEQ ID NOs: 115 to 117.

In further embodiments of the invention the antigen recognizing construct as described herein before is a TCR, or a fragment thereof, comprising at least one TCR α and one TCR β chain sequence, wherein said TCR α chain sequence comprises a variable region sequence having the amino acid sequence of SEQ ID NO: 4, and wherein said TCR β chain sequence comprises a variable region sequence having the amino acid sequence of SEQ ID NO: 10; or wherein said TCR α chain sequence comprises a variable region sequence having the amino acid sequence of SEQ ID NO: 16, and wherein said TCR β chain sequence comprises a variable region sequence having the amino acid sequence of SEQ ID NO: 22; or wherein said TCR α chain sequence comprises a variable region sequence having the amino acid sequence of SEQ ID NO: 28, and wherein said TCR β chain sequence comprises a variable region sequence having the amino acid sequence of SEQ ID NO: 34; or wherein said TCR α chain sequence comprises a variable region sequence having the amino acid sequence of SEQ ID NO: 40, and wherein said TCR β chain sequence comprises a variable region sequence having the amino acid sequence of SEQ ID NO: 46; or wherein said TCR α chain sequence comprises a variable region sequence having the amino acid sequence of SEQ ID NO: 52, and wherein said TCR β chain sequence comprises a variable region sequence having the amino acid sequence of SEQ ID NO: 58; or wherein said TCR α chain sequence comprises a variable region sequence having the amino acid sequence of SEQ ID NO: 64, and wherein said TCR β chain sequence comprises a variable region sequence having the amino acid sequence of SEQ ID NO: 70; or wherein said TCR α chain sequence comprises a variable region sequence having the amino acid sequence of SEQ ID NO: 76, and wherein said TCR β chain sequence comprises a variable region sequence having the amino acid sequence of SEQ ID NO: 82; or wherein said TCR α chain sequence comprises a variable region sequence having the amino acid sequence of SEQ ID NO: 88, and wherein said TCR β chain sequence comprises a variable region sequence having the amino acid sequence of SEQ ID NO: 94; or wherein said TCR α chain sequence comprises a variable region sequence having the amino acid sequence of SEQ ID NO: 100, and wherein said TCR β chain sequence comprises a variable region sequence having the amino acid sequence of SEQ ID NO: 106; or wherein said TCR α chain sequence comprises a variable region sequence having the amino acid sequence of SEQ ID NO: 112, and wherein said TCR β chain sequence comprises a variable region sequence having the amino acid sequence of SEQ ID NO: 118.

In further embodiments of the invention the antigen recognizing construct as described herein before is a TCR, or a fragment thereof, further comprising a TCR constant region having at least 50%, 60%, 70%, 80%, 90%, 95%, 98%, 99%, or 100% sequence identity to an amino acid sequence selected from SEQ ID NOs: 5, 11, 17, 23, 29, 35, 41, 47, 53, 59, 65, 71, 77, 83, 89, 95, 101, 107, 113, and 119, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID NOs: 5, 17, 29, 41, 53, 65, 77, 89, 101, and 113; and wherein the TCR β chain sequence comprises a constant region having at least 50%, 60%, 70%, 80%, 90%, 95%, 98%, 99%, or 100% sequence identity to an amino acid sequence selected from SEQ ID NOs: 11, 23, 35, 47, 59, 71, 83, 95, 107, and 119.

Also disclosed are antigen recognizing constructs as described herein before comprising a first TCR chain having at least 50%, 60%, 70%, 80%, 90%, 95%, 98%, 99%, or 100% sequence identity to the amino acid sequence of SEQ ID NO: 6, and a second TCR chain having at least 50%, 60%, 70%, 80%, 90%, 95%, 98%, 99%, or 100% sequence identity to the amino acid sequence of SEQ ID NO: 12. The invention also provides TCRs comprising a first TCR chain having at least 50%, 60%, 70%, 80%, 90%, 95%, 98%, 99%, or 100% sequence identity to the amino acid sequence of SEQ ID NO: 18, and a second TCR chain having at least 50%, 60%, 70%, 80%, 90%, 95%, 98%, 99%, or 100% sequence identity to the amino acid sequence of SEQ ID NO: 24. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 30, and a second TCR chain having at least 50%, 60%, 70%, 80%, 90%, 95%, 98%, 99%, or 100% sequence identity to the amino acid sequence of SEQ ID NO: 36. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 42, and a second TCR chain having at least 50%, 60%, 70%, 80%, 90%, 95%, 98%, 99%, or 100% sequence identity to the amino acid sequence of SEQ ID NO: 48. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 54, and a second TCR chain having at least 50%, 60%, 70%, 80%, 90%, 95%, 98%, 99%, or 100% sequence identity to the amino acid sequence of SEQ ID NO: 60. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO:66, and a second TCR chain having at least 50%, 60%, 70%, 80%, 90%, 95%, 98%, 99%, or 100% sequence identity to the amino acid sequence of SEQ ID NO: 72. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 78, and a second TCR chain having at least 50%, 60%, 70%, 80%, 90%, 95%, 98%, 99%, or 100% sequence identity to the amino acid sequence of SEQ ID NO: 84. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 90, and a second TCR chain having at least 50%, 60%, 70%, 80%, 90%, 95%, 98%, 99%, or 100% sequence identity to the amino acid sequence of SEQ ID NO: 96. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 102, and a second TCR chain having at least 50%, 60%, 70%, 80%, 90%, 95%, 98%, 99%, or 100% sequence identity to the amino acid sequence of SEQ ID NO: 108. In further embodiments the invention provides antigen recognizing constructs which are TCR and comprise a first TCR chain having at least 50%, 60%, 70%, 80%, 90%, 95%, 98%, 99%, or 100% sequence identity to the amino acid sequence of SEQ ID NO: 114, and a second TCR chain having at least 50%, 60%, 70%, 80%, 90%, 95%, 98%, 99%, or 100% sequence identity to the amino acid sequence of SEQ ID NO: 120.

As used herein, the term "murine" or "human," when referring to an antigen recognizing construct, or a TCR, or any component of a TCR described herein (e.g., complementarity determining region (CDR), variable region, constant region, α chain, and/or β chain), means a TCR (or component thereof), which is derived from a mouse or a human unrearranged TCR locus, respectively.

In an embodiment of the invention, chimeric TCR are provided, wherein the TCR chains comprise sequences from multiple species. Preferably, a TCR of the invention may comprise an α chain comprising a human variable region of an α chain and, for example, a murine constant region of a murine TCR α chain.

In one embodiment, the TCR of the invention is a human TCR comprising human variable regions according to the above embodiments and human constant regions.

In some embodiments the antigen recognizing construct is murinized or humanized. These terms are used when amino acid sequences from a foreign species are introduced into a construct of the invention.

The TCR of the invention may be provided as a single chain TCR (scTCR). A scTCR according to the invention shall comprise in one polypeptide chain a full or partial alpha chain sequence and a full or partial beta chain sequence, preferably connected via a peptide linker. A scTCR can comprise a polypeptide of a variable region of a first TCR chain (e.g., an alpha chain) and a polypeptide of an entire (full-length) second TCR chain (e.g., a beta chain), or vice versa. Furthermore, the scTCR can optionally comprise one or more linkers which join the two or more polypeptides together. The linker can be, for instance, a peptide, which joins together two single chains, as described herein. Also provided is such a scTCR of the invention, which is fused to a human cytokine, such as IL-2, IL-7 or IL-15.

The antigen recognizing construct according to the invention can also be provided in the form of a multimeric complex, comprising at least two scTCR molecules, wherein said scTCR molecules are each fused to at least one biotin moiety, or other interconnecting molecule/linker, and wherein said scTCRs are interconnected by biotin-streptavidin interaction to allow the formation of said multimeric complex. Similar approaches known in the art for the generation of multimeric TCR are also possible and included in this disclosure. Also provided are multimeric complexes of a higher order, comprising more than two scTCR of the invention.

For the purposes of the present invention, a TCR is a moiety having at least one TCR alpha or gamma and/or TCR beta or delta variable domain. Generally, they comprise both a TCR alpha variable domain and a TCR beta variable domain, alternatively both a TCR gamma variable domain and a TCR delta variable domain. They may be a β/γδ heterodimers or may be in single chain format. For use in adoptive therapy, an αβ or γδ heterodimeric TCR may, for example, be transfected as full-length chains having both cytoplasmic and transmembrane domains. If desired, an introduced disulfide bond between residues of the respective constant domains may be present.

In a preferred embodiment, the antigen recognizing construct is a human TCR, or fragment or derivative thereof. A human TCR or fragment or derivative thereof is a TCR, which comprises over 50% of the corresponding human TCR sequence. Preferably, only a small part of the TCR sequence is of artificial origin or derived from other species. It is known, however, that chimeric TCRs, e.g. derived from human origin with murine sequences in the constant domains, are advantageous. Particularly preferred are, therefore, TCRs in accordance with the present invention, which contains murine sequences in the extracellular part of their constant domains.

Thus, it is also preferred that the inventive antigen recognizing construct is able to recognize its antigen in a human leucocyte antigen (HLA) dependent manner, preferably in a HLA-A*02 dependent manner. The term "HLA dependent manner" in the context of the present invention means that the antigen recognizing construct binds to the antigen only in the event that the antigenic peptide is presented by said HLA.

The antigen recognizing construct in accordance with the invention in one embodiment preferably induces an immune response, preferably wherein the immune response is characterized by the increase in interferon (IFN) γ levels.

Also provided by the invention is a polypeptide comprising a functional portion of any of the TCRs (or functional variants thereof) described herein, for examples, of any one of the TCRs selected from R39P1C12, R39P1F5, R40P1C2, R41P3E6, R43P3G4, R44P3B3, R44P3E7, R49P2B7, R55P1G7 and R59P2A7, as provided in the example section and table 1. The term "polypeptide" as used herein includes oligopeptides and refers to a single chain of amino acids connected by one or more peptide bonds. With respect to the inventive polypeptides, the functional portion can be any portion comprising contiguous amino acids of the TCR (or functional variant thereof), of which it is a part, provided that the functional portion specifically binds to the TAA antigen, preferably as disclosed herein in Table 2, and peptides A2 to A9 (SEQ ID NOs: 134-140) and T1 to T9 (SEQ ID:141-149). The term "functional portion" when used in reference to a TCR (or functional variant thereof) refers to any part or fragment of the TCR (or functional variant thereof) of the invention, which part or fragment retains the biological activity of the TCR (or functional variant thereof), of which it is a part (the parent TCR or parent functional variant thereof). Functional portions encompass, for example, those parts of a TCR (or functional variant thereof) that retain the ability to specifically bind to the TAA antigen (in an HLA dependent manner), or detect, treat, or prevent cancer, to a similar extent, the same extent, or to a higher extent, as the parent TCR (or functional variant thereof). In reference to the parent TCR (or functional variant thereof), the functional portion can comprise, for instance, about 10%, 25%, 30%, 50%, 68%, 80%, 90%, 95%, or more, of the parent TCR variable sequences (or functional variant thereof).

The functional portion can comprise additional amino acids at the amino or carboxy terminus of the portion, or at both termini, in which additional amino acids are not found in the amino acid sequence of the parent TCR or functional variant thereof. Desirably, the additional amino acids do not interfere with the biological function of the functional portion, e.g., specifically binding to the TAA antigens; and/or having the ability to detect cancer, treat or prevent cancer, etc. More desirably, the additional amino acids enhance the biological activity, as compared to the biological activity of the parent TCR or functional variant thereof.

The polypeptide can comprise a functional portion of either or both of the α and β chains of the TCRs or functional variant thereof of the invention, such as a functional portion comprising one of more of CDR1, CDR2, and (preferably) CDR3 of the variable region(s) of the α chain and/or β chain of a TCR or functional variant thereof of the invention. In an embodiment of the invention, the polypeptide can comprise a functional portion comprising the amino acid sequence of SEQ ID NOs: 3, 9, 15, 21, 27, 33, 39, 45, 51, 57, 63, 69, 75, 81, 87, 93, 99, 105, 111, and 117 (CDR3 of the variable regions of the TCR of the invention), or a combination thereof. In an embodiment of the invention, the inventive polypeptide can comprise, for instance, the variable region of the inventive TCR or functional variant thereof comprising a combination of the CDR regions set forth above. In this regard, the polypeptide can comprise the amino acid sequence of any of SEQ ID NOs: 4, 10, 16, 22, 28, 34, 40, 46, 52, 58, 64, 70, 76, 82, 88, 94, 100, 106, 112, and 118 (the variable regions of an α or β chain of the TCR of the invention).

In some instances, the construct of the invention may comprise one or two polypeptide chains comprising sequences according to any of the SEQ ID NOs: 1 to 120 (CDR sequences, constant and variable regions and full-length sequences), or functional fragments thereof, and further comprise(s) other amino acid sequences, e.g., an amino acid sequence encoding an immunoglobulin or a portion thereof, then the inventive protein can be a fusion protein. In this regard, the invention also provides a fusion protein comprising at least one of the inventive polypeptides described herein along with at least one other polypeptide. The other polypeptide can exist as a separate polypeptide of the fusion protein, or can exist as a polypeptide, which is expressed in frame (in tandem) with one of the inventive polypeptides described herein. The other polypeptide may include any peptidic or proteinaceous molecule, or a portion thereof, including, but not limited to an immunoglobulin, CD3, CD4, CD8, an MHC molecule, a CD1 molecule, e.g., CD1a, CD1b, CD1c, CD1d, etc.

The fusion protein can comprise one or more copies of the inventive polypeptide and/or one or more copies of the other polypeptide. For instance, the fusion protein can comprise 1, 2, 3, 4, 5, or more, copies of the inventive polypeptide and/or of the other polypeptide. Suitable methods of making fusion proteins are known in the art, and include, for example, recombinant methods. In some embodiments of the invention, the TCRs (and functional portions and functional variants thereof), polypeptides, and proteins of the invention may be expressed as a single protein comprising a linker peptide linking the α chain and the 13 chain, and linking the γ chain and the δ chain. In this regard, the TCRs (and functional variants and functional portions thereof), polypeptides, and proteins of the invention comprising the amino acid sequences of the variable regions of the TCR of the invention and may further comprise a linker peptide. The linker peptide may advantageously facilitate the expression of a recombinant TCR (including functional portions and functional variants thereof), polypeptide, and/or protein in a host cell. The linker peptide may comprise any suitable amino acid sequence. Linker sequences for single chain TCR constructs are well known in the art. Such a single chain construct may further comprise one, or two, constant domain sequences. Upon expression of the construct including the linker peptide by a host cell, the linker peptide may also be cleaved, resulting in separated α and β chains, and separated γ and δ chain.

As already mentioned above, the binding functionality of the TCR of the invention may be provided in the framework of an antibody. For example, CDR sequences of the TCR of the invention, possibly including additional 3, 2 or 1 N and/or C terminal framework residues, may be directly grafted into an antibody variable heavy/light chain sequence. The term "antibody" in its various grammatical forms is used herein to refer to immunoglobulin molecules and immunologically active portions of immunoglobulin molecules, i.e., molecules that contain an antigen-binding site or a paratope. Such molecules are also referred to as "antigen binding fragments" of immunoglobulin molecules. The invention further provides an antibody, or antigen binding portion thereof, which specifically binds to the antigens described herein. The antibody can be any type of immunoglobulin that is known in the art. For instance, the antibody can be of any isotype, e.g., IgA, IgD, IgE, IgG, IgM, etc. The antibody can be monoclonal or polyclonal. The antibody can be a naturally-occurring antibody, e.g., an antibody isolated and/or purified from a mammal, e.g., mouse, rabbit, goat, horse, chicken, hamster, human, etc. Alternatively, the antibody can be a genetically-engineered antibody, e.g., a humanized antibody or a chimeric antibody. The antibody can be in monomeric or polymeric form.

The term "antibody" includes, but is not limited to, genetically engineered or otherwise modified forms of immunoglobulins, such as intrabodies, chimeric antibodies, fully human antibodies, humanized antibodies (e.g. generated by "CDR-grafting"), antibody fragments, and heteroconjugate antibodies (e.g., bispecific antibodies, diabodies, triabodies, tetra-bodies, etc.). The term "antibody" includes cys-diabodies and minibodies. Thus, each and every embodiment provided herein in regard to "antibodies", or "antibody like constructs" is also envisioned as, bispecific antibodies, diabodies, scFv fragments, chimeric antibody receptor (CAR) constructs, diabody and/or minibody embodiments, unless explicitly denoted otherwise. The term "antibody" includes a polypeptide of the immunoglobulin family or a polypeptide comprising fragments of an immunoglobulin that is capable of non-covalently, reversibly, and in a specific manner binding a corresponding antigen, preferably the TAA of the invention, as disclosed herein. An exemplary antibody structural unit comprises a tetramer. In some embodiments, a full-length antibody can be composed of two identical pairs of polypeptide chains, each pair having one "light" and one "heavy" chain (connected through a disulfide bond). Antibody structure and isotypes are well known to the skilled artisan (for example from Janeway's Immunobiology, 9th edition, 2016).

The recognized immunoglobulin genes of mammals include the kappa, lambda, alpha, gamma, delta, epsilon, and mu constant region genes, as well as the myriad immunoglobulin variable region genes (for more information on immunoglobulin genes see the international Im-MunoGeneTics information System®, Lefranc M-P et al, Nucleic Acids Res. 2015 January; 43(Database issue):D413-22; and http://www.imgt.org/). For full-length chains, the light chains are classified as either kappa or lambda. For full-length chains, the heavy chains are classified as gamma, mu, alpha, delta, or epsilon, which in turn define the immunoglobulin classes, IgG, IgM, IgA, IgD, and IgE, respectively. The N-terminus of each chain defines a variable region of about 100 to 110 or more amino acids primarily responsible for antigen recognition. The terms variable light chain (VL) and variable heavy chain (VH) refer to these regions of light and heavy chains respectively. As used in this invention, an "antibody" encompasses all variations of antibody and fragments thereof. Thus, within the scope of this concept are full length antibodies, chimeric antibodies, humanized antibodies, single chain antibodies (scFv), Fab, Fab', and multimeric versions of these fragments (e.g., F(ab')2) with the same, essentially the same or similar binding specificity. In some embodiments, the anti-body binds specifically to a peptide TAA of the invention. Preferred antigen recognizing constructs according to the invention include an antibody heavy chain, preferably the variable domain thereof, or an antigen binding fragment thereof, and/or an antibody light chain, preferably the variable domain thereof, or an antigen binding fragment thereof. Similarly, disulfide-stabilized variable region fragments (dsFv) can be prepared by recombinant DNA technology, antibody fragments of the invention, however, are not limited to these exemplary types of antibody fragments. Also, the antibody, or antigen binding portion thereof, can be modified to comprise a detectable label, such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles). In some instances, the TCR CDR3 sequence may be slightly modified, but preferably by not more than 3 amino acid residues, preferably only two and most preferably only one amino acid position, as compared to the CDR3 sequences provided in SEQ ID NO of the CDR3 in table 1. Preferably, the antibodies comprise the CDR3, preferably all of CDR1 to CDR3 regions in the combination, as indicated for the TCR of the invention in table 1, in each case independently, optionally with not more than three or two, preferably one, amino acid substitution(s), insertion(s) and/or deletion(s) compared to these sequences.

Suitable methods of making antibodies are known in the art. For instance, standard hybridoma methods are described in, e.g., Kohler and Milstein, Eur. J. Immunol, 5, 511-519 (1976), Harlow and Lane (eds.), Antibodies: A Laboratory Manual, CSH Press (1988), and C. A. Janeway et al. (eds.), Immunobiology, 8 Ed., Garland Publishing, New York, N.Y. (2011)). Alternatively, other methods, such as EBV-hybridoma methods (Haskard and Archer, J. Immunol. Methods, 74(2), 361-67 (1984), and Roder et al, Methods Enzymol, 121, 140-67 (1986)), and bacteriophage vector expression systems (see, e.g., Huse et al., Science, 246, 1275-81 (1989)) are known in the art. Further, methods of producing antibodies in non-human animals are described in, e.g., U.S. Pat. Nos. 5,545,806, 5,569,825, and 5,714,352, and U.S. Patent Application Publication No. 2002/0197266.

Some embodiments of the invention also pertain to TCRs, or functional fragments and polypeptides thereof, which are soluble TCRs. As used herein, the term "soluble T-cell receptor" refers to heterodimeric truncated variants of native TCRs, which comprise extracellular portions of the TCR α-chain and β-chain, for example linked by a disulfide bond, but which lack the transmembrane and cytosolic domains of the native protein. The terms "soluble T-cell receptor α-chain sequence and soluble T-cell receptor β-chain sequence" refer to TCR α-chain and β-chain sequences that lack the transmembrane and cytosolic domains. The sequence (amino acid or nucleic acid) of the soluble TCR α-chain and β-chains may be identical to the corresponding sequences in a native TCR or may comprise variant soluble TCR α-chain and β-chain sequences, as compared to the corresponding native TCR sequences. The term "soluble T-cell receptor" as used herein encompasses soluble TCRs with variant or non-variant soluble TCR α-chain and β-chain sequences. The variations may be in the variable or constant regions of the soluble TCR α-chain and β-chain sequences and can include, but are not limited to, amino acid deletion, insertion, substitution mutations as well as changes to the nucleic acid sequence, which do not alter the amino acid sequence. Soluble TCR of the invention in any case retain the binding functionality of their parent molecules.

The above problem is further solved by a nucleic acid encoding for an antigen recognizing construct of the invention, or any of the aforementioned protein or polypeptide constructs. The nucleic acid preferably (a) has a strand encoding for an antigen recognizing construct according to the invention; (b) has a strand complementary to the strand in (a); or (c) has a strand that hybridizes under stringent conditions with a molecule as described in (a) or (b). Stringent conditions are known to the person of skill in the art, specifically from Sambrook et al, "Molecular Cloning". In addition to that, the nucleic acid optionally has further sequences, which are necessary for expressing the nucleic acid sequence corresponding to the protein, specifically for expression in a mammalian/human cell. The nucleic acid used can be contained in a vector suitable for allowing expression of the nucleic acid sequence corresponding to the peptide in a cell. However, the nucleic acids can also be used to transform an antigen-presenting cell, which may not be restricted to classical antigen-presenting cells, such as dendritic cells, in such a way that they themselves produce the corresponding proteins on their cellular surface.

In some embodiments, the polypeptides of the antigen recognizing constructs can be encoded by nucleic acids and expressed in vivo or in vitro. Thus, in some embodiments, a nucleic acid encoding an antigen recognizing construct is provided. In some embodiments, the nucleic acid encodes one part or monomer of an antigen recognizing construct of the invention (for example one of two chains of a TCR of the invention), and/or another nucleic acid encodes another part or monomer of an antigen recognizing construct of the invention (for example the other of two chains of the TCR). In some embodiments, the nucleic acid encodes two or more antigen recognizing construct polypeptide chains, for example, at least 2 TCR chains. Nucleic acids encoding multiple antigen recognizing construct chains can include nucleic acid cleavage sites between at least two chain sequences, can encode transcription or translation start site between two or more chains sequences, and/or can encode proteolytic target sites between two or more antigen recognizing construct chains.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and can contain a natural, non-natural or altered internucleotide linkage, such as a phosphoroamidate linkage or a phosphorothioate linkage, instead of the phosphodiester found between the nucleotides of an unmodified oligonucleotide.

Preferably, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication. The nucleic acid can comprise any nucleotide sequence, which encodes any of the TCRs, polypeptides, or proteins, or functional portions or functional variants thereof described herein.

Furthermore, the invention provides a vector comprising a nucleic acid in accordance to the invention as described above. Desirably, the vector is an expression vector or a recombinant expression vector. The term "recombinant expression vector" refers in context of the present invention to a nucleic acid construct that allows for the expression of an mRNA, protein or polypeptide in a suitable host cell. The recombinant expression vector of the invention can be any suitable recombinant expression vector, and can be used to transform or transfect any suitable host. Suitable vectors include those designed for propagation and expansion or for expression or both, such as plasmids and viruses. Examples of animal expression vectors include pEUK-Cl, pMAM, and pMAMneo. Preferably, the recombinant expression vector is a viral vector, e.g., a retroviral vector. The recombinant expression vector comprises regulatory sequences, such as transcription and translation initiation and termination codons, which are specific to the type of host cell (e.g., bacterium, fungus, plant, or animal), into which the vector is to be introduced and in which the expression of the nucleic acid of the invention may be performed. Furthermore, the vector of the invention may include one or more marker genes, which allow for selection of transformed or transfected hosts. The recombinant expression vector can comprise a native or normative promoter operably linked to the nucleotide sequence encoding the constructs of the invention, or to the nucleotide sequence, which is complementary to or which hybridizes to the nucleotide sequence encoding the constructs of the invention. The selections of promoters include, e.g., strong, weak, inducible, tissue-specific and developmental-specific promoters. The promoter can be a non-viral promoter or a viral promoter. The inventive recombinant expression vectors can be designed for either transient expression, for stable expression, or for both. Also, the recombinant expression vectors can be made for constitutive expression or for inducible expression.

The invention also pertains to a host cell comprising an antigen recognizing construct in accordance with the invention. Specifically, the host cell of the invention comprises a nucleic acid, or a vector as described herein above. The host cell can be a eukaryotic cell, e.g., plant, animal, fungi, or algae, or can be a prokaryotic cell, e.g., bacteria or protozoa. The host cell can be a cultured cell or a primary cell, i.e., isolated directly from an organism, e.g., a human. The host cell can be an adherent cell or a suspended cell, i.e., a cell that grows in suspension. For purposes of producing a recombinant TCR, polypeptide, or protein, the host cell is preferably a mammalian cell. Most preferably, the host cell is a human cell. While the host cell can be of any cell type, can originate from any type of tissue, and can be of any developmental stage, the host cell preferably is a peripheral blood leukocyte (PBL) or a peripheral blood mononuclear cell (PBMC). More preferably, the host cell is a T cell. The T cell can be any T cell, such as a cultured T cell, e.g., a primary T cell, or a T cell from a cultured T cell line, e.g., Jurkat, SupT1, etc., or a T cell obtained from a mammal, preferably a T cell or T cell precursor from a human patient. If obtained from a mammal, the T cell can be obtained from numerous sources, including but not limited to blood, bone marrow, lymph node, the thymus, or other tissues or fluids. T cells can also be enriched for or purified. Preferably, the T cell is a human T cell. More preferably, the T cell is a T cell isolated from a human. The T cell can be any type of T cell and can be of any developmental stage, including but not limited to, CD4-positive and/or CD8-positive, CD4-positive helper T cells, e.g., Th1 and Th2 cells, CD8-positive T cells (e.g., cytotoxic T cells), tumor infiltrating cells (TILs), memory T cells, naive T cells, and the like. Preferably, the T cell is a CD8-positive T cell or a CD4-positive T cell.

Preferably, the host cell of the invention is a lymphocyte, preferably, a T lymphocyte, such as a CD4-positive or CD8-positive T-cell. The host cell furthermore preferably is a tumor reactive T cell specific for TAA expressing tumor cells.

The objective of the invention is also solved by a method of manufacturing a TAA specific antigen recognizing construct, or of a TAA specific antigen recognizing construct expressing cell line, comprising
a. Providing a suitable host cell,
b. Providing a genetic construct comprising a coding sequence encoding for an antigen recognizing construct according to the herein disclosed invention,
c. Introducing into said suitable host cell said genetic construct, and
d. Expressing said genetic construct by said suitable host cell.

The method may further comprise a step of cell surface presentation of said antigen recognizing construct on said suitable host cell.

In other preferred embodiments, the genetic construct is an expression construct comprising a promoter sequence operably linked to said coding sequence.

Preferably, said antigen recognizing construct is of mammalian origin, preferably of human origin. The preferred suitable host cell for use in the method of the invention is a mammalian cell, such as a human cell, in particular a human T lymphocyte. T cells for use in the invention are described in detail herein above.

Also encompassed by the invention are embodiments, wherein said antigen recognizing construct is a modified TCR, wherein said modification is the addition of functional domains, such as a label or a therapeutically active substance. Furthermore, encompassed are TCR having alternative domains, such as an alternative membrane anchor domain instead of the endogenous transmembrane region.

Desirably, the transfection system for introducing the genetic construct into said suitable host cell is a retroviral vector system. Such systems are well known to the skilled artisan.

Also comprised by the present invention is in one embodiment the additional method step of isolation and purification of the antigen recognizing construct from the cell and, optionally, the reconstitution of the translated antigen recognizing construct-fragments in a T-cell.

In an alternative aspect of the invention a T-cell is provided obtained or obtainable by a method for the production of a T cell receptor (TCR), which is specific for tumorous cells and has high avidity as described herein above. Such a T cell is depending on the host cell used in the method of the invention, for example, a human or non-human T-cell, preferably a human TCR.

The term "isolated" as used herein in the context of a polypeptide, such as an antigen recognizing construct (an example of which could be an antibody), refers to a polypeptide that is purified from proteins or polypeptides or other contaminants that would interfere with its therapeutic, diagnostic, prophylactic, research or other use. An antigen recognizing construct according to the invention may be a recombinant, synthetic or modified (non-natural) antigen binding construct. The term "isolated" as used herein in the context of a nucleic acid or cells refers to a nucleic acid or cells that is/are purified from DNA, RNA, proteins or polypeptides or other contaminants (such as other cells) that would interfere with its therapeutic, diagnostic, prophylactic, research or other use, or it refers to a recombinant, synthetic or modified (non-natural) nucleic acid. In this context, a "recombinant" protein/polypeptide or nucleic acid is one made using recombinant techniques. Methods and techniques for the production of recombinant nucleic acids and proteins are well known in the art.

Treatment Methods and Diseases One further aspect of the present invention relates to the herein disclosed antigen recognizing constructs, nucleic acids, vectors, pharmaceutical compositions and/or host cell for use in medicine. The use in medicine in one preferred embodiment includes the use in the diagnosis, prevention and/or treatment of a tumor disease, such as a malignant or benign tumor disease. The tumor disease is, for example, a tumor disease characterized by the expression of the TAA, in a cancer or tumor cell of said tumor disease.

With respect to the above mentioned medical applications of the antigen recognizing constructs and other materials derived therefrom, pertaining thereto or encoding the same, in accordance with the present disclosure, the to be treated and/or to be diagnosed diseases can be any proliferative disorder, preferably characterized by the expression of the TAA or TAA epitope sequence of the invention, for example any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer is cancer of the uterine cervix, oropharynx, anus, anal canal, anorectum, vagina, vulva, or penis. A particularly preferred cancer is a TAA positive cancer, including preferably lymphoma.

The constructs, proteins, TCRs antibodies, polypeptides and nucleic acids of the invention are in particular for use in immune therapy, preferably, in adoptive T cell therapy. The administration of the compounds of the invention can, for example, involve the infusion of T cells of the invention into said patient. Preferably, such T cells are autologous T cells of the patient and in vitro transduced with a nucleic acid or antigen recognizing construct of the present invention.

The inventive antigen recognizing constructs, TCRs, polypeptides, proteins (including functional variants thereof), nucleic acids, recombinant expression vectors, host cells (including populations thereof), and antibodies (including antigen binding portions thereof), all of which are collectively referred to as "inventive TCR materials" hereinafter, can be formulated into a composition, such as a pharmaceutical composition. In this regard, the invention provides a pharmaceutical composition comprising any of the antigen recognizing constructs, TCRs, polypeptides, proteins, functional portions, functional variants, nucleic acids, expression vectors, host cells (including populations thereof), and antibodies (including antigen binding portions thereof) described herein, and a pharmaceutically acceptable carrier, excipient and/or stabilizer. The inventive pharmaceutical compositions containing any of the inventive TCR materials can comprise more than one inventive TCR material, e.g., a polypeptide and a nucleic acid, or two or more different TCRs (including functional portions and functional variants thereof). Alternatively, the pharmaceutical composition can comprise an inventive TCR material in combination with another pharmaceutically active agent(s) or drug(s), such as chemotherapeutic agents, e.g., asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc.

Preferably, the carrier is a pharmaceutically acceptable carrier. With respect to pharmaceutical compositions, the carrier can be any of those conventionally used for the particular inventive TCR material under consideration. Such pharmaceutically acceptable carriers are well-known to those skilled in the art and are readily available to the public. It is preferred that the pharmaceutically acceptable carrier be one, which has no detrimental side effects or toxicity under the conditions of use.

Thus also provided is a pharmaceutical composition, comprising any of the herein described products of the invention and TCR materials of the invention, specifically any proteins, nucleic acids or host cells. In a preferred embodiment the pharmaceutical composition is for immune therapy, preferably adoptive cell therapy.

Preferably, the inventive TCR material is administered by injection, e.g., intravenously. When the inventive TCR material is a host cell expressing the inventive TCR (or functional variant thereof), the pharmaceutically acceptable carrier for the cells for injection may include any isotonic carrier such as, for example, normal saline (about 0.90% w/v of NaCl in water, about 300 mOsm/L NaCl in water, or about 9.0 g NaCl per liter of water), NORMOSOL R electrolyte solution (Abbott, Chicago, Ill.), PLASMA-LYTE A (Baxter, Deerfield, Ill.), about 5% dextrose in water, or Ringer's lactate. In an embodiment, the pharmaceutically acceptable carrier is supplemented with human serum albumen.

For purposes of the invention, the amount or dose (e.g., numbers of cells when the inventive TCR material is one or more cells) of the inventive TCR material administered may be sufficient to affect, e.g., a therapeutic or prophylactic response, in the subject or animal over a reasonable time frame. For example, the dose of the inventive TCR material should be sufficient to bind to a cancer antigen, or detect, treat or prevent cancer in a period of from about 2 hours or longer, e.g., 12 to 24 or more hours, from the time of administration. In certain embodiments, the time period could be even longer. The dose will be determined by the efficacy of the particular inventive TCR material and the condition of the animal (e.g., human), as well as the body weight of the animal (e.g., human) to be treated.

It is contemplated that the inventive pharmaceutical compositions, antigen recognizing constructs, TCRs (including functional variants thereof), polypeptides, proteins, nucleic acids, recombinant expression vectors, host cells, or populations of cells can be used in methods of treating or preventing cancer, or TAA-positive premalignancy. The inventive TCRs (and functional variants thereof) are believed to bind specifically to the TAA of the invention, such that the TCR (or related inventive polypeptide or protein and functional variants thereof), when expressed by or on a cell, such as a T cell, is able to mediate an immune response against a target cell expressing the TAA of the invention, preferably presenting TAA peptides via MHC I or II on the surface of said target cell. In this regard, the invention provides a method of treating or preventing a condition, in particular cancer, in a mammal, comprising administering to the mammal any of the pharmaceutical compositions, antigen recognizing constructs, in particular TCRs (and functional variants thereof), polypeptides, or proteins described herein, any nucleic acid or recombinant expression vector comprising a nucleotide sequence encoding any of the TCRs (and functional variants thereof), polypeptides, proteins described herein, or any host cell or population of cells comprising a nucleic acid or recombinant vector, which encodes any of the constructs of the invention (and functional variants thereof), polypeptides, or proteins described herein, in an amount effective to treat or prevent the condition in the mammal, wherein the condition is preferably cancer, such as a cancer expressing the TAA of the invention.

Examples of pharmaceutically acceptable carriers or diluents useful in the present invention include stabilizers such as SPGA, carbohydrates (e.g. sorbitol, mannitol, starch, sucrose, glucose, dextran), proteins such as albumin or casein, protein containing agents such as bovine serum or skimmed milk and buffers (e.g. phosphate buffer).

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of treatment or prevention of a condition in a mammal. Furthermore, the treatment or prevention provided by the inventive method can include treatment or prevention of one or more conditions or symptoms of the condition, e.g., cancer, being treated or prevented. For example, treatment or prevention can include promoting the regression of a tumor. Also, for purposes herein, "prevention" can encompass delaying the onset of the condition, or a symptom or condition thereof.

The present invention also relates to a method of treating cancer comprising administering a TCR, a nucleic acid, or a host cell of the present description in combination with at least one chemotherapeutic agent and/or radiation therapy.

Another aspect of the invention further pertains to a method for detecting a TAA protein, or a complex of MHC and the TAA protein (protein epitope of the TAA), in a (biological) sample—such as one obtained from a subject or patient—comprising contacting the sample with an antigen recognizing construct specifically binding to said TAA peptide, or to the TAA peptide/MHC complex, and detecting the binding between said antigen recognizing construct and said TAA peptide, or to the TAA peptide/MHC complex. In some embodiments, the antigen recognizing construct is a TCR or antibody, or similar constructs, or preferably the antigen recognizing construct according to the herein described invention. In some embodiments, the (biological) sample is a sample of a tumor or a cancer (such as one of those described elsewhere herein) for example a sample comprising tumor or cancer cells.

Also provided is a method of treating cancer in a subject in need thereof, comprising:
  a) isolating a cell from said subject;
  b) transforming the cell with at least one vector encoding an antigen recognizing construct of the present invention to produce a transformed cell;
  c) expanding the transformed cell to produce a plurality of transformed cells; and
  d) administering the plurality of transformed cells to said subject.

Also provided is a method of treating cancer in a subject in need thereof, comprising:
  a) isolating a cell from a healthy donor;
  b) transforming the cell with a vector encoding an antigen recognizing construct of the present invention to produce a transformed cell;
  c) expanding the transformed cell to produce a plurality of transformed cells; and
  d) administering the plurality of transformed cells to said subject.

Also provided is a method of detecting cancer in a biological sample comprising:
  a) contacting the biological sample with an antigen recognizing construct of the present description;
  b) detecting binding of the antigen recognizing construct to the biological sample.

In some embodiments, the method of detecting cancer is carried out in vitro, in vivo or in situ.

Also provided is a method of detecting the presence of a condition in a mammal. The method comprises (i) contacting a sample comprising one or more cells from the mammal with any of the inventive TCRs (and functional variants thereof), polypeptides, proteins, nucleic acids, recombinant expression vectors, host cells, populations of cells, antibodies, or antigen binding portions thereof, or pharmaceutical compositions described herein, thereby forming a complex, and detecting the complex, wherein detection of the complex is indicative of the presence of the condition in the mammal, wherein the condition is cancer, such as a TAA expressing malignancy.

With respect to the inventive method of detecting a condition in a mammal, the sample of cells can be a sample comprising whole cells, lysates thereof, or a fraction of the whole cell lysates, e.g., a nuclear or cytoplasmic fraction, a whole protein fraction, or a nucleic acid fraction.

For purposes of the inventive detecting method, the contacting can take place in vitro or in vivo with respect to the mammal. Preferably, the contacting is in vitro.

Also, detection of the complex can occur through any number of ways known in the art. For instance, the inventive antigen recognizing constructs (and functional variants thereof), polypeptides, proteins, nucleic acids, recombinant expression vectors, host cells, populations of cells, or antibodies or TCRs, or antigen binding portions thereof, described herein, can be labeled with a detectable label such as, for instance, a radioisotope, a fluorophore (e.g., fluorescein isothiocyanate (FITC), phycoerythrin (PE)), an enzyme (e.g., alkaline phosphatase, horseradish peroxidase), and element particles (e.g., gold particles).

For purposes of the inventive methods, wherein host cells or populations of cells are administered, the cells can be cells that are allogeneic or autologous to the mammal. Preferably, the cells are autologous to the mammal.

With respect to the above mentioned medical applications of the TCR material of the invention, the to be treated and/or diagnosed cancer can be any cancer, including any of acute lymphocytic cancer, acute myeloid leukemia, alveolar rhabdomyosarcoma, bone cancer, brain cancer, breast cancer, cancer of the anus, anal canal, or anorectum, cancer of the eye, cancer of the intrahepatic bile duct, cancer of the joints, cancer of the neck, gallbladder, or pleura, cancer of the nose, nasal cavity, or middle ear, cancer of the oral cavity, cancer of the vagina, cancer of the vulva, chronic lymphocytic leukemia, chronic myeloid cancer, colon cancer, esophageal cancer, cervical cancer, gastrointestinal carcinoid tumor, glioma, Hodgkin lymphoma, hypopharynx cancer, kidney cancer, larynx cancer, liver cancer, lung cancer, malignant mesothelioma, melanoma, multiple myeloma, nasopharynx cancer, non-Hodgkin lymphoma, cancer of the oropharynx, ovarian cancer, cancer of the penis, pancreatic cancer, peritoneum, omentum, and mesentery cancer, pharynx cancer, prostate cancer, rectal cancer, renal cancer, skin cancer, small intestine cancer, soft tissue cancer, stomach cancer, testicular cancer, thyroid cancer, cancer of the uterus, ureter cancer, and urinary bladder cancer. A preferred cancer is cancer of the uterine cervix, oropharynx, anus, anal canal, anorectum, vagina, vulva, or penis. A particularly preferred cancer is a TAA positive cancer, such as a Spink2 positive lymphoma.

In general, the invention provides a method for treating a subject suffering from a tumor or tumor disease comprising the administration of the antigen recognizing constructs, nucleic acids, vectors, pharmaceutical compositions and/or host cell as disclosed by the present invention. Preferably the subject is a subject in need of such a treatment. The subject in preferred embodiments is a mammalian subject, preferably a human patient, suffering from a tumor or tumor disease, which is TAA-positive.

In view of the disclosure herein it will be appreciated that the invention furthermore pertains to the following items:

Item 1: An antigen recognizing construct comprising at least one complementary determining region (CDR) 3 having at least 50% sequence identity to an amino acid sequence selected from SEQ ID NOs: 3, 9, 15, 21, 27, 33, 39, 45, 51, 57, 63, 69, 75, 81, 87, 93, 99, 105, 111, and 117.

Item 2: The antigen recognizing construct according to item 1, wherein said antigen recognizing construct is capable of specifically and/or selectively binding to a TAA of the invention antigenic peptide.

Item 3: The antigen recognizing construct according to item 1 or 2, wherein the antigen recognizing construct is an antibody, or derivative or fragment thereof, or a T cell receptor (TCR), or a derivative or fragment thereof.

Item 4: The antigen recognizing construct according to any one of items 1 to 3, wherein said antigen recognizing construct binds to a human leucocyte antigen (HLA) presented TAA antigenic peptide, wherein said HLA is optionally type A2.

Item 5: The antigen recognizing construct according to any one of items 1 to 4, wherein the construct specifically and/or selectively binds to an epitope having the amino acid sequence selected from SEQ ID NOs: 133 to 158.

Item 6: The antigen recognizing construct according to any one of items 1 to 5, wherein the construct is an α/β-TCR, or fragment or derivative thereof, or the construct is a γ/δ-TCR, or a fragment or derivative thereof.

Item 7: The antigen recognizing construct according to any one of items 1 to 6, characterized in that the construct is of human origin and specifically and/or selectively recognizes a TAA antigenic peptide.

Item 8: The antigen recognizing construct according to any one of items 1 to 7, wherein said antigen recognizing construct is capable of inducing an immune response in a subject, optionally wherein the immune response is characterized by an increase in interferon (IFN) γ levels.

Item 9: The antigen recognizing construct according to any one of items 1 to 8, comprising a TCR α or γ chain; and/or a TCR β or δ chain; wherein the TCR α or γ chain comprises a CDR3 having at least 50%, 60%, 70%, 80%, 90%, 95%, 98%, 99%, or 100% sequence identity to an amino acid sequence selected from SEQ ID NOs: 3, 15, 27, 39, 51, 63, 75, 87, 99, and 111, and/or wherein the TCR β or δ chain comprises a CDR3 having at least 50%, 60%, 70%, 80%, 90%, 95%, 98%, 99%, or 100% sequence identity to an amino acid sequence selected from SEQ ID NOs: 9, 21, 33, 45, 57, 69, 81, 93, 105, and 117.

Item 10: The antigen recognizing construct according to item 9, wherein the TCR α or γ chain further comprises a CDR1 having at least 50%, 60%, 70%, 80%, 90%, 95%, 98%, 99%, or 100% sequence identity to an amino acid sequence selected from SEQ ID NOs: 1, 13, 25, 37, 49, 61, 73, 85, 97, and 109; and/or a CDR2 having at least 50%, 60%, 70%, 80%, 90%, 95%, 98%, 99%, or 100% sequence identity to an amino acid sequence selected from SEQ ID NOs: 2, 14, 26, 38, 50, 62, 74, 86, 98, and 110.

Item 11: The antigen recognizing construct according to item 9 or 10, wherein the TCR β or δ chain further comprises a CDR1 having at least 50%, 60%, 70%, 80%, 90%, 95%, 98%, 99%, or 100% sequence identity to an amino acid sequence selected from SEQ ID NOs: 7, 19, 31, 43, 55, 67, 79, 91, 103, and 115; and/or a CDR2 having at least 50%, 60%, 70%, 80%, 90%, 95%, 98%, 99%, or 100% sequence identity to an amino acid sequence selected from SEQ ID NOs: 8, 20, 32, 44, 56, 68, 80, 92, 104, and 116.

Item 12: The antigen recognizing construct according to any of items 1 to 11, comprising a TCR variable chain region having at least 50%, 60%, 70%, 80%, 90%, 95%, 98%, 99%, or 100% sequence identity to an amino acid sequence selected from SEQ ID NOs: 4, 10, 16, 22, 28, 34, 40, 46, 52, 58, 64, 70, 76, 82, 88, 94, 100, 106, 112, and 118.

Item 13: The antigen recognizing construct according to any of items 1 to 12, wherein the construct is humanized, chimerized and/or murinized.

Item 14: The antigen recognizing construct according to any of items 1 to 13, comprising a binding fragment of a TCR, and wherein said binding fragment comprises CDR1 to CDR3 optionally selected from the CDR1 to CDR3 sequences having the amino acid sequences of SEQ ID NOs: 1, 2, 3; or 7, 8, 9; or 13, 14, 15; or 19, 20, 21; or 25, 26, 27; or 31, 32, 33; or 37, 38, 39; or 43, 44, 45; or 49, 50, 51; or 55, 56, 57; or 61, 62, 63; or 67, 68, 69; or 73, 74, 75; or 79, 80, 81; or 85, 86, 87; or 91, 92, 93; or 97, 98, 99; or 103, 104, 105; or 109, 110, 111; or 115, 116, 117.

Item 15: The antigen recognizing construct according to any of items 1 to 14, wherein the construct is a TCR, or a fragment thereof, composed of at least one TCR α and one TCR β chain sequence, wherein said TCR α chain sequence comprises the CDR1 to CDR3 sequences having the amino acid sequences of SEQ ID NOs: 1 to 3, and said TCR β chain sequence comprises the CDR1 to CDR3 sequences having the amino acid sequences of SEQ ID NOs: 7 to 9; or wherein said TCR α chain sequence comprises the CDR1 to CDR3 sequences having the amino acid sequences of SEQ ID NOs: 13 to 15, and said TCR β chain sequence comprises the CDR1 to CDR3 sequences having the amino acid sequences of SEQ ID NOs: 19 to 21; or wherein said TCR α chain sequence comprises the CDR1 to CDR3 sequences having the amino acid sequences of SEQ ID NOs: 25 to 27, and said TCR β chain sequence comprises the CDR1 to CDR3 sequences having the amino acid sequences of SEQ ID NOs: 31 to 33; or wherein said TCR α chain sequence comprises the CDR1 to CDR3 sequences having the amino acid sequences of SEQ ID NOs: 37 to 39, and said TCR β chain sequence comprises the CDR1 to CDR3 sequences having the amino acid sequences of SEQ ID NOs: 43 to 45; or wherein said TCR α chain sequence comprises the CDR1 to CDR3 sequences having the amino acid sequences of SEQ ID NOs: 49 to 51, and said TCR β chain sequence comprises the CDR1 to CDR3 sequences having the amino acid sequences of SEQ ID NOs: 55 to 57; or wherein said TCR α chain sequence comprises the CDR1 to CDR3 sequences having the amino acid sequences of SEQ ID NOs: 61 to 63, and said TCR β chain sequence comprises the CDR1 to CDR3 sequences having the amino acid sequences of SEQ ID NOs: 67 to 69; or wherein said TCR α chain sequence comprises the CDR1 to CDR3 sequences having the amino acid sequences of SEQ ID NOs: 73 to 75, and said TCR β chain sequence comprises the CDR1 to CDR3 sequences having the amino acid sequences of SEQ ID NOs: 79 to 81; or wherein said TCR α chain sequence comprises the CDR1 to CDR3 sequences having the amino acid sequences of SEQ ID NOs: 85 to 87, and said TCR β chain sequence comprises the CDR1 to CDR3 sequences having the amino acid sequences of SEQ ID NOs: 91 to 93; or wherein said TCR α chain sequence comprises the CDR1 to CDR3 sequences having the amino acid sequences of SEQ ID NOs: 97 to 99, and said TCR β chain sequence comprises the CDR1 to CDR3 sequences having the amino acid sequences of SEQ ID NOs: 103 to 105; or wherein said TCR α chain sequence comprises the CDR1 to CDR3 sequences having the amino acid sequences of SEQ ID NOs: 109 to 111, and said TCR β chain sequence comprises the CDR1 to CDR3 sequences having the amino acid sequences of SEQ ID NOs: 115 to 117.

Item 16: The antigen recognizing construct according to any of items 1 to 15, wherein the construct is a TCR, or a fragment thereof, comprising at least one TCR α and one TCR β chain sequence, wherein said TCR α chain sequence comprises a variable region sequence having the amino acid sequence of SEQ ID NO: 4, and wherein said TCR β chain sequence comprises a variable region sequence having the amino acid sequence of SEQ ID NO: 10; or wherein said TCR α chain sequence comprises a variable region sequence having the amino acid sequence of SEQ ID NO: 16, and wherein said TCR β chain sequence comprises a variable region sequence having the amino acid sequence of SEQ ID NO: 22; or wherein said TCR α chain sequence comprises a variable region sequence having the amino acid sequence of SEQ ID NO: 28, and wherein said TCR β chain sequence comprises a variable region sequence having the amino acid sequence of SEQ ID NO: 34; or wherein said TCR α chain sequence comprises a variable region sequence having the amino acid sequence of SEQ ID NO: 40, and wherein said TCR β chain sequence comprises a variable region sequence having the amino acid sequence of SEQ ID NO: 46; or wherein said TCR α chain sequence comprises a variable region sequence having the amino acid sequence of SEQ ID NO: 52, and wherein said TCR β chain sequence comprises a variable region sequence having the amino acid sequence of SEQ ID NO: 58; or wherein said TCR α chain sequence comprises a variable region sequence having the amino acid sequence of SEQ ID NO: 64, and wherein said TCR β chain sequence comprises a variable region sequence having the amino acid sequence of SEQ ID NO: 70; or wherein said TCR α chain sequence comprises a variable region sequence having the amino acid sequence of SEQ ID NO: 76, and wherein said TCR β chain sequence comprises a variable region sequence having the amino acid sequence of SEQ ID NO: 82; or wherein said TCR α chain sequence comprises a variable region sequence having the amino acid sequence of SEQ ID NO: 88, and wherein said TCR β chain sequence comprises a variable region sequence having the amino acid sequence of SEQ ID NO: 94; or wherein said TCR α chain sequence comprises a variable region sequence having the amino acid sequence of SEQ ID NO: 100, and wherein said TCR β chain sequence comprises a variable region sequence having the amino acid sequence of SEQ ID NO: 106; or wherein said TCR α chain sequence comprises a variable region sequence having the amino acid sequence of SEQ ID NO: 112, and wherein said TCR β chain sequence comprises a variable region sequence having the amino acid sequence of SEQ ID NO: 118.

Item 17: The antigen recognizing construct according to any of items 1 to 16, wherein the construct is a TCR, or a fragment thereof, further comprising a TCR constant region having at least 50%, 60%, 70%, 80%, 90%, 95%, 98%, 99%, or 100% sequence identity to an amino acid sequence selected from SEQ ID NOs: 5, 11, 17, 23, 29, 35, 41, 47, 53, 59, 65, 71, 77, 83, 89, 95, 101, 107, 113, and 119, preferably wherein the TCR is composed of at least one TCR α and one TCR β chain sequence, wherein the TCR α chain sequence comprises a constant region having at least 50%, 60%, 70%, 80%, 90%, 95%, 98%, 99%, or 100% sequence identity to an amino acid sequence selected from SEQ ID NOs: 5, 17, 29, 41, 53, 65, 77, 89, 101, and 113; and wherein the TCR β chain sequence comprises a constant region having at least 50%, 60%, 70%, 80%, 90%, 95%, 98%, 99%, or 100% sequence identity to an amino acid sequence selected from SEQ ID NOs: 11, 23, 35, 47, 59, 71, 83, 95, 107, and 119.

Item 18: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 6, and a second TCR chain having at least 50%, 60%, 70%, 80%, 90%, 95%, 98%, 99%, or 100% sequence identity to the amino acid sequence of SEQ ID NO: 12.

Item 19: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 18, and a second TCR chain having at least 50%, 60%, 70%, 80%, 90%, 95%, 98%, 99%, or 100% sequence identity to the amino acid sequence of SEQ ID NO: 24.

Item 20: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 30, and a second TCR chain having at least 50%, 60%, 70%, 80%, 90%, 95%, 98%, 99%, or 100% sequence identity to the amino acid sequence of SEQ ID NO: 36.

Item 20b: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 42, and a second TCR chain having at least 50%, 60%, 70%, 80%, 90%, 95%, 98%, 99%, or 100% sequence identity to the amino acid sequence of SEQ ID NO: 48.

Item 20c: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 54, and a second TCR chain having at least 50%, 60%, 70%, 80%, 90%, 95%, 98%, 99%, or 100% sequence identity to the amino acid sequence of SEQ ID NO: 60.

Item 20d: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO:66, and a second TCR chain having at least 50%, 60%, 70%, 80%, 90%, 95%, 98%, 99%, or 100% sequence identity to the amino acid sequence of SEQ ID NO: 72.

Item 20e: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 78, and a second TCR chain having at least 50%, 60%, 70%, 80%, 90%, 95%, 98%, 99%, or 100% sequence identity to the amino acid sequence of SEQ ID NO: 84.

Item 20f: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 90, and a second TCR chain having at least 50%, 60%, 70%, 80%, 90%, 95%, 98%, 99%, or 100% sequence identity to the amino acid sequence of SEQ ID NO: 96.

Item 20g: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 102, and a second TCR chain having at least 50%, 60%, 70%, 80%, 90%, 95%, 98%, 99%, or 100% sequence identity to the amino acid sequence of SEQ ID NO: 108.

Item 20h: The antigen recognizing construct according to any of items 1 to 17, comprising a first TCR chain having at least 50%, 60%, 70%, 80%, 90%, 95%, 98%, 99%, or 100% sequence identity to the amino acid sequence of SEQ ID NO: 114, and a second TCR chain having at least 50%, 60%, 70%, 80%, 90%, 95%, 98%, 99%, or 100% sequence identity to the amino acid sequence of SEQ ID NO: 120.

Item 21: A nucleic acid encoding for an antigen recognizing construct according to any one of items 1 to 20.

Item 22: A vector comprising a nucleic acid according to item 21.

Item 23: A host cell comprising an antigen recognizing construct according to any one of items 1 to 20, or a nucleic acid according to item 21, or a vector according to item 22.

Item 24: The host cell according to item 23, wherein the cell is a lymphocyte, preferably a T lymphocyte or T lymphocyte progenitor, more preferably a CD4 or CD8 positive T-cell.

Item 25: A pharmaceutical composition comprising the antigen recognizing construct according to any of items 1 to 20, or the nucleic acid according to item 21, or the vector according to item 22, or the host cell according to item 23 or 24, and a pharmaceutical acceptable carrier, stabilizer and/or excipient.

Item 26: The antigen recognizing construct according to any one of items 1 to 20, or a nucleic acid according to item 21, or a vector according to item 22, or a host cell according to item 23 or 24, or the pharmaceutical composition according to item 25, for use in medicine.

Item 27: The antigen recognizing construct, or the nucleic acid, or the vector, or the host cell, or the pharmaceutical composition, for use according to item 26, for use in the diagnosis, prevention, and/or treatment of a proliferative disease, wherein the disease comprises a malignant or benign tumor disease.

Item 28: The antigen recognizing construct, or the nucleic acid, or the vector, or the host cell, or the pharmaceutical composition, for use according to item 27, wherein the tumor disease is characterized by the expression of TAA in a tumor cell of the tumor disease.

Item 29: The antigen recognizing construct, or the nucleic acid, or the vector, or the host cell, or the pharmaceutical composition, for use according to any one of items 26 to 28, wherein the use in medicine is a use in immune therapy optionally comprising an adoptive cell transfer, wherein the immune therapy comprises adoptive autologous or heterologous T-cell therapy.

Item 30: A method of manufacturing a TAA specific antigen recognizing construct expressing cell line, comprising
a., providing a suitable host cell,
b., providing a genetic construct comprising a coding sequence encoding the antigen recognizing construct according to any of items 1 to 20,
c., introducing into said suitable host cell said genetic construct,
d., expressing said genetic construct by said suitable host cell.

Item 31: The method according to item 30, further comprising cell surface presentation of said antigen recognizing construct.

Item 32: The method according to item 30 or 31, wherein the genetic construct is an expression construct comprising a promoter sequence operably linked to said coding sequence.

Item 33: The method according to any one of items 30 to 32, wherein said antigen recognizing construct is of mammalian origin, preferably of human origin.

Item 34: The method according to any one of items 30 to 33, wherein said suitable host cell is a mammalian cell, optionally selected from a human cell or a human T lymphocyte.

Item 35: The method according to any of items 30 to 34, wherein said antigen recognizing construct is a modified TCR, wherein said modification comprises addition of a functional domain comprising a label, or an alternative domain comprising a membrane anchor domain.

Item 36: The method according to item 35, wherein said antigen recognizing construct is an alpha/beta TCR, gamma/delta TCR, or a single chain TCR (scTCR).

Item 37: The method according to any of items 30 to 36, wherein said genetic construct is introduced into said suitable host cell by retroviral transfection.

Item 38: The method according to any of items 30 to 37, further comprising the isolation and purification of the antigen recognizing construct from the suitable host cell and, optionally, reconstitution of the antigen recognizing construct in a T-cell.

The present invention will now be further described in the following examples with reference to the accompanying figures and sequences, nevertheless, without being limited thereto. For the purposes of the present invention, all references as cited herein are incorporated by reference in their entireties. In the Figures and Sequences:

FIG. 1: IFNγ release from CD8+ T-cells electroporated with alpha and beta chain RNA of TCR R39P1C12 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 2:
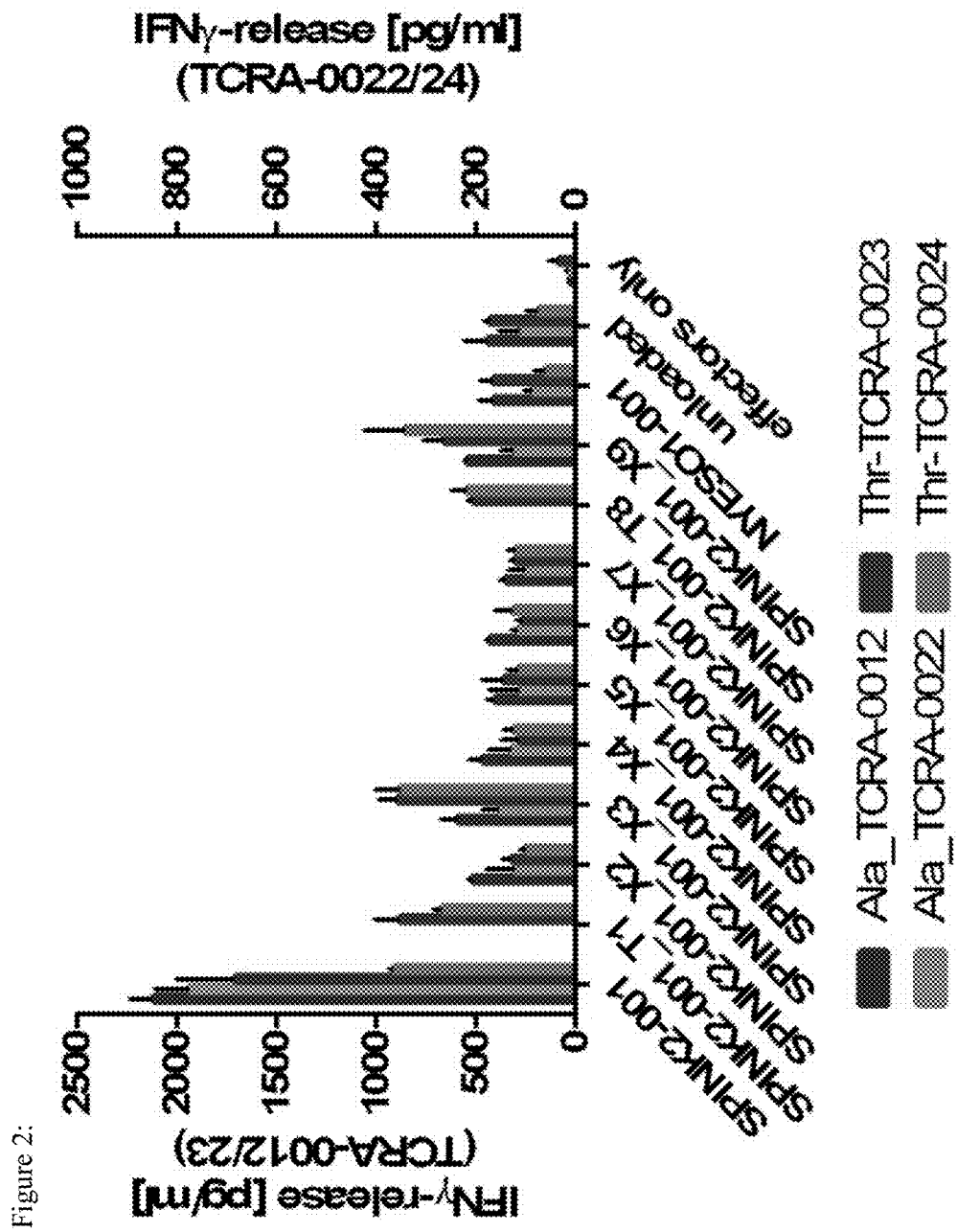

FIG. 2: IFNγ release from CD8+ T-cells electroporated with alpha and beta chain RNA of TCR R39P1F5 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 3:
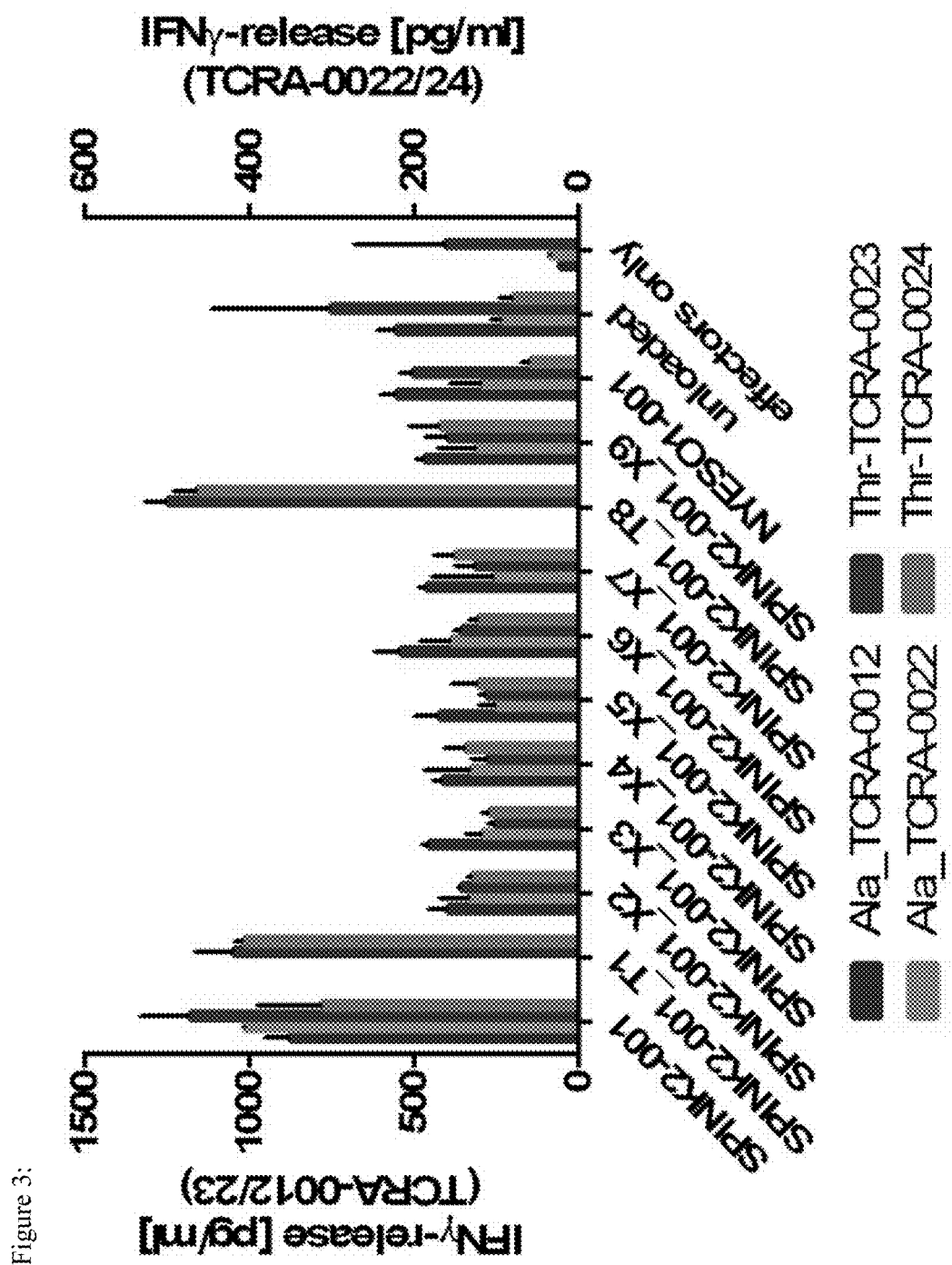

FIG. 3: IFNγ release from CD8+ T-cells electroporated with alpha and beta chain RNA of TCR R40P1C2 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 4:
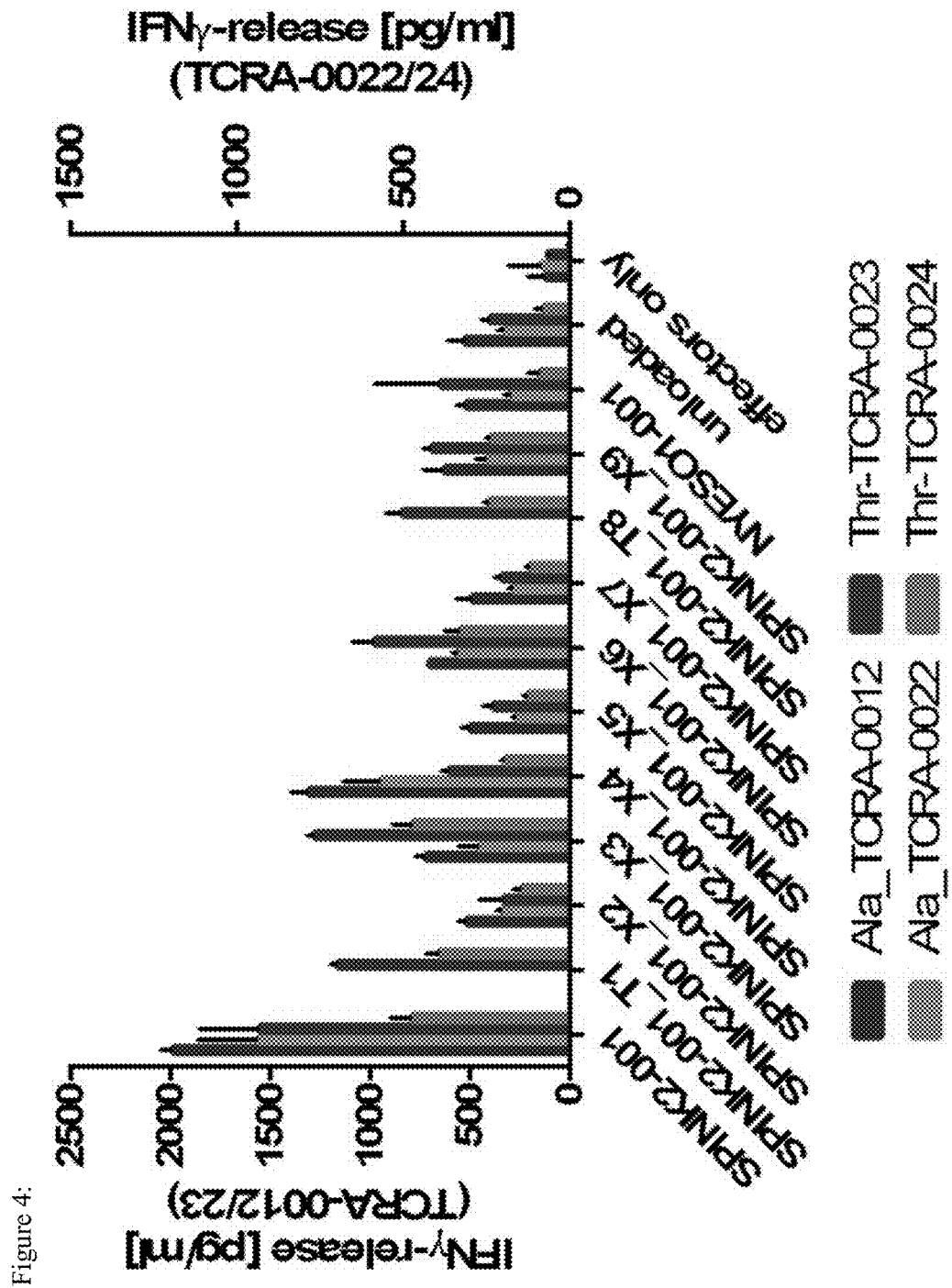

FIG. 4: IFNγ release from CD8+ T-cells electroporated with alpha and beta chain RNA of TCR R41P3E6 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 5:
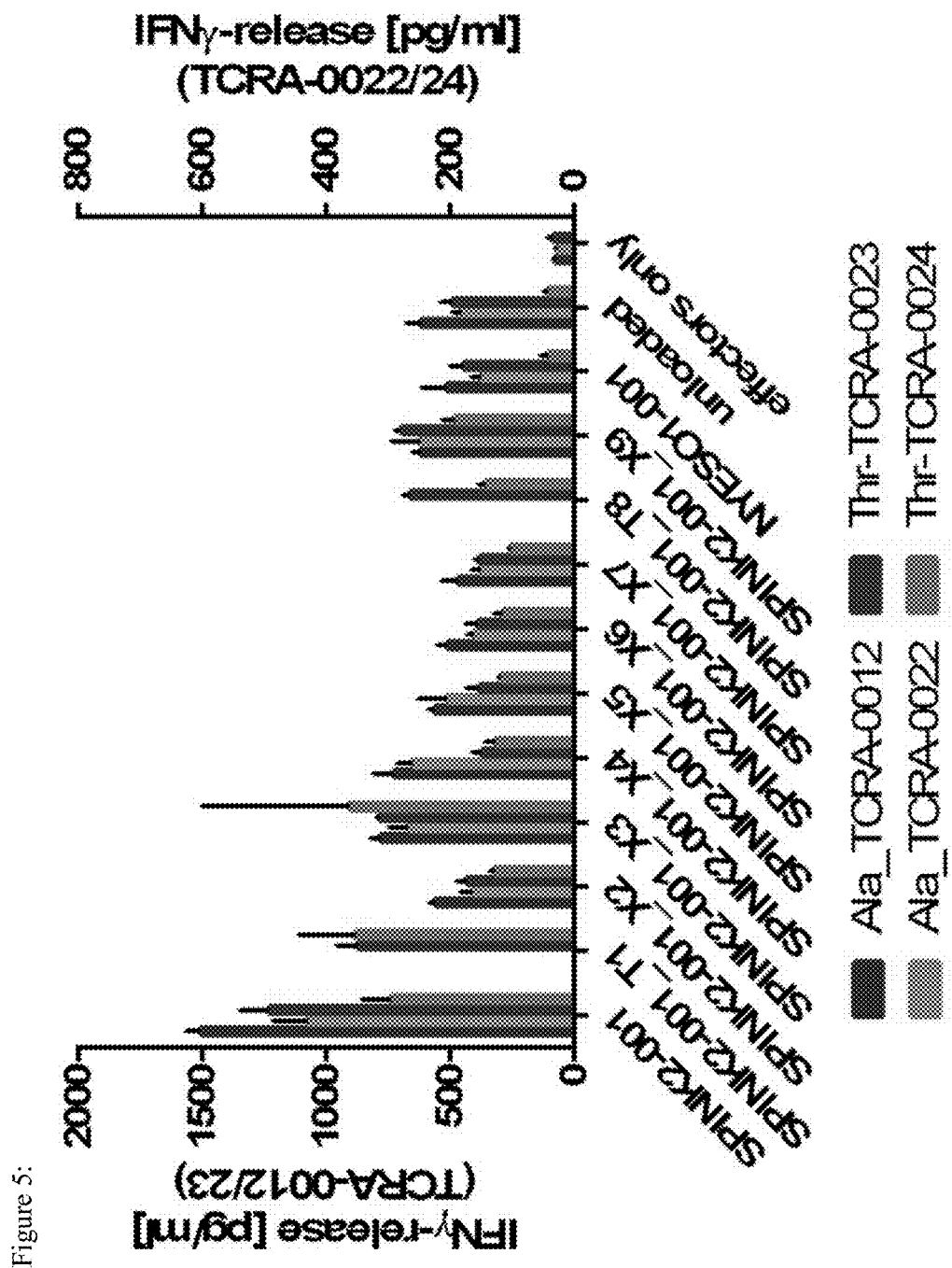

FIG. 5: IFNγ release from CD8+ T-cells electroporated with alpha and beta chain RNA of TCR R43P3G4 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 6:
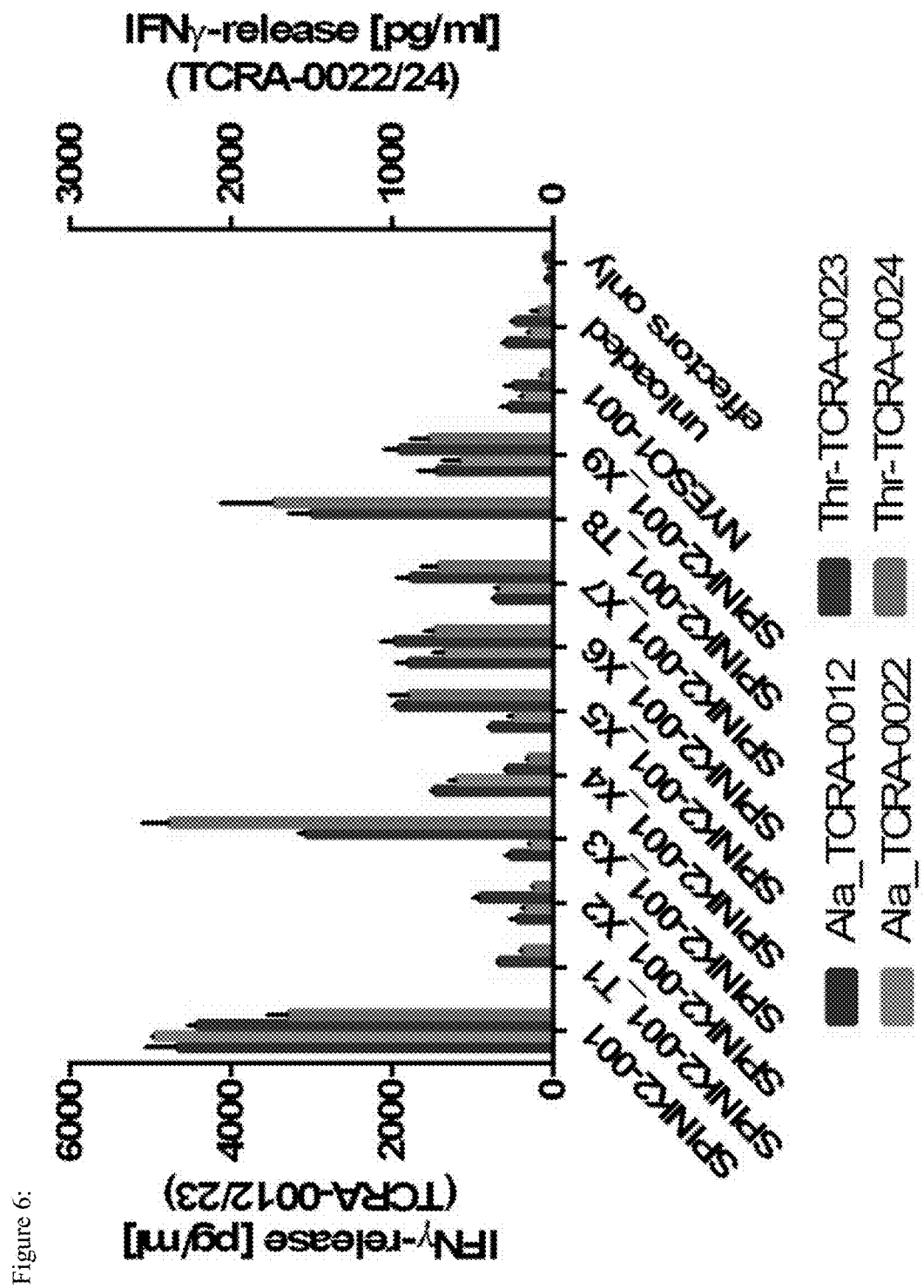

FIG. 6: IFNγ release from CD8+ T-cells electroporated with alpha and beta chain RNA of TCR R44P3B3 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 7:
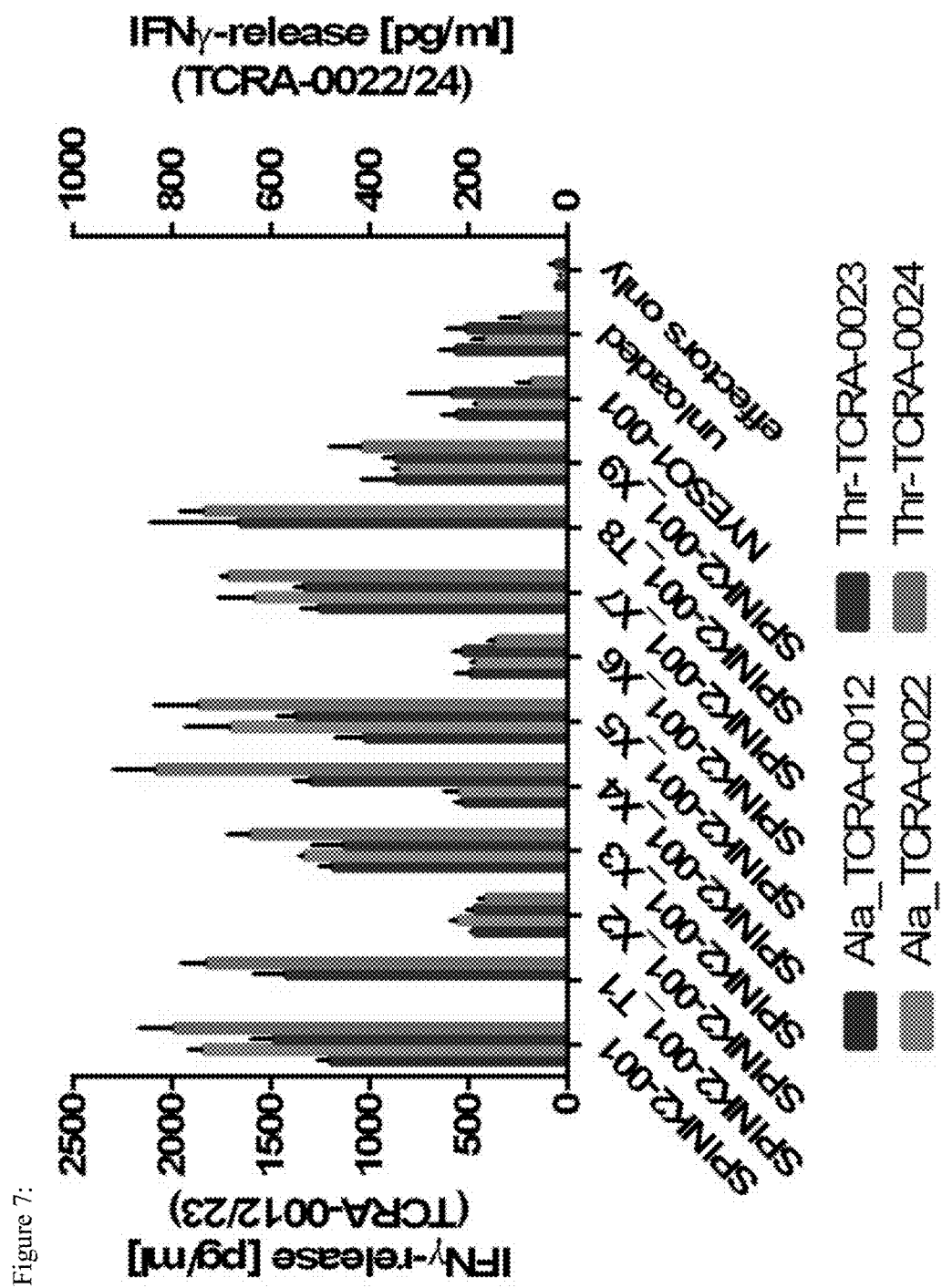

FIG. 7: IFNγ release from CD8+ T-cells electroporated with alpha and beta chain RNA of TCR R44P3E7 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 8:
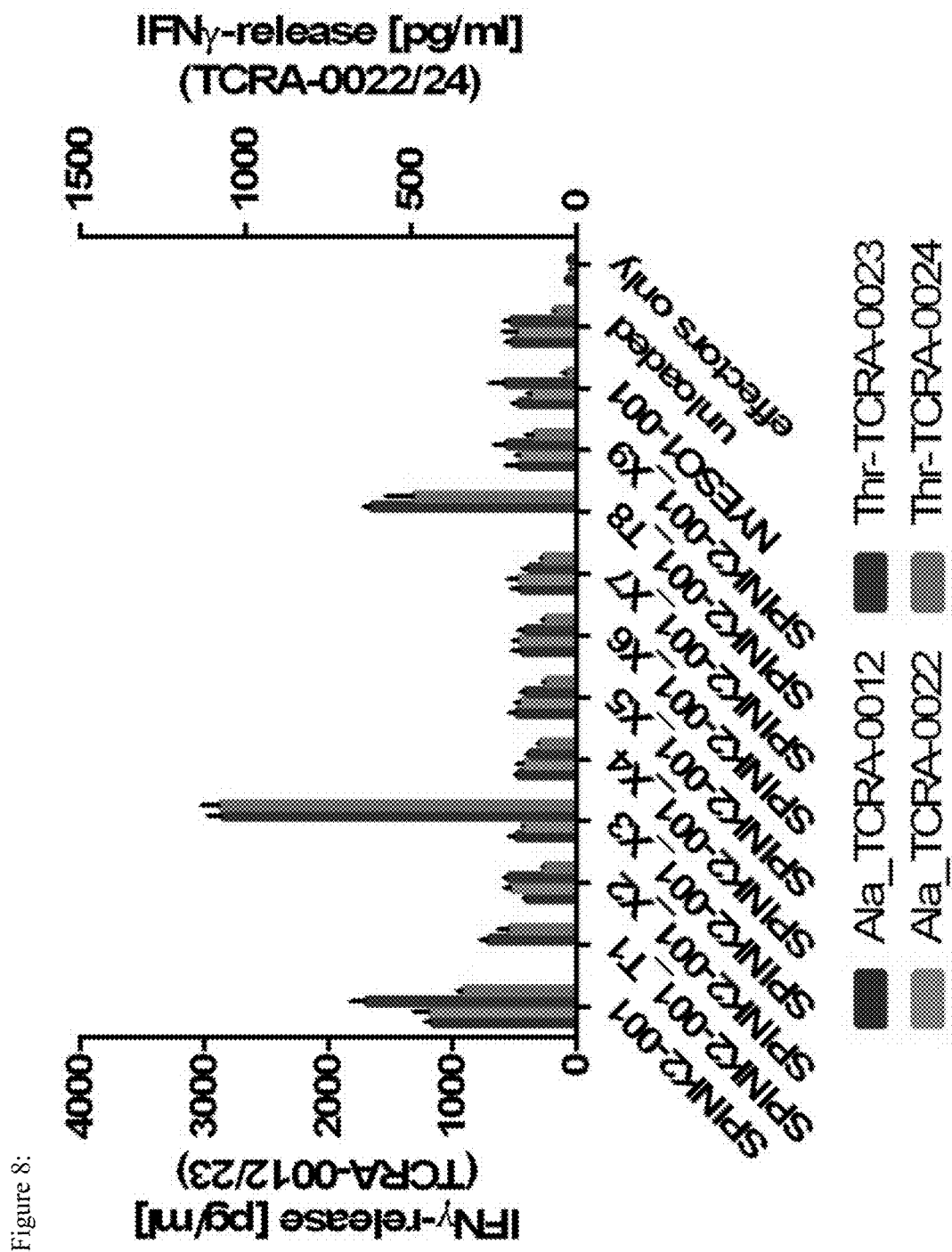

FIG. 8: IFNγ release from CD8+ T-cells electroporated with alpha and beta chain RNA of TCR R49P2B7 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 9:
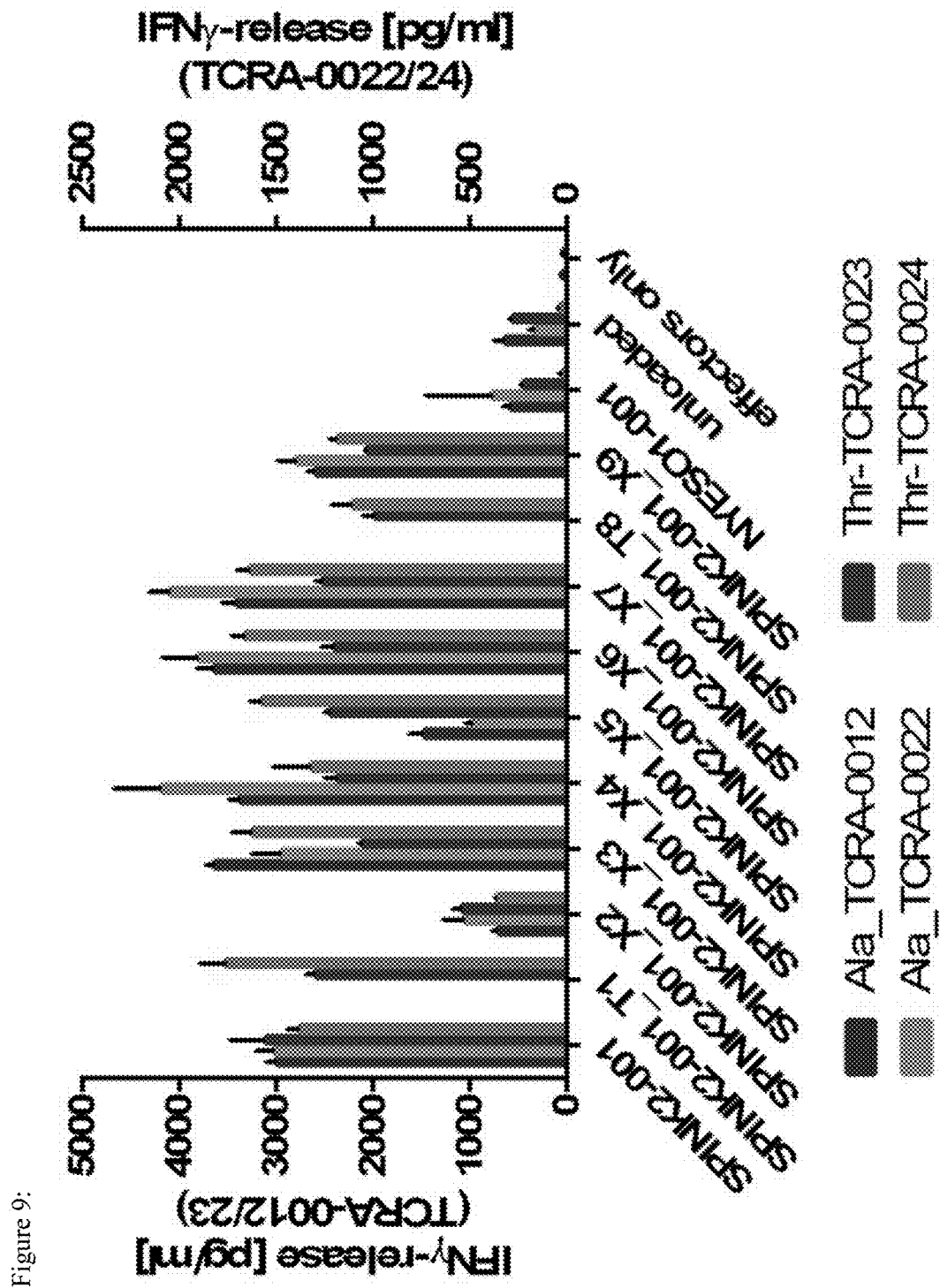

FIG. 9: IFNγ release from CD8+ T-cells electroporated with alpha and beta chain RNA of TCR R55P1G7 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 10:
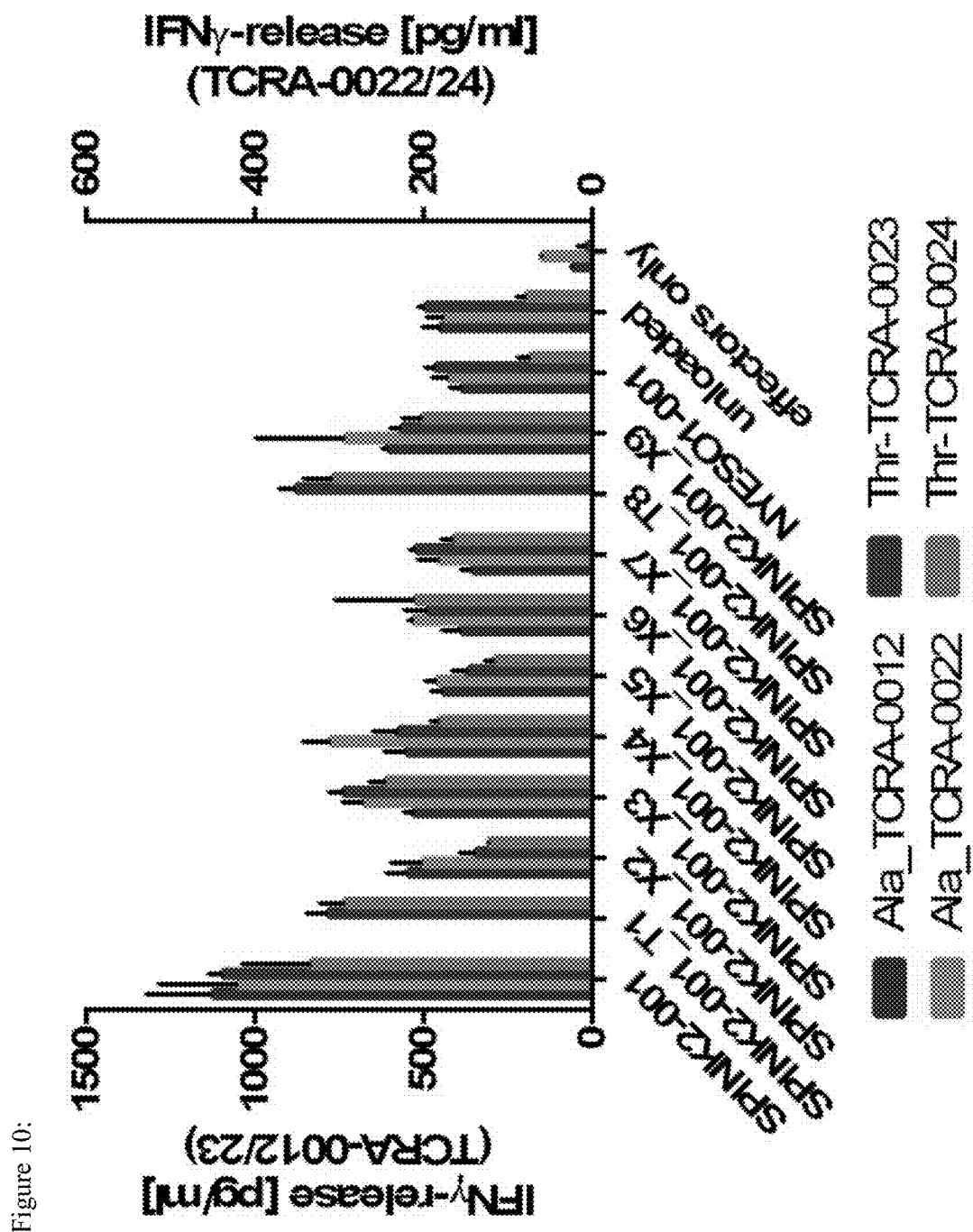

FIG. 10: IFNγ release from CD8+ T-cells electroporated with alpha and beta chain RNA of TCR R59P2A7 (Table 1) after co-incubation with T2 target cells loaded with SPINK2-001 peptide (SEQ ID NO:133) or various SPINK2-001 alanine- or threonine-substitution variants at positions 1-9 of SEQ ID NO:133 (SEQ ID NOs:134-149) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 11:
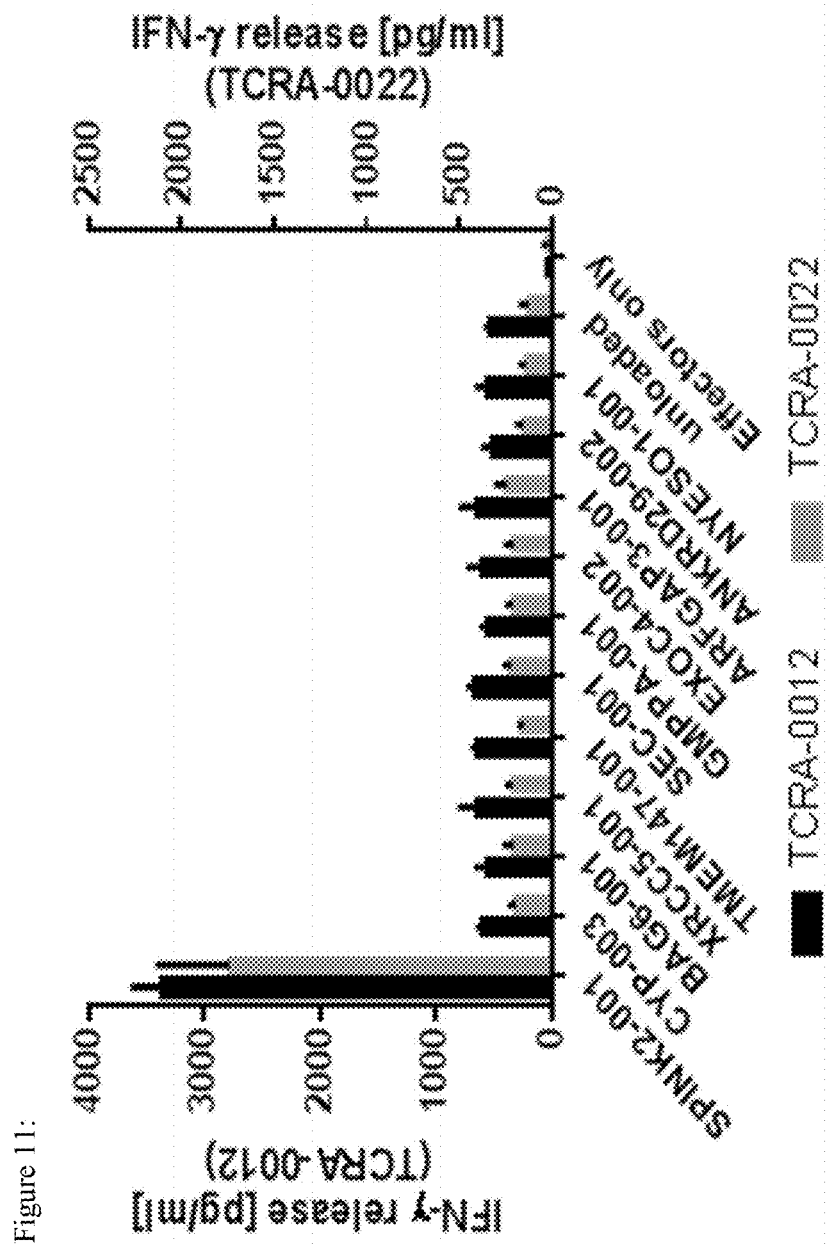

FIG. 11: IFNγ release from CD8+ T-cells electroporated with alpha and beta chain RNA of TCRs R39P1C12 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 12:
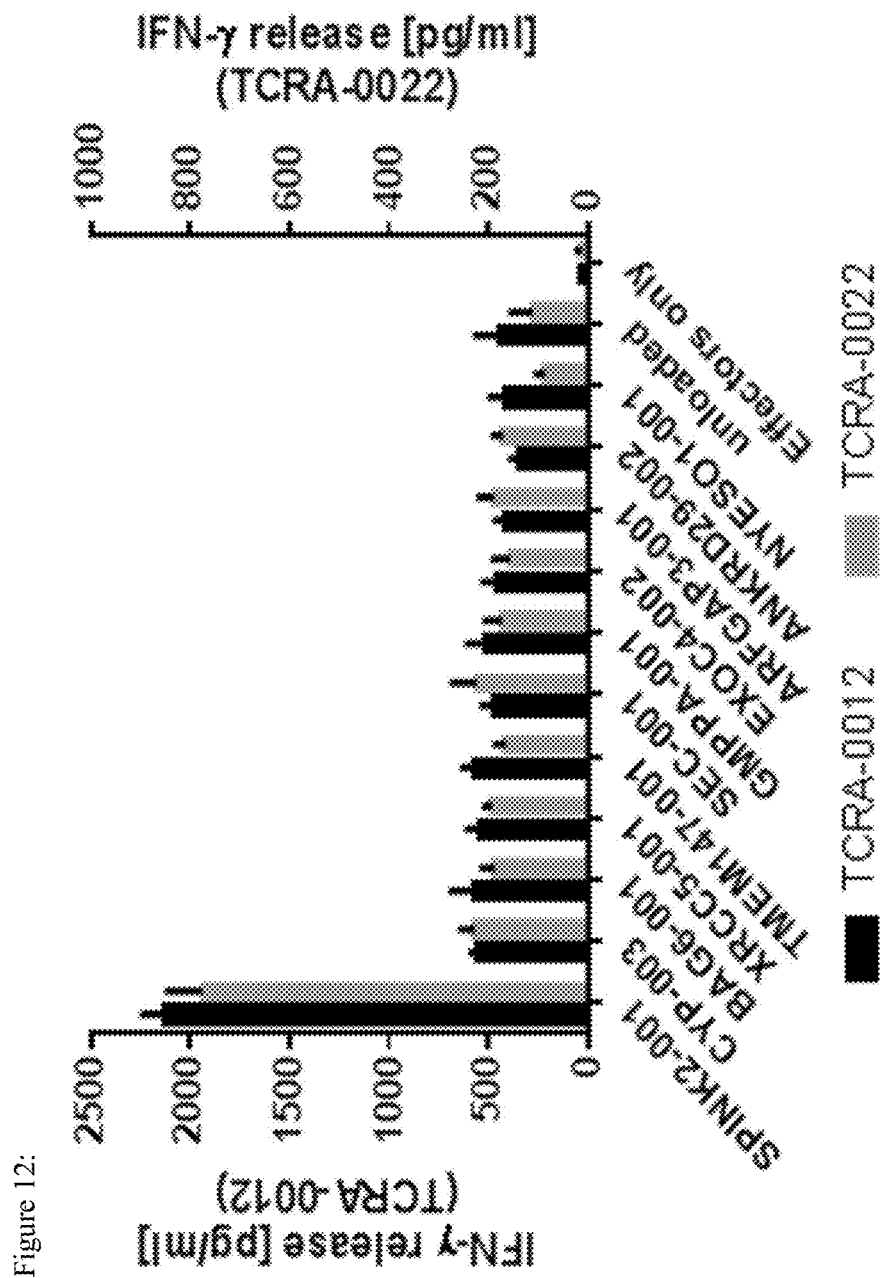

FIG. 12: IFNγ release from CD8+ T-cells electroporated with alpha and beta chain RNA of TCRs R39P1F5 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 13:
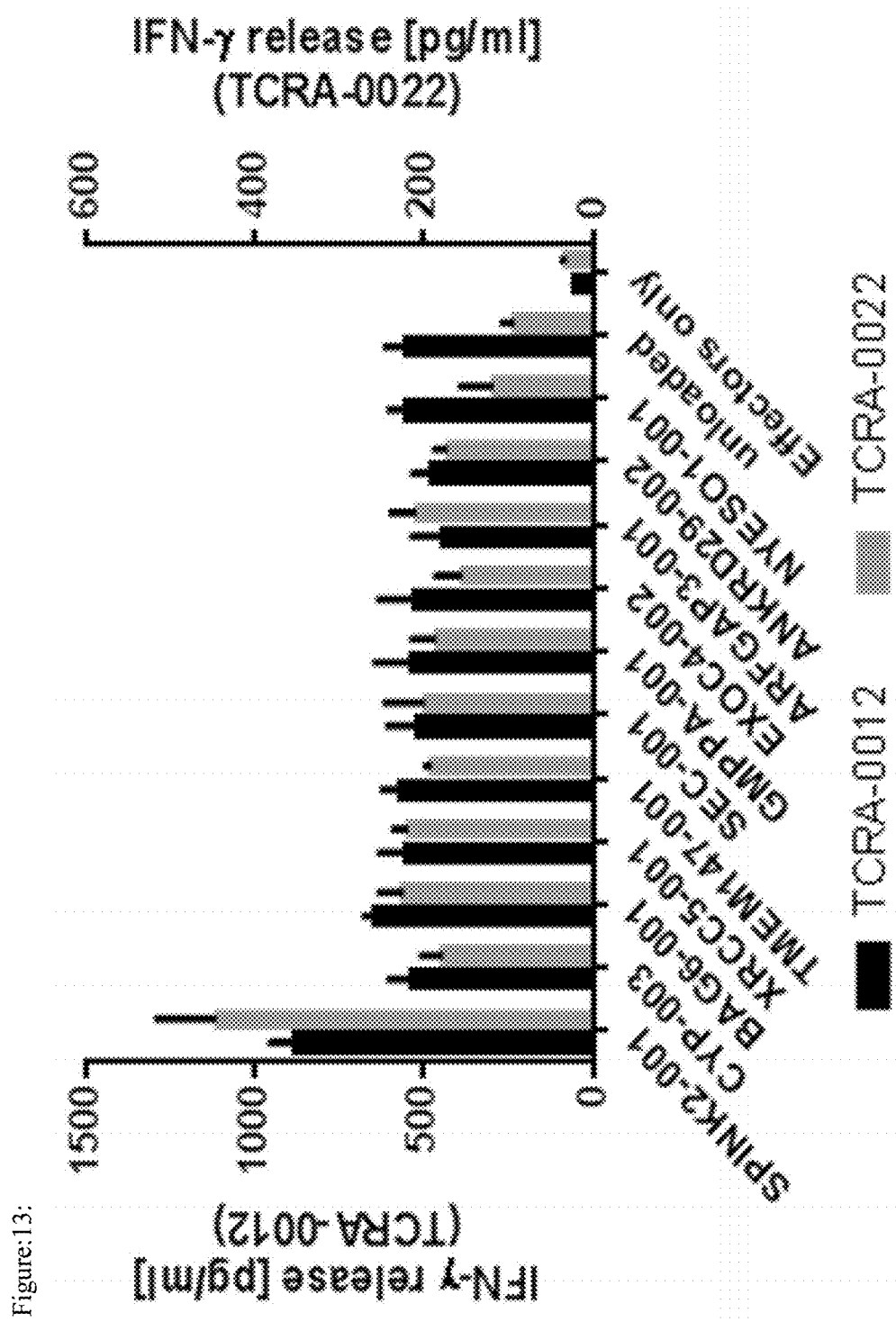

FIG. 13: IFNγ release from CD8+ T-cells electroporated with alpha and beta chain RNA of TCRs R40P1C2 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 14:
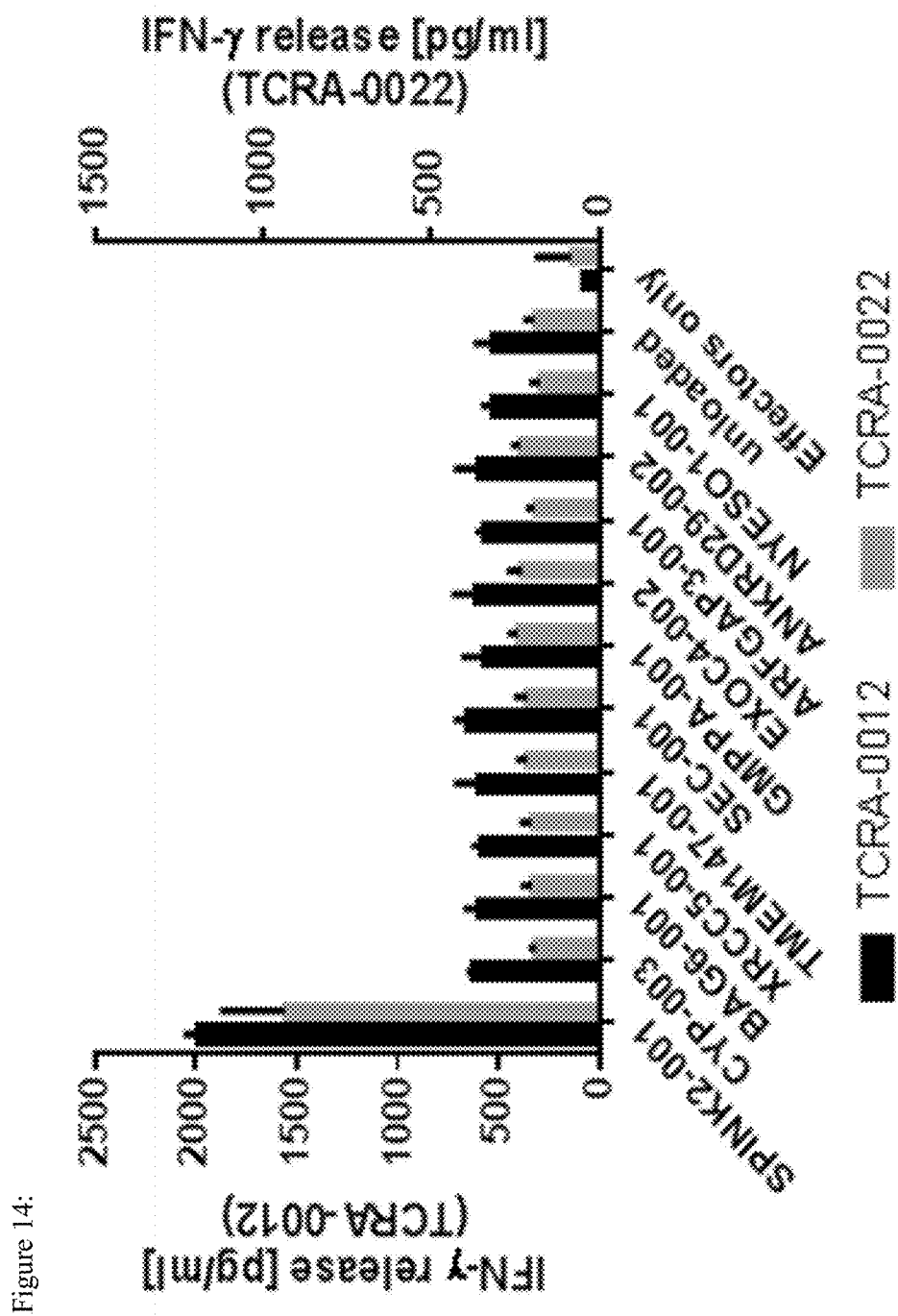

FIG. 14: IFNγ release from CD8+ T-cells electroporated with alpha and beta chain RNA of TCRs R41P3E6 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 15:
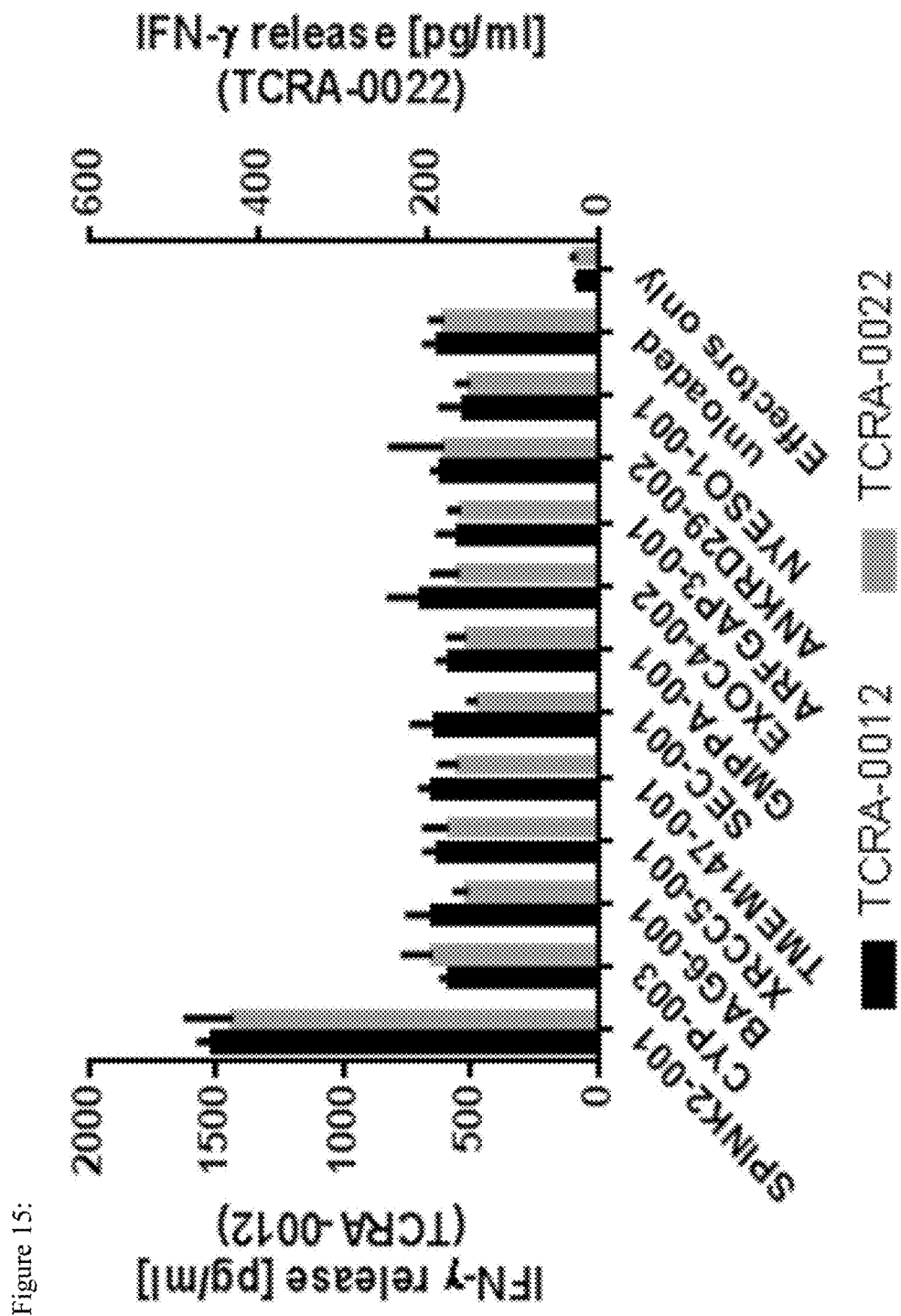

FIG. 15: IFNγ release from CD8+ T-cells electroporated with alpha and beta chain RNA of TCRs R43P3G4 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 16:
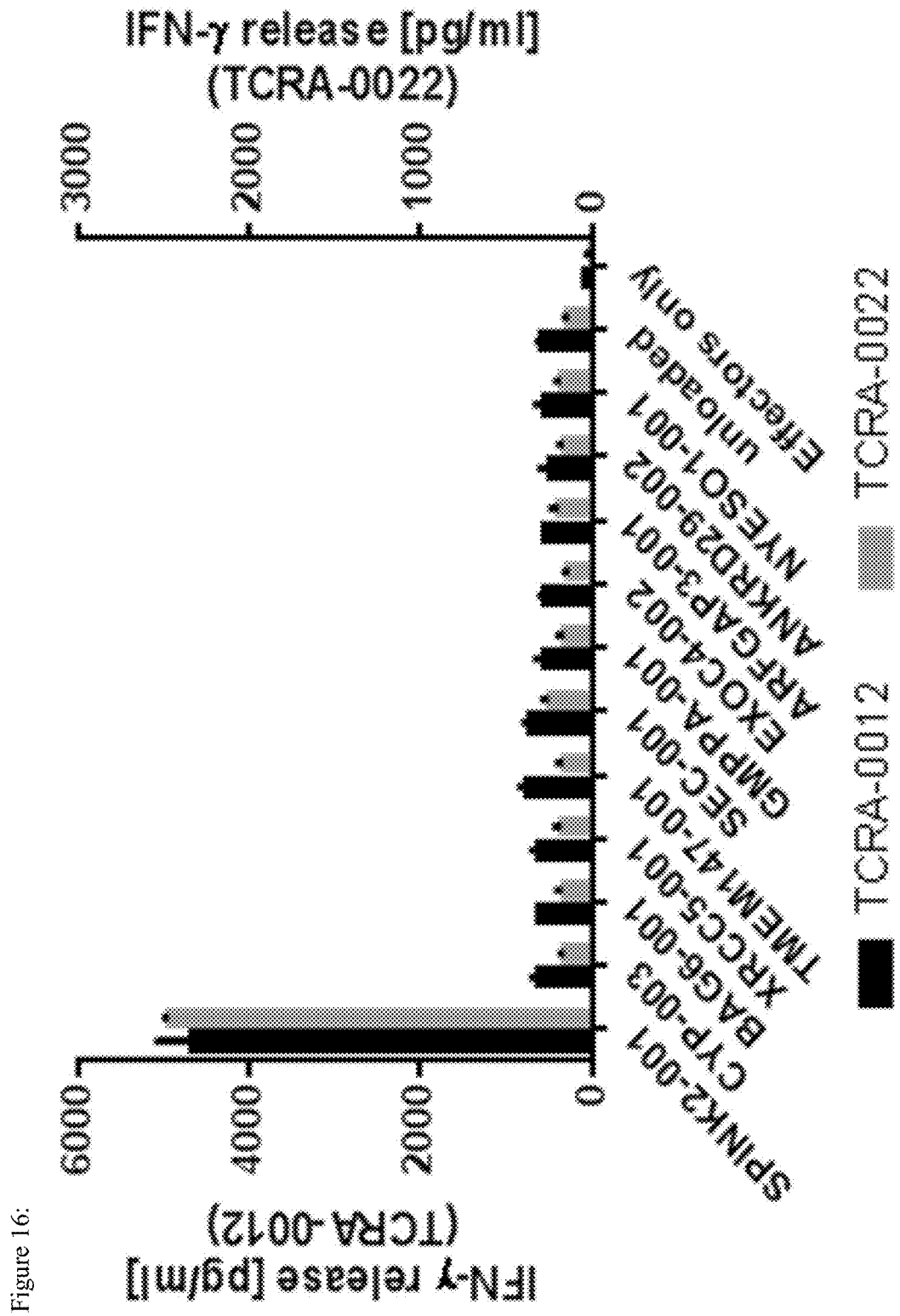

FIG. 16: IFNγ release from CD8+ T-cells electroporated with alpha and beta chain RNA of TCRs R44P3B3 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 17:
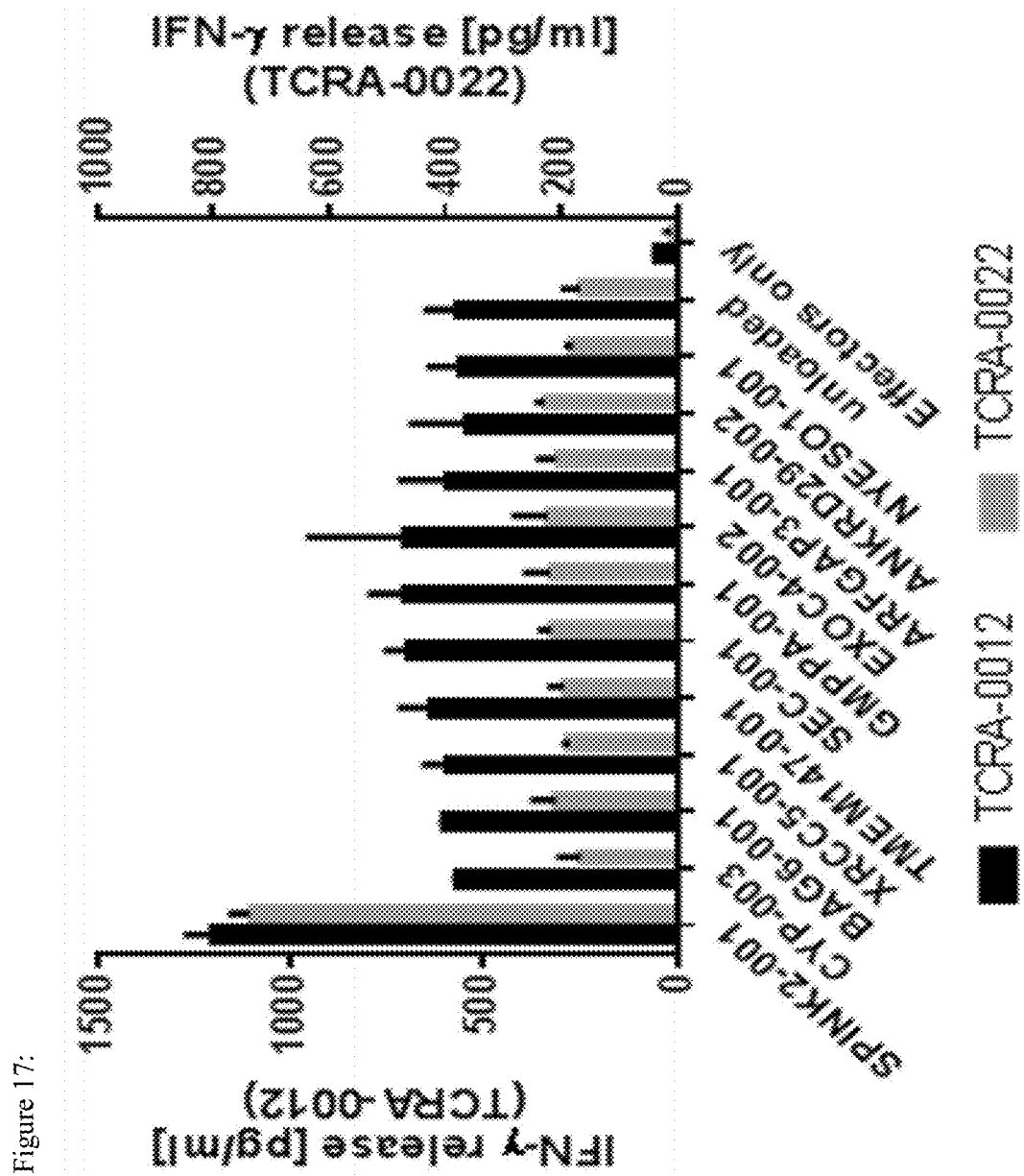

FIG. 17: IFNγ release from CD8+ T-cells electroporated with alpha and beta chain RNA of TCRs R44P3E7 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 18:
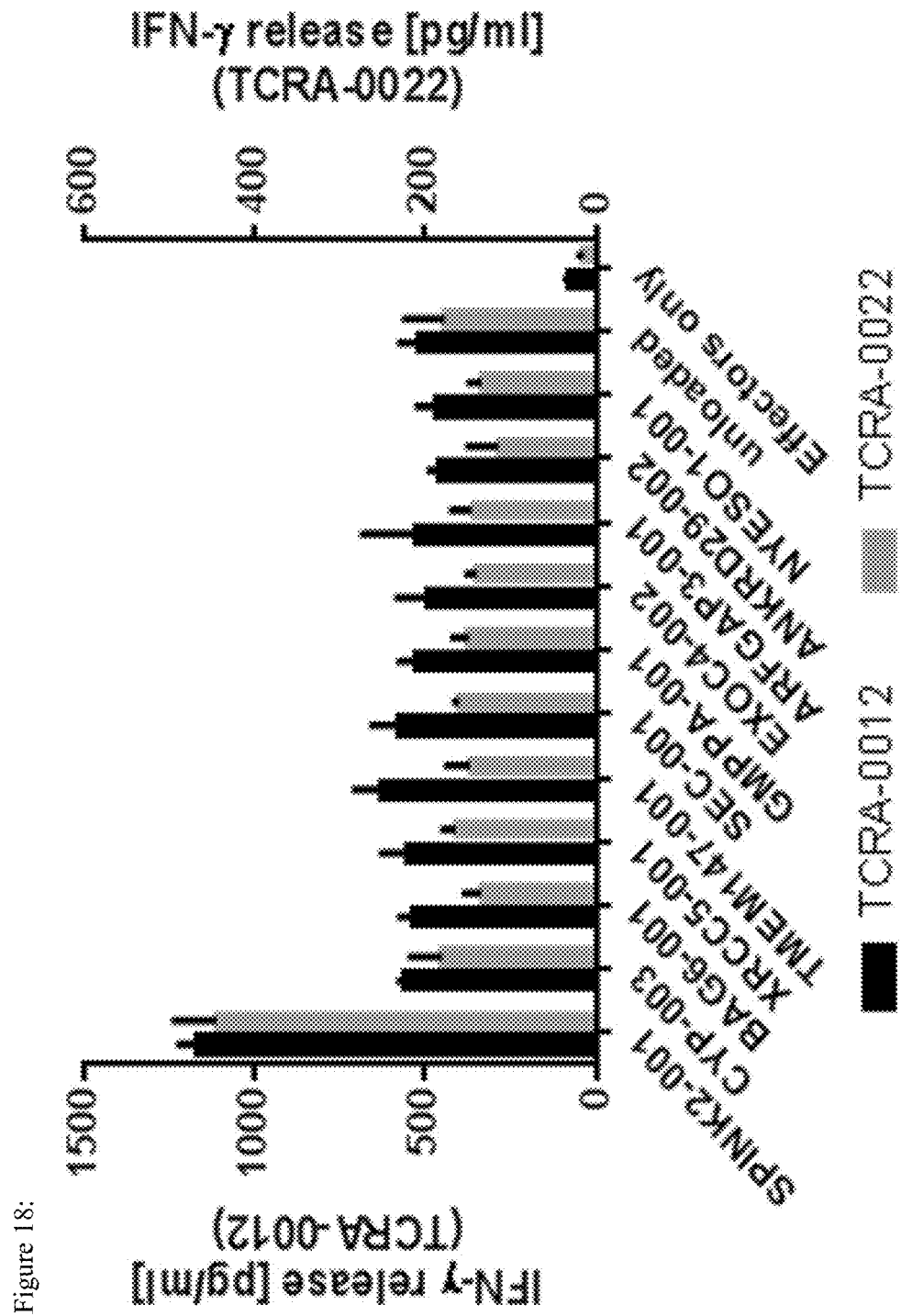

FIG. 18: IFNγ release from CD8+ T-cells electroporated with alpha and beta chain RNA of TCRs R49P2B7 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 19:
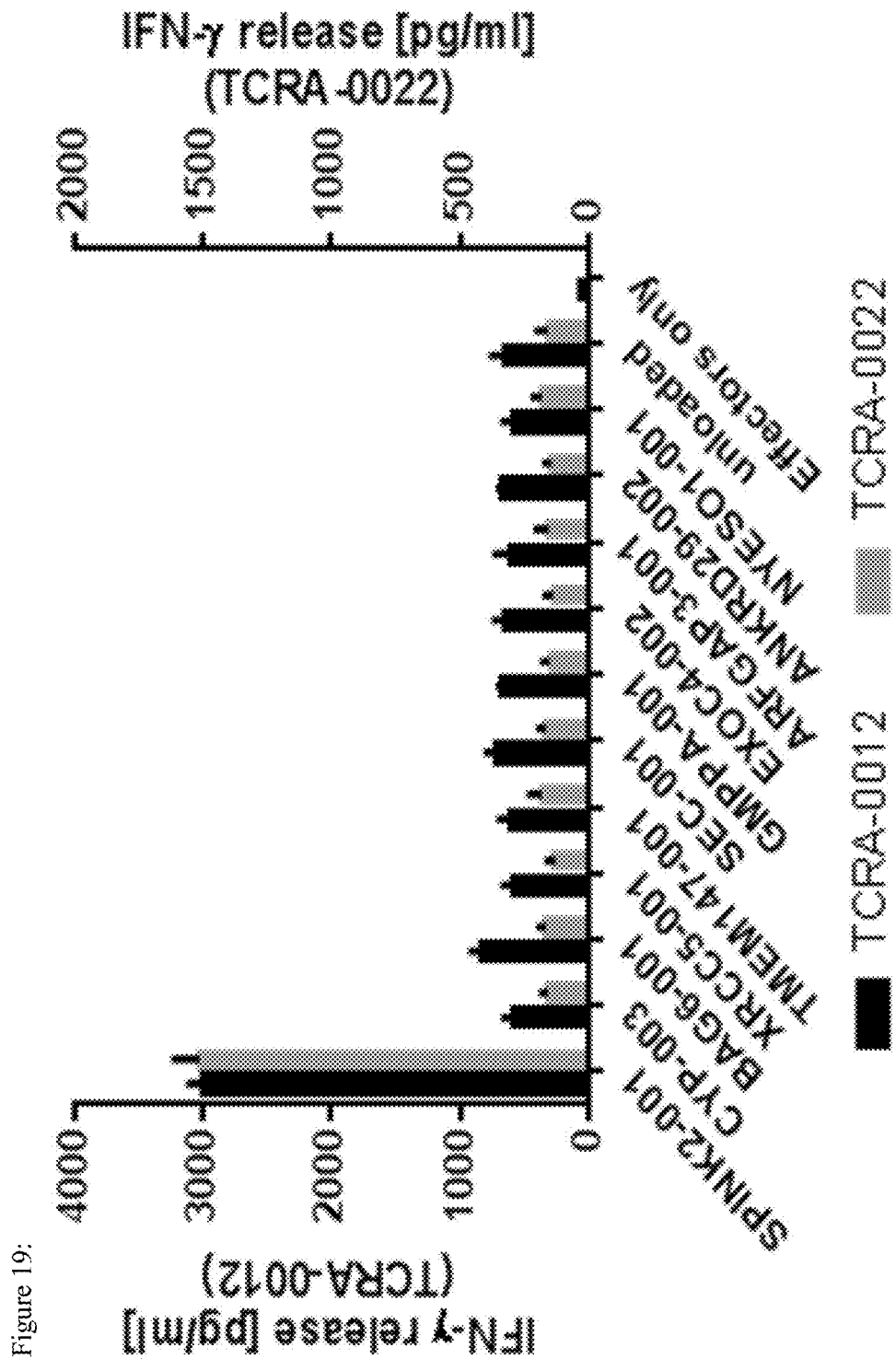

FIG. 19: IFNγ release from CD8+ T-cells electroporated with alpha and beta chain RNA of TCRs R55P1G7 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 20:
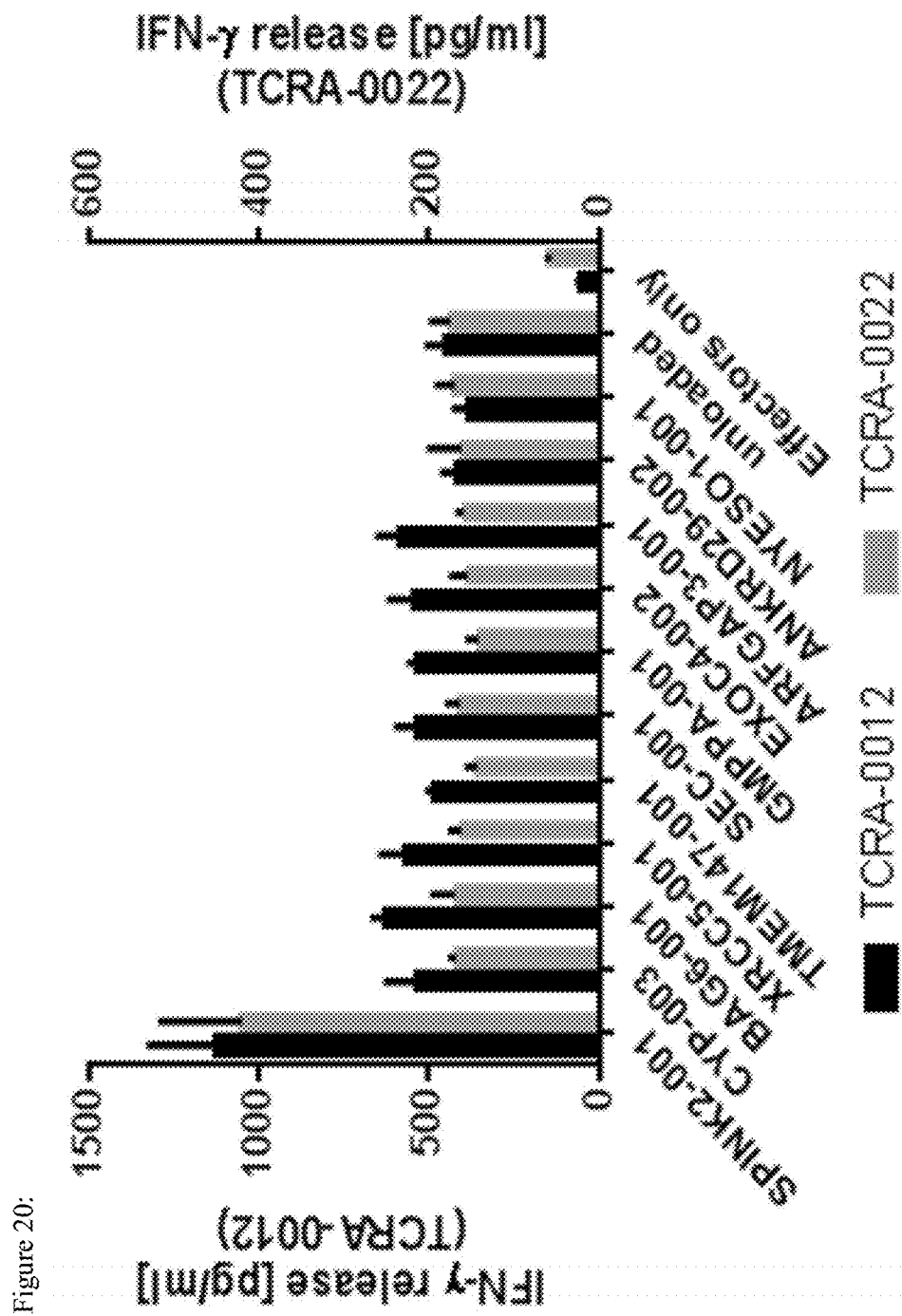

FIG. 20: IFNγ release from CD8+ T-cells electroporated with alpha and beta chain RNA of TCRs R59P2A7 (Table 1) after co-incubation with T2 target cells loaded with SPINK2-001 peptide (SEQ ID NO:133) or homologous but unrelated peptide CYP-003 (SEQ ID NO:150), BAG6-001 (SEQ ID NO:151), XRCC5-001 (SEQ ID NO:152), TMEM147-001 (SEQ ID NO:153), SEC-001 (SEQ ID NO:154), GMPPA-001 (SEQ ID NO:155), EXOC4-002 (SEQ ID NO:156), ARFGAP3-001 (SEQ ID NO:157) or ANKRD29-002 (SEQ ID NO:158) or control peptide NYESO1-001 (SEQ ID NO:159). IFNγ release data were obtained with CD8+ T-cells derived from two different healthy donors. RNA electroporated CD8+ T-cells alone or in co-incubation with unloaded target cells served as controls.

Figure 21:
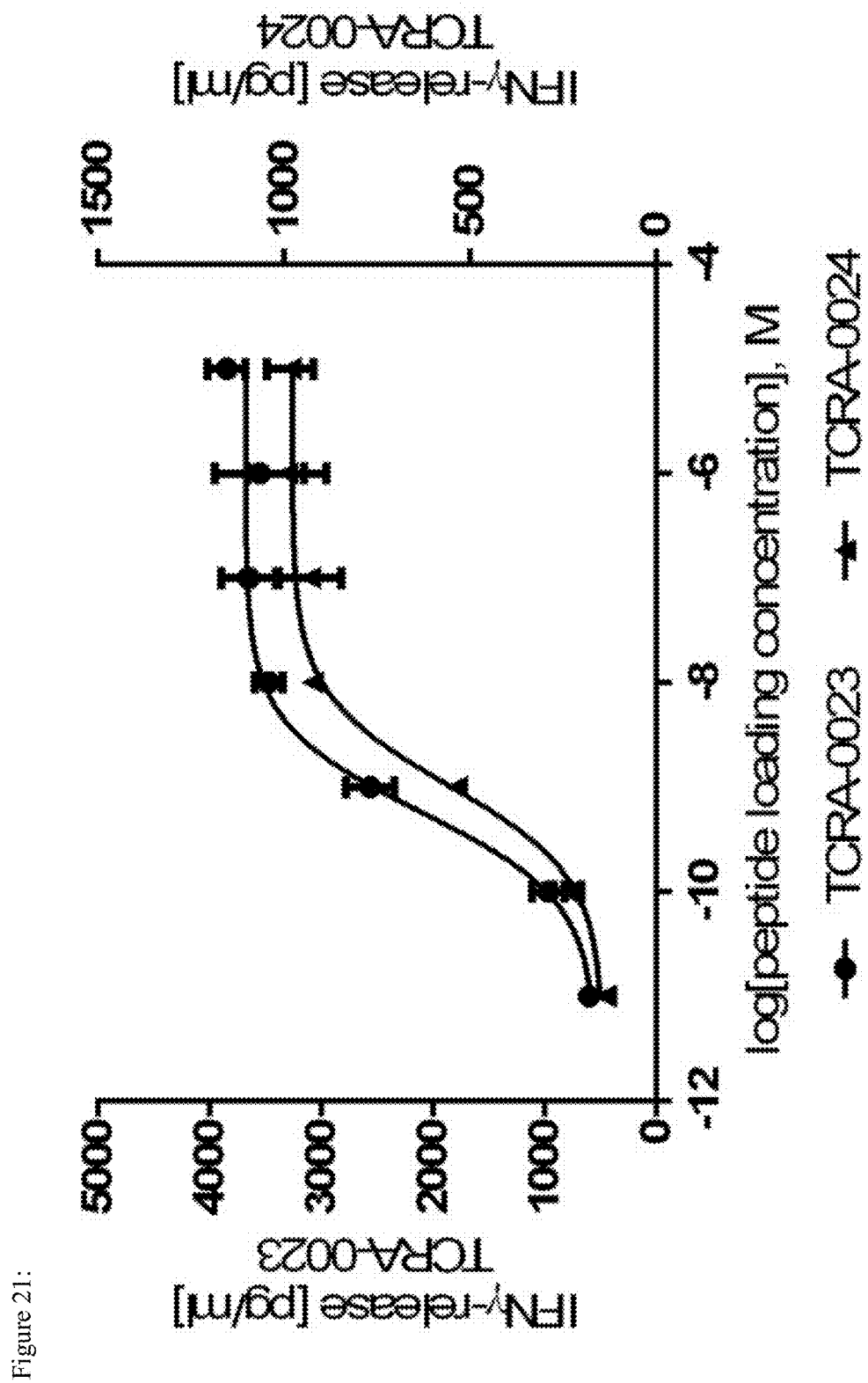

FIG. 21: IFNγ release from CD8+ T-cells electroporated with alpha and beta chain RNA of TCR R39P1C12 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 22:
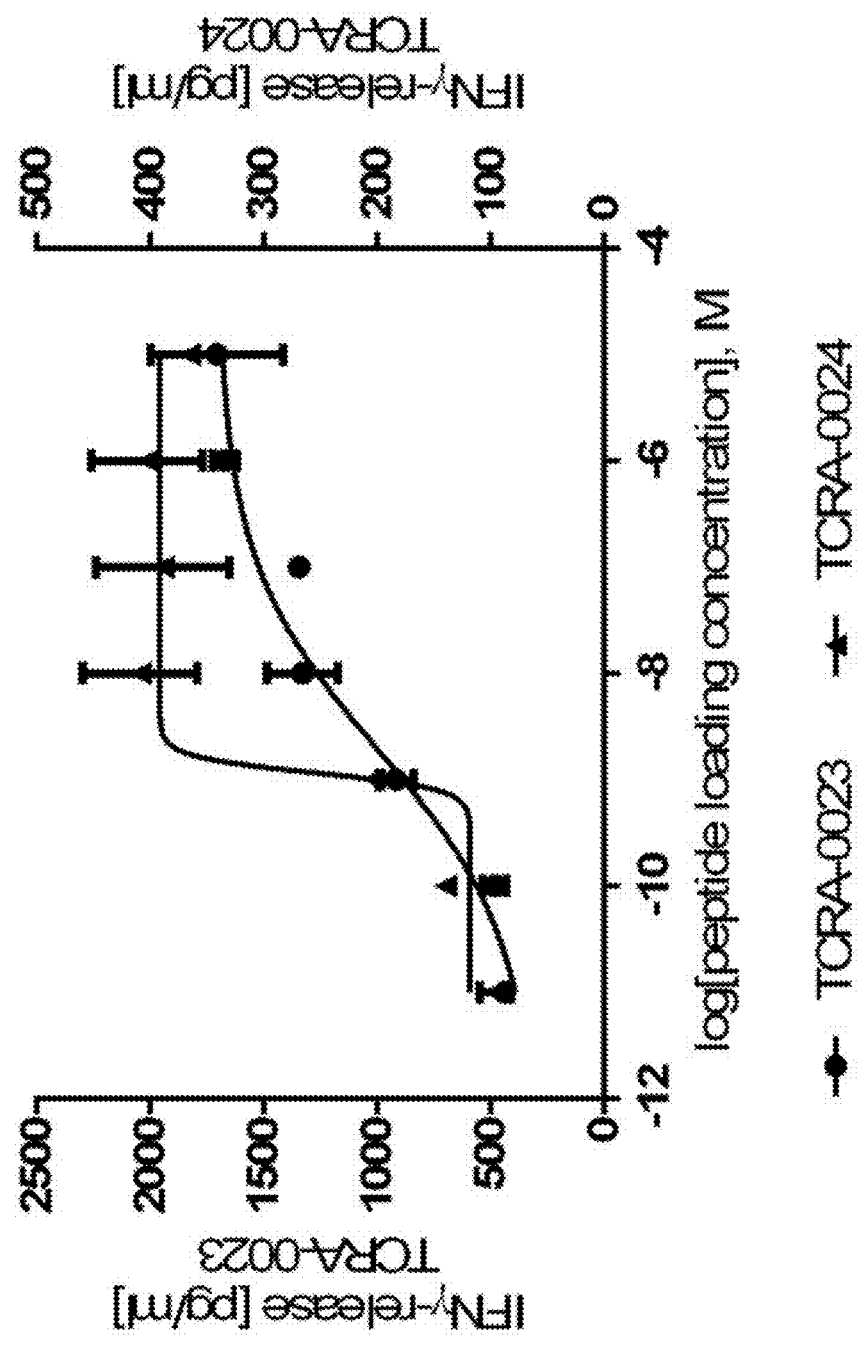

FIG. 22: IFNγ release from CD8+ T-cells electroporated with alpha and beta chain RNA of TCR R39P1F5 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 23:
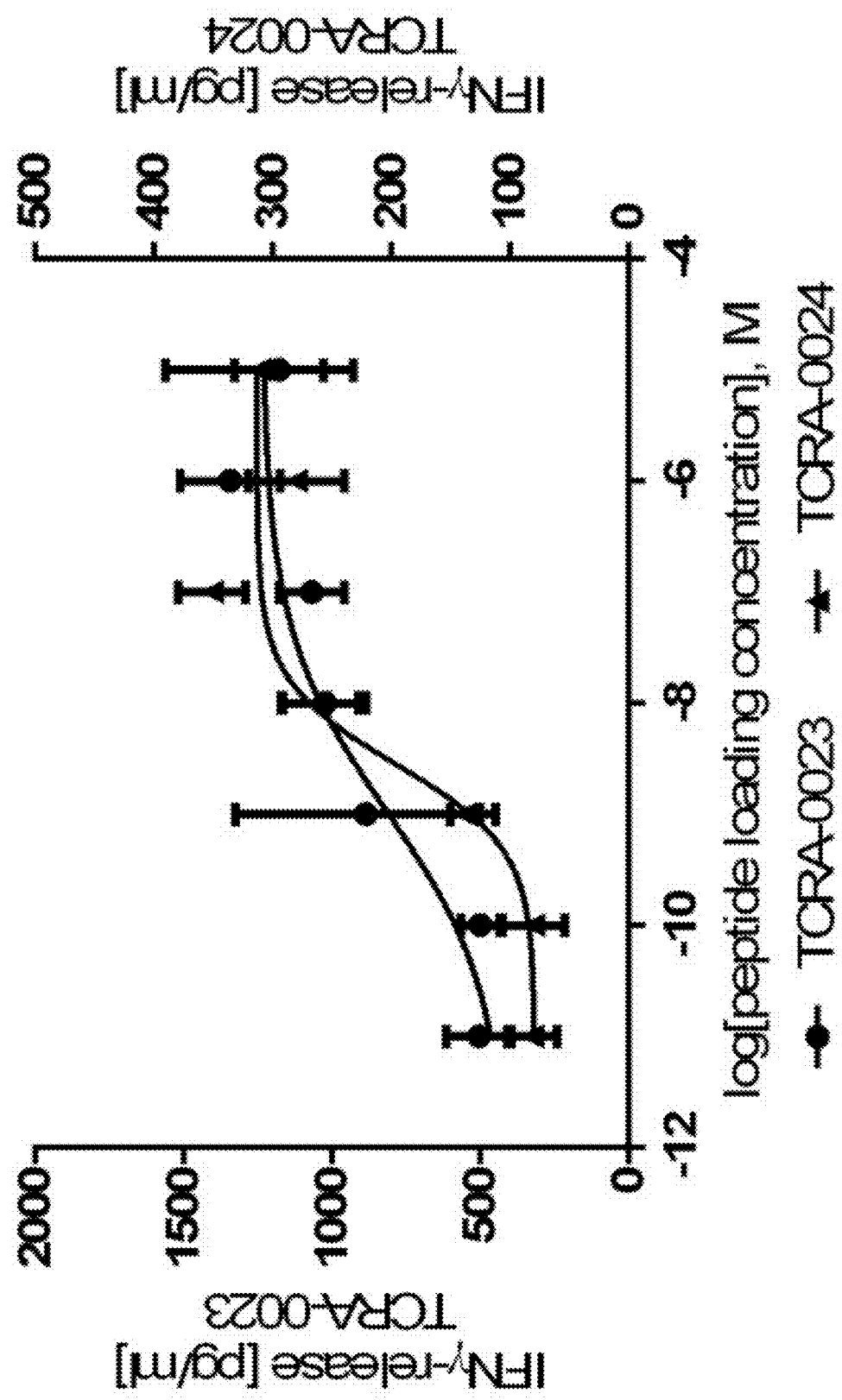

FIG. 23: IFNγ release from CD8+ T-cells electroporated with alpha and beta chain RNA of TCR R40P1C2 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 24:
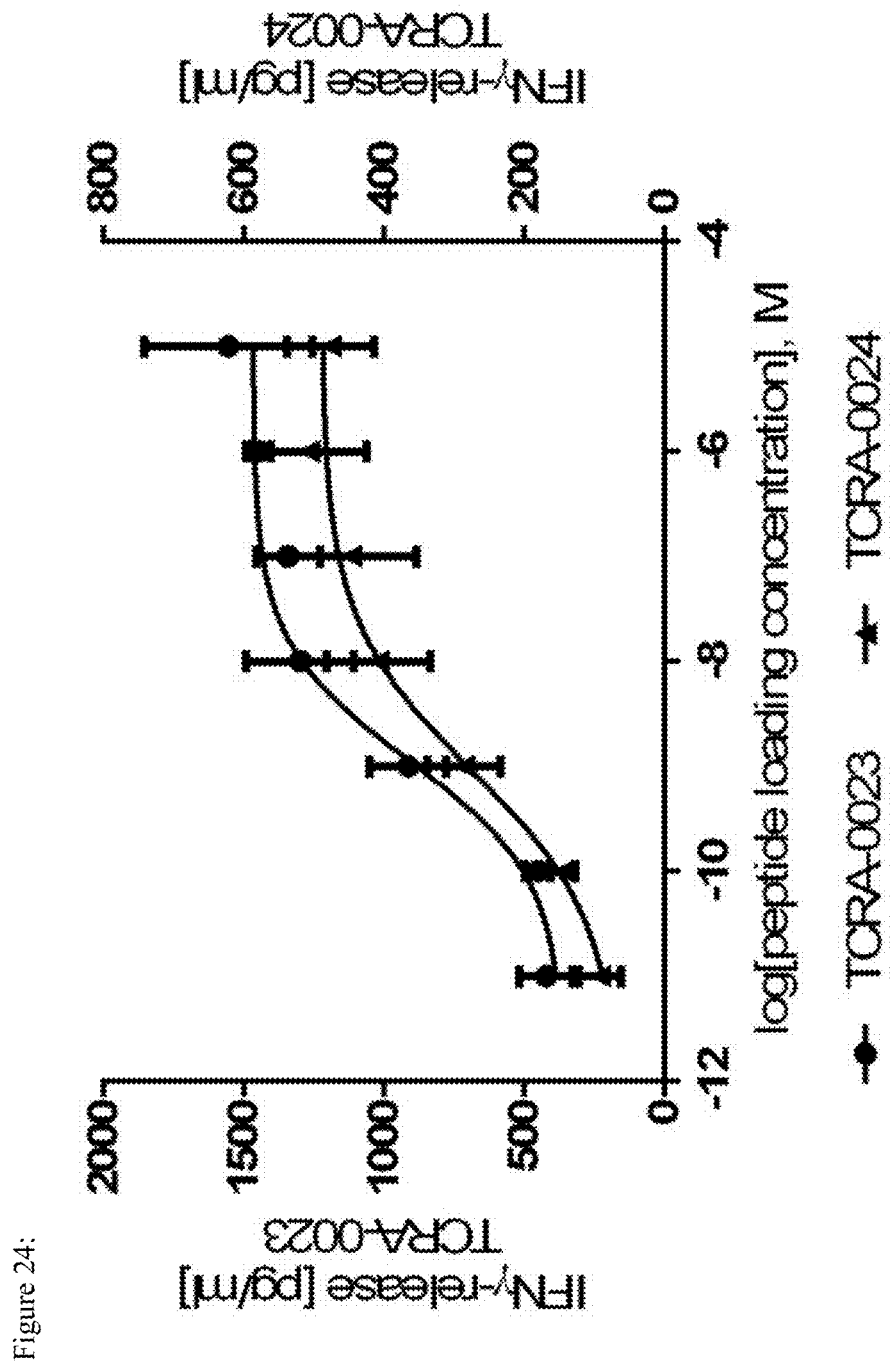

FIG. 24: IFNγ release from CD8+ T-cells electroporated with alpha and beta chain RNA of TCR R41P3E6 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 25:
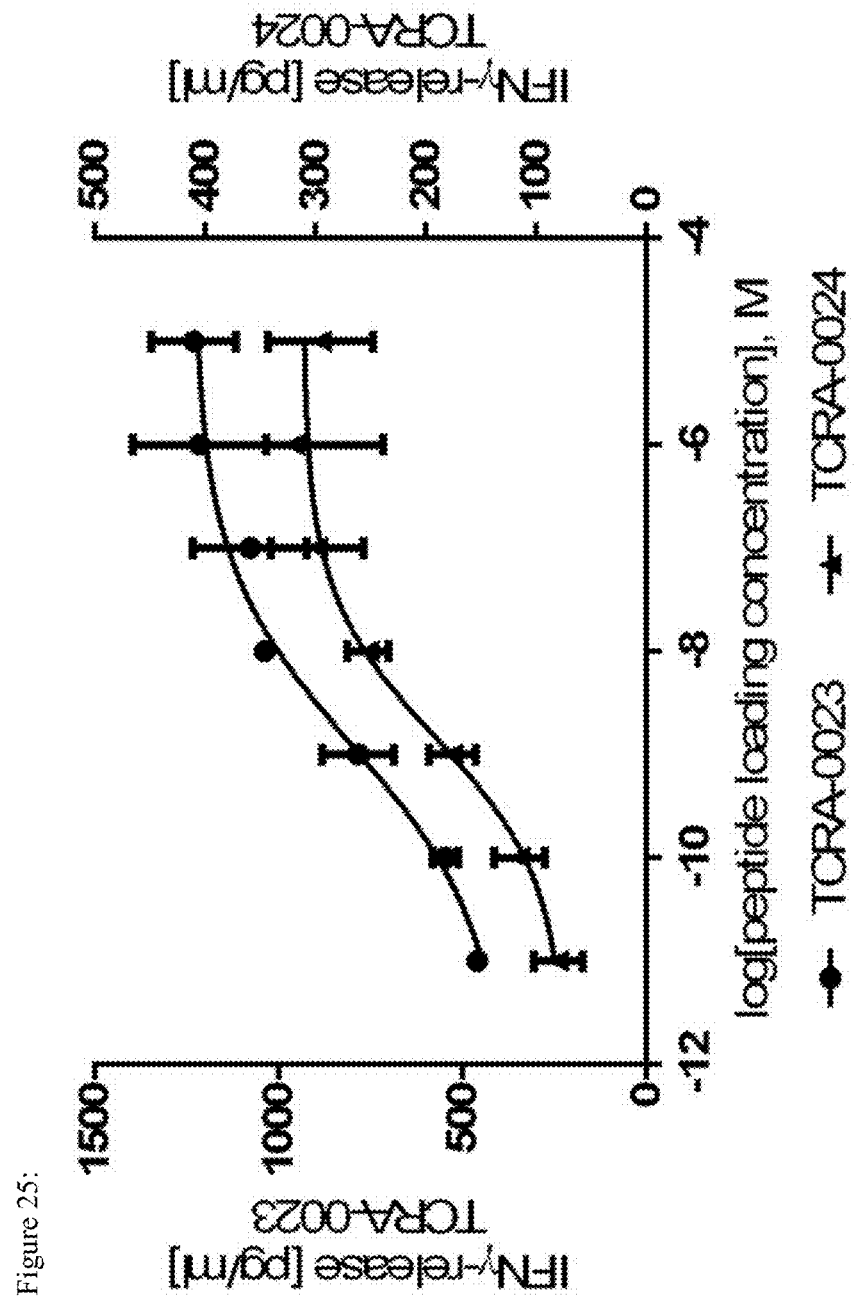

FIG. 25: IFNγ release from CD8+ T-cells electroporated with alpha and beta chain RNA of TCR R43P3G4 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 26:
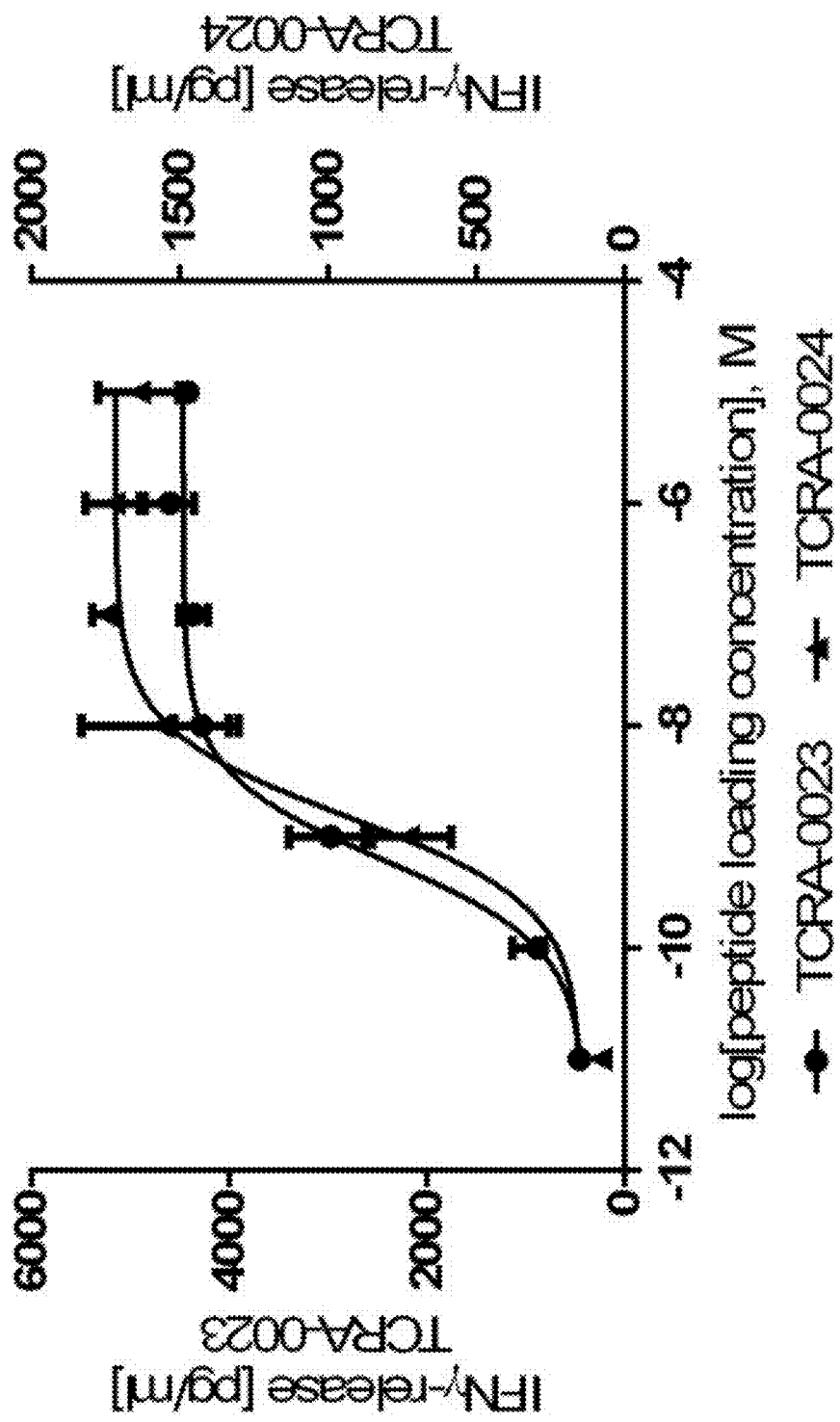

FIG. 26: IFNγ release from CD8+ T-cells electroporated with alpha and beta chain RNA of TCR R44P3B3 (Table FIG. 27: IFNγ release from CD8+ T-cells electroporated with alpha and beta chain RNA of TCR R44P3E7 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 28:
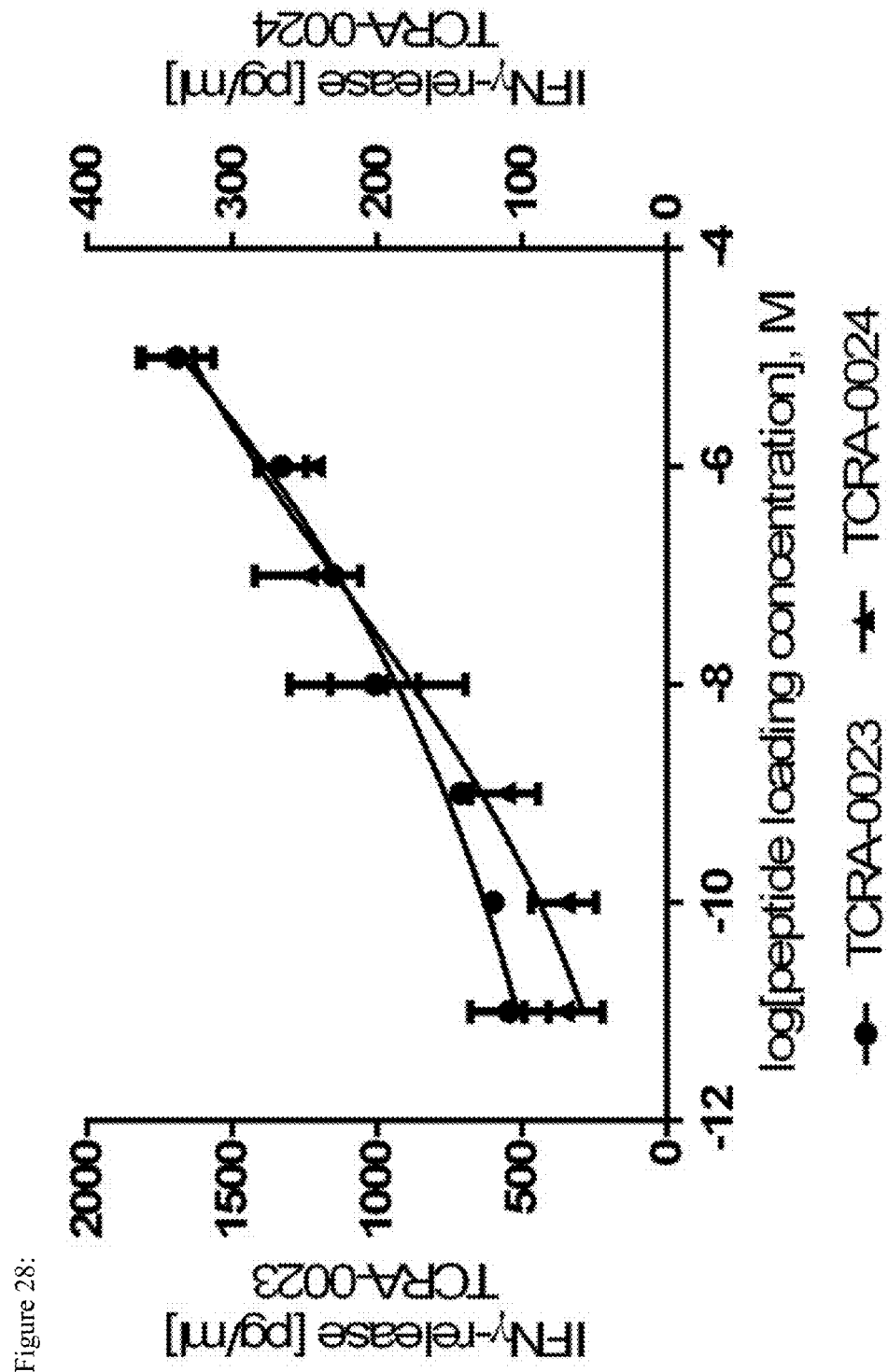

FIG. 28: IFNγ release from CD8+ T-cells electroporated with alpha and beta chain RNA of TCR R49P2B7 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 29:
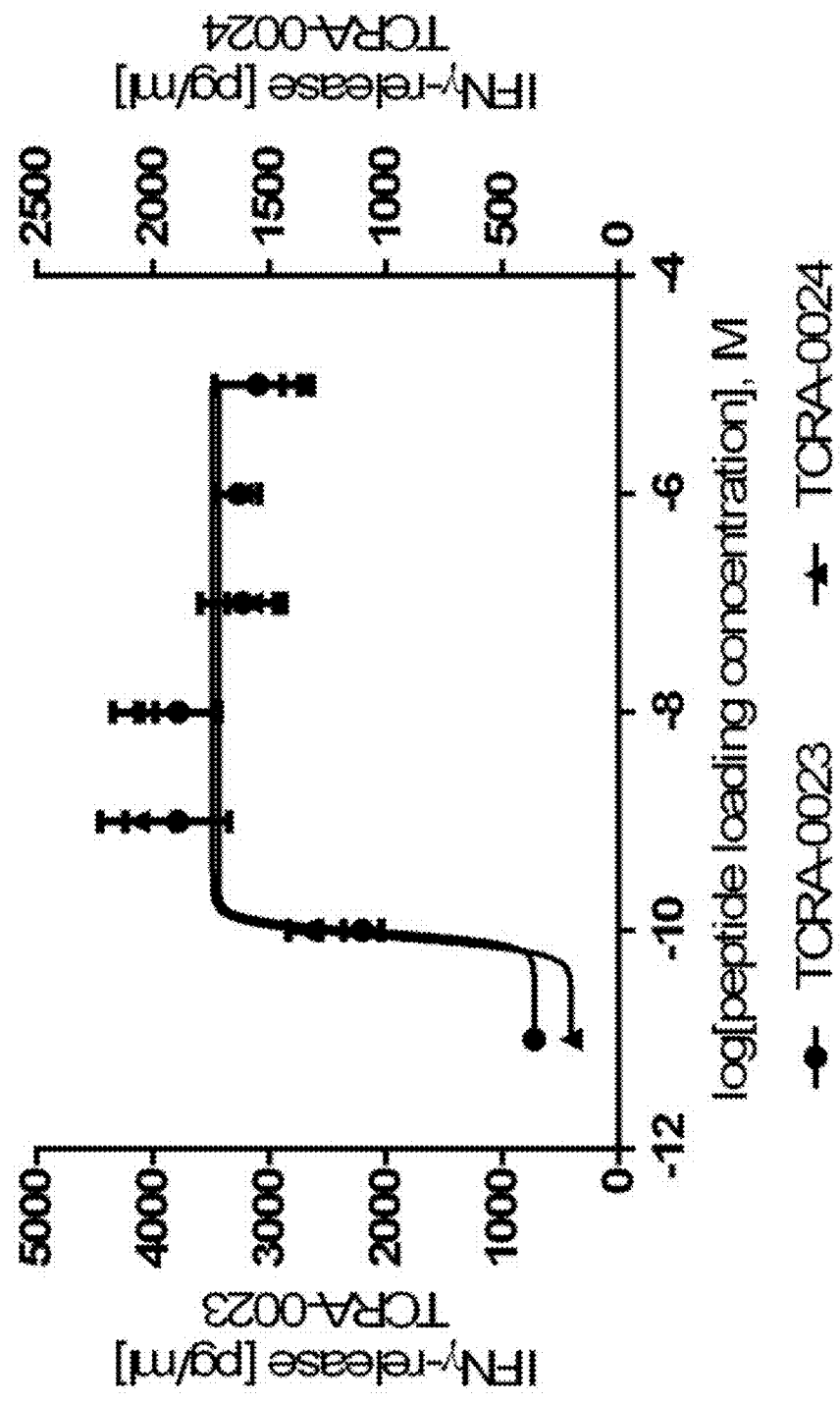

FIG. 29: IFNγ release from CD8+ T-cells electroporated with alpha and beta chain RNA of TCR R55P1G7 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 30:
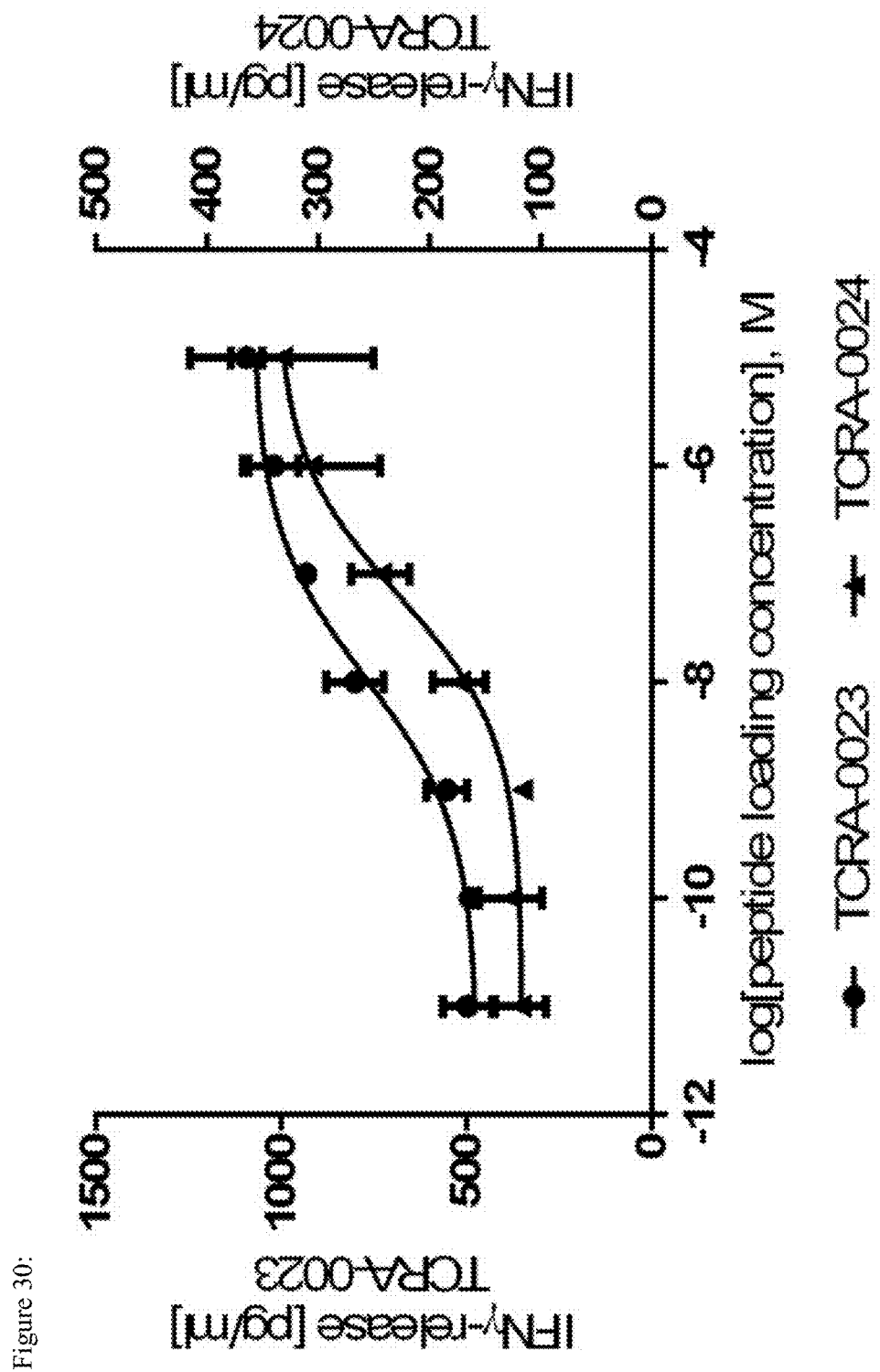

FIG. 30: IFNγ release from CD8+ T-cells electroporated with alpha and beta chain RNA of TCR R59P2A7 (Table 1) after co-incubation with T2 target cells loaded with SPINK2-001 peptide (SEQ ID NO:133) in various peptide loading concentrations from 10 μM to 10 pM. IFNγ release data were obtained with CD8+ T-cells derived from two different healthy donors.

Figure 31:
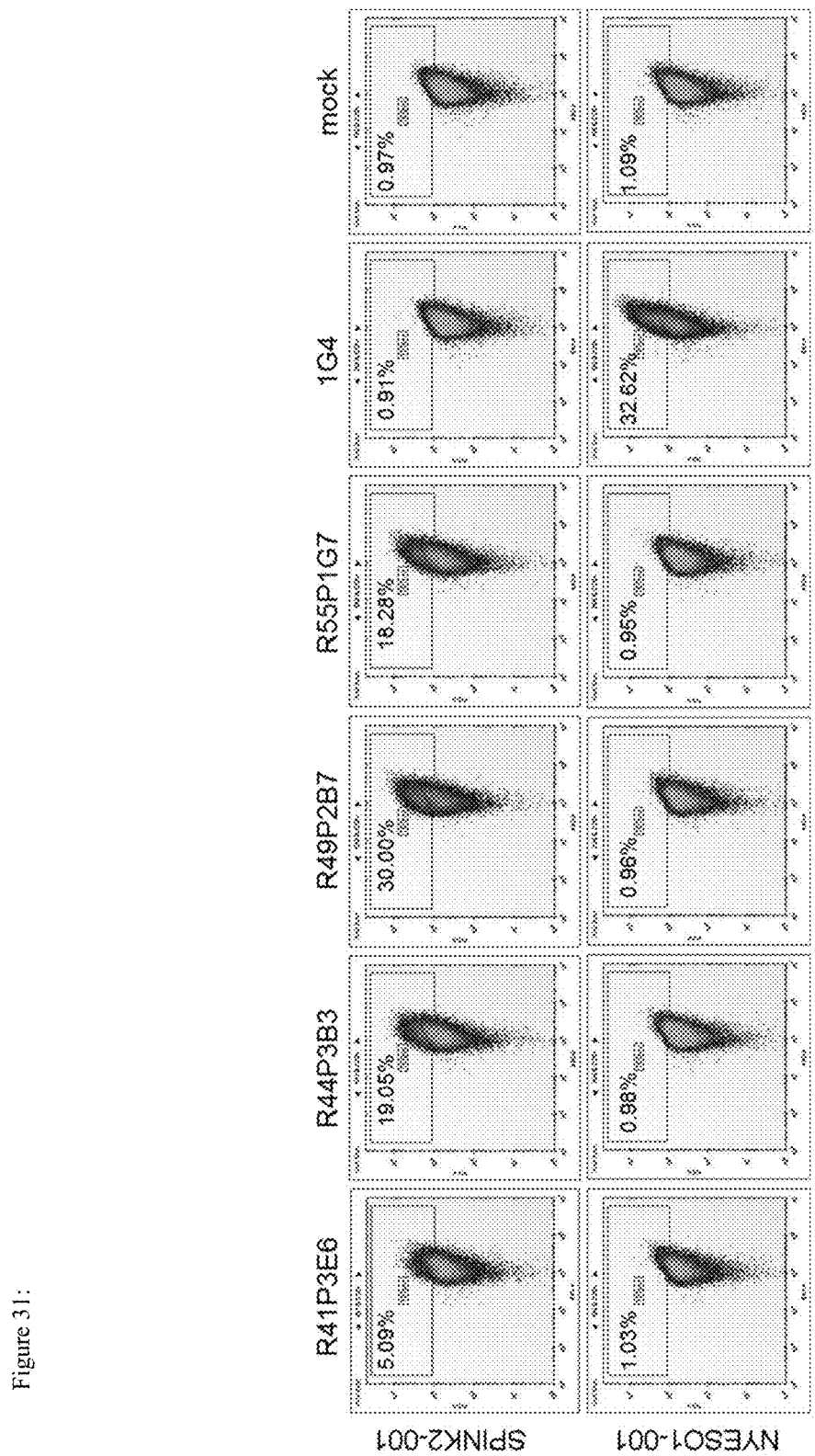

FIG. 31: HLA-A*02/SPINK2-001 tetramer or HLA-A*02/NYESO1-001 tetramer staining, respectively, of CD8+ T-cells electroporated with alpha and beta chain RNA of TCRs R41P3E6, R44P3B3, R49P2B7 and R55P1G7, respectively. CD8+ T-cells electroporated with RNA of 1G4 TCR (SEQ ID: 121-132) that specifically binds to HLA-A*02/NYESO1-001 complex and mock electroporated CD8+ T-cells served as controls.

Figure 32:
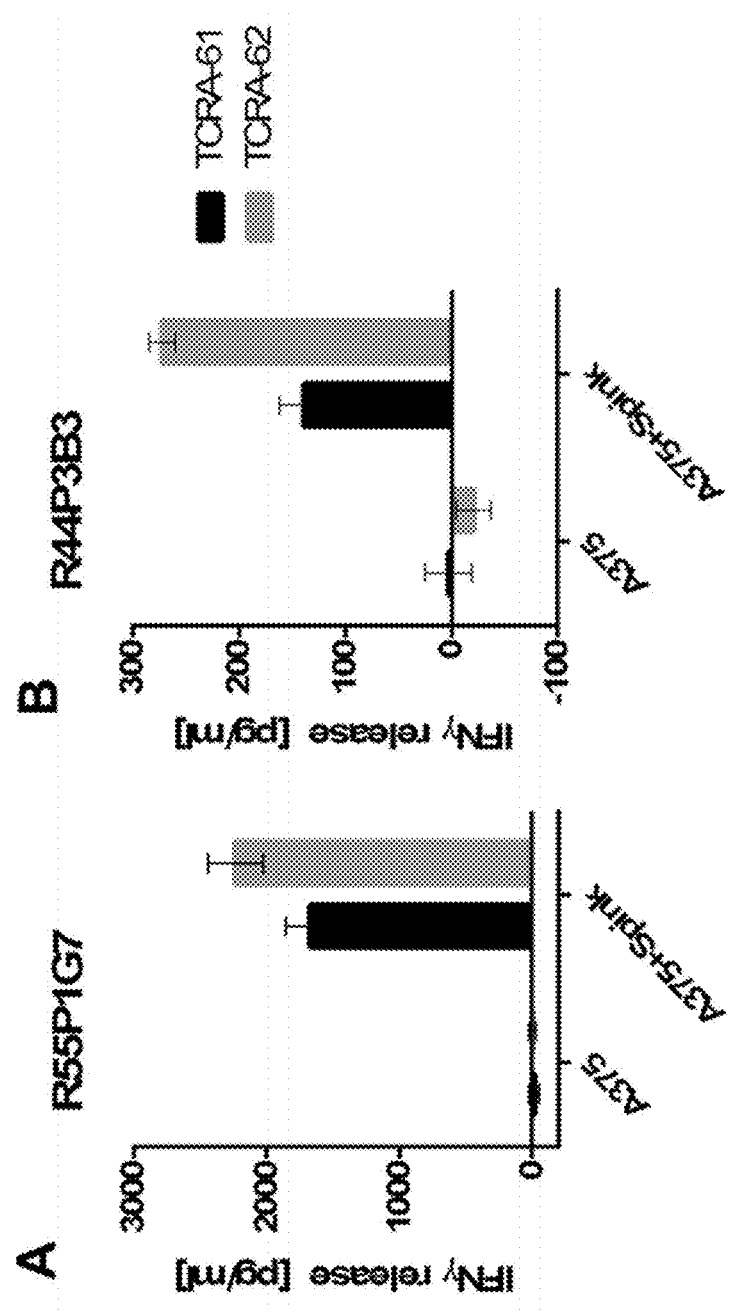

FIG. 32: IFNγ release from CD8+ T-cells electroporated with alpha and beta chain RNA of TCR R55P1G7 (A) or R44P3B3 (B) (Table 1) after co-incubation with A375 target cells overexpressing SPINK2 or wildtype A375 cells. IFNγ release data were obtained with CD8+ T-cells derived from two different healthy donors (TCRA-61 and TCRA-62). Background subtracted data is shown (i.e. pre-activation from effector only controls and signal of non-transduced effector co-cultured with target cell line was subtracted from samples of interest).

Figure 33:
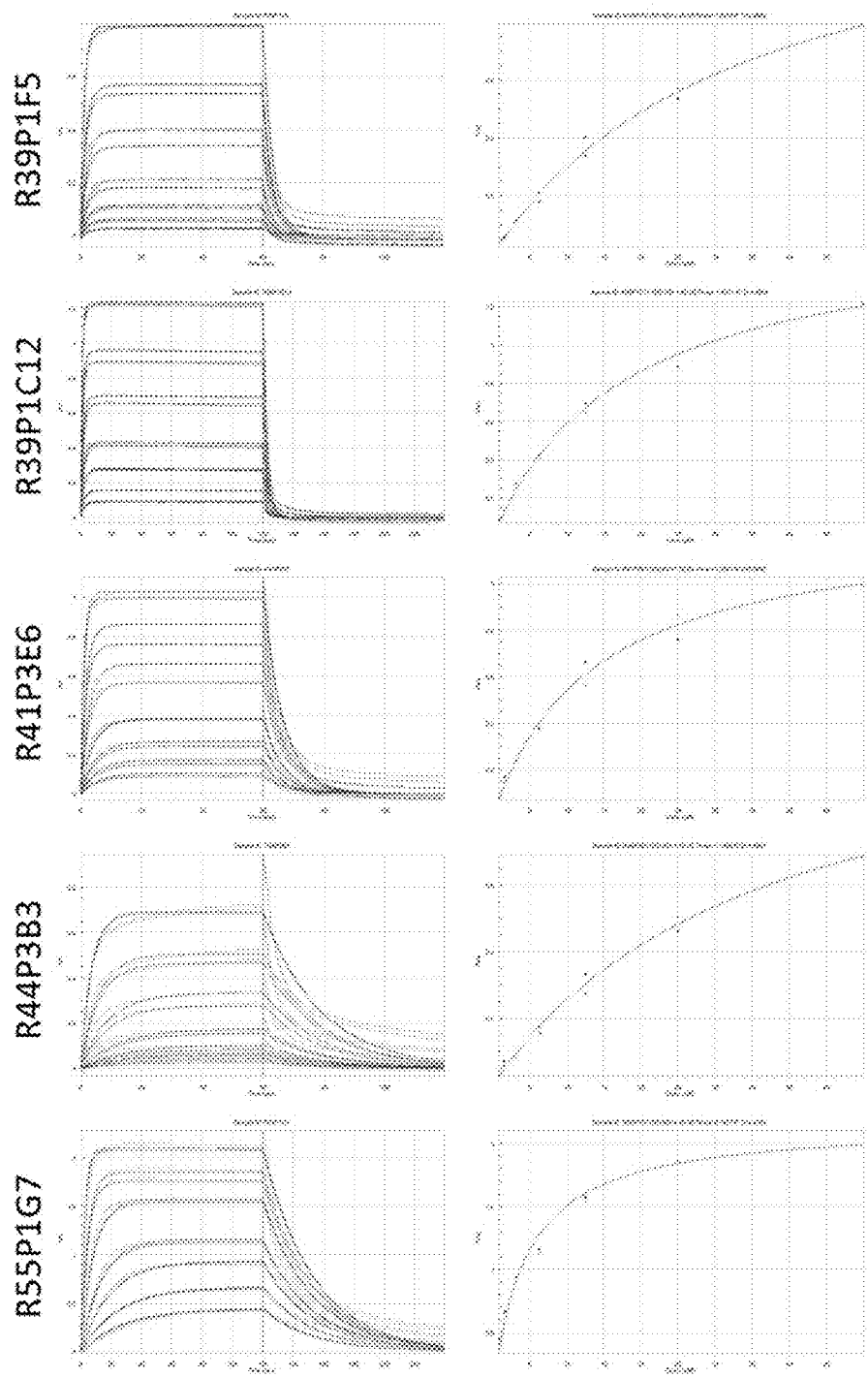

FIG. 33: Biolayer interferometry binding analysis of HLA-A*02:01:SPINK2-001 (immobilized on sensor) and soluble TCR variants of TCRs R39P1F5, R39P1C12, R41P3E6, R44P3B3 and R55P1G7. Left panel shows the signal (y-axis) of binding curves and fits for different TCR concentrations over time (x-axis), right panel shows the response at the equilibrium (y-axis) over different TCR concentrations (x-axis) and fits, respectively.

TABLE 1

TCR sequences of the invention

| SEQ ID NO: | TCR | Chain | Region | Sequence |
|---|---|---|---|---|
| 1 | R39P1C12 | alpha | CDR1 | DSSSTY |
| 2 | R39P1C12 | alpha | CDR2 | IFS |
| 3 | R39P1C12 | alpha | CDR3 | CAEIDNQGGKLIF |
| 4 | R39P1C12 | alpha | variable domain | MKTFAGFSFLFLWLQLDCMSRGED VEQSLFLSVREGDSSVINCTYTDSSS TYLYWYKQEPGAGLQLLTYIFSNMD MKQDQRLTVLLNKKDKHLSLRIADT QTGDSAIYFCAEIDNQGGKLIFGQGT ELSVKP |
| 5 | R39P1C12 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 6 | R39P1C12 | alpha | full-length | MKTFAGFSFLFLWLQLDCMSRGED VEQSLFLSVREGDSSVINCTYTDSSS TYLYWYKQEPGAGLQLLTYIFSNMD MKQDQRLTVLLNKKDKHLSLRIADT QTGDSAIYFCAEIDNQGGKLIFGQGT ELSVKPNIQNPDPAVYQLRDSKSSD KSVCLFTDFDSQTNVSQSKDSDVYIT DKTVLDMRSMDFKSNSAVAWSNKS DFACANAFNNSIIPEDTFFPSPESSCD VKLVEKSFETDTNLNFQNLSVIGFRI LLLKVAGFNLLMTLRLWSS |
| 7 | R39P1C12 | beta | CDR1 | SGHDT |
| 8 | R39P1C12 | beta | CDR2 | YYEEEE |

TABLE 1-continued

TCR sequences of the invention

| SEQ ID NO: | TCR | Chain | Region | Sequence |
|---|---|---|---|---|
| 9 | R39P1C12 | beta | CDR3 | CASSQLNTEAFF |
| 10 | R39P1C12 | beta | variable domain | MGPGLLCWALLCLLGAGLVDAGVT QSPTHLIKTRGQQVTLRCSPKSGHDT VSWYQQALGQGPQFIFQYYEEEERQ RGNFPDRFSGHQFPNYSSELNVNAL LLGDSALYLCASSQLNTEAFFGQGT RLTVV |
| 11 | R39P1C12 | beta | constant domain | EDLNKVFPPEVAVFEPSEAEISHTQK ATLVCLATGFFPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSVSYQQGVLSATILYE ILLGKATLYAVLVSALVLMAMVKR KDF |
| 12 | R39P1C12 | beta | full-length | MGPGLLCWALLCLLGAGLVDAGVT QSPTHLIKTRGQQVTLRCSPKSGHDT VSWYQQALGQGPQFIFQYYEEEERQ RGNFPDRFSGHQFPNYSSELNVNAL LLGDSALYLCASSQLNTEAFFGQGT RLTVVEDLNKVFPPEVAVFEPSEAEI SHTQKATLVCLATGFFPDHVELSW WVNGKEVHSGVSTDPQPLKEQPAL NDSRYCLSSRLRVSATFWQNPRNHF RCQVQFYGLSENDEWTQDRAKPVT QIVSAEAWGRADCGFTSVSYQQGVL SATILYEILLGKATLYAVLVSALVLM AMVKRKDF |
| 13 | R39P1F5 | alpha | CDR1 | DRGSQS |
| 14 | R39P1F5 | alpha | CDR2 | IY |
| 15 | R39P1F5 | alpha | CDR3 | CAVNNARLMF |
| 16 | R39P1F5 | alpha | variable domain | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAVNNARLMFGDGTQL VVKP |
| 17 | R39P1F5 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 18 | R39P1F5 | alpha | full-length | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAVNNARLMFGDGTQL VVKPNIQNPDPAVYQLRDSKSSDKS VCLFTDFDSQTNVSQSKDSDVYITD KTVLDMRSMDFKSNSAVAWSNKSD FACANAFNNSIIPEDTFFPSPESSCDV KLVEKSFETDTNLNFQNLSVIGFRIL LLKVAGFNLLMTLRLWSS |
| 19 | R39P1F5 | beta | CDR1 | SNHLY |
| 20 | R39P1F5 | beta | CDR2 | FYNNEI |
| 21 | R39P1F5 | beta | CDR3 | CASSGQGANEQYF |
| 22 | R39P1F5 | beta | variable domain | MDTWLVCWAIFSLLKAGLTEPEVTQ TPSHQVTQMGQEVILRCVPISNHLYF YWYRQILGQKVEFLVSFYNNEISEKS EIFDDQFSVERPDGSNFTLKIRSTKLE |

TABLE 1-continued

TCR sequences of the invention

| SEQ ID NO: | TCR | Chain | Region | Sequence |
|---|---|---|---|---|
|  |  |  |  | DSAMYFCASSGQGANEQYFGPGTRLTVT |
| 23 | R39P1F5 | beta | constant domain | EDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 24 | R39P1F5 | beta | full-length | MDTWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTKLEDSAMYFCASSGQGANEQYFGPGTRLTVTEDLKNVFPPEVAVFEPSEAEISHTQKATLVCLATGFYPDHVELSWWVNGKEVHSGVSTDPQPLKEQPALNDSRYCLSSRLRVSATFWQNPRNHFRCQVQFYGLSENDEWTQDRAKPVTQIVSAEAWGRADCGFTSESYQQGVLSATILYEILLGKATLYAVLVSALVLMAMVKRKDSRG |
| 25 | R40P1C2 | alpha | CDR1 | TSESDYY |
| 26 | R40P1C2 | alpha | CDR2 | QEAY |
| 27 | R40P1C2 | alpha | CDR3 | CAYLNYQLIW |
| 28 | R40P1C2 | alpha | variable domain | MACPGFLWALVISTCLEFSMAQTVTQSQPEMSVQEAETVTLSCTYDTSESDYYLFWYKQPPSRQMILVIRQEAYKQQNATENRFSVNFQKAAKSFSLKISDSQLGDAAMYFCAYLNYQLIWGAGTKLIIKP |
| 29 | R40P1C2 | alpha | constant domain | DIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 30 | R40P1C2 | alpha | full-length | MACPGFLWALVISTCLEFSMAQTVTQSQPEMSVQEAETVTLSCTYDTSESDYYLFWYKQPPSRQMILVIRQEAYKQQNATENRFSVNFQKAAKSFSLKISDSQLGDAAMYFCAYLNYQLIWGAGTKLIIKPDIQNPDDAVYQLRDSKSSDKSVCLFTDFDSQTNVSQSKDSDVYITDKTVLDMRSMDFKSNSAVAWSNKSDFACANAFNNSIIPEDTFFPSPESSCDVKLVEKSFETDTNLNFQNLSVIGFRILLLKVAGFNLLMTLRLWSS |
| 31 | R40P1C2 | beta | CDR1 | SNHLY |
| 32 | R40P1C2 | beta | CDR2 | FYNNEI |
| 33 | R40P1C2 | beta | CDR3 | CASSEMTAVGQYF |
| 34 | R40P1C2 | beta | variable domain | MDTWLVCWAIFSLLKAGLTEPEVTQTPSHQVTQMGQEVILRCVPISNHLYFYWYRQILGQKVEFLVSFYNNEISEKSEIFDDQFSVERPDGSNFTLKIRSTKLEDSAMYFCASSEMTAVGQYFGPGTRLTVT |
| 35 | R40P1C2 | beta | constant domain | EDLKNVFPPEVAVFEPSEAEISHTQKATLVCLATGFYPDHVELSWWVNGKEVHSGVSTDPQPLKEQPALNDSRYC |

TABLE 1-continued

TCR sequences of the invention

| SEQ ID NO: | TCR | Chain | Region | Sequence |
|---|---|---|---|---|
|  |  |  |  | LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 36 | R40P1C2 | beta | full-length | MDTWLVCWAIFSLLKAGLTEPEVTQ TPSHQVTQMGQEVILRCVPISNHLYF YWYRQILGQKVEFLVSFYNNEISEKS EIFDDQFSVERPDGSNFTLKIRSTKLE DSAMYFCASSEMTAVGQYFGPGTR LTVTEDLKNVFPPEVAVFEPSEAEIS HTQKATLVCLATGFYPDHVELSWW VNGKEVHSGVSTDPQPLKEQPALND SRYCLSSRLRVSATFWQNPRNHFRC QVQFYGLSENDEWTQDRAKPVTQIV SAEAWGRADCGFTSESYQQGVLSAT ILYEILLGKATLYAVLVSALVLMAM VKRKDSRG |
| 37 | R41P3E6 | alpha | CDR1 | DRGSQS |
| 38 | R41P3E6 | alpha | CDR2 | IY |
| 39 | R41P3E6 | alpha | CDR3 | CAAFSGYALNF |
| 40 | R41P3E6 | alpha | variable domain | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAAFSGYALNFGKGTSL LVTP |
| 41 | R41P3E6 | alpha | constant domain | HIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 42 | R41P3E6 | alpha | full-length | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAAFSGYALNFGKGTSL LVTPHIQNPDPAVYQLRDSKSSDKS VCLFTDFDSQTNVSQSKDSDVYITD KTVLDMRSMDFKSNSAVAWSNKSD FACANAFNNSIIPEDTFFPSPESSCDV KLVEKSFETDTNLNFQNLSVIGFRIL LLKVAGFNLLMTLRLWSS |
| 43 | R41P3E6 | beta | CDR1 | SNHLY |
| 44 | R41P3E6 | beta | CDR2 | FYNNEI |
| 45 | R41P3E6 | beta | CDR3 | CASSQYTGELFF |
| 46 | R41P3E6 | beta | variable domain | MDTWLVCWAIFSLLKAGLTEPEVTQ TPSHQVTQMGQEVILRCVPISNHLYF YWYRQILGQKVEFLVSFYNNEISEKS EIFDDQFSVERPDGSNFTLKIRSTKLE DSAMYFCASSQYTGELFFGEGSRLT VL |
| 47 | R41P3E6 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |

TABLE 1-continued

TCR sequences of the invention

| SEQ ID NO: | TCR | Chain | Region | Sequence |
|---|---|---|---|---|
| 48 | R41P3E6 | beta | full-length | MDTWLVCWAIFSLLKAGLTEPEVTQ TPSHQVTQMGQEVILRCVPISNHLYF YWYRQILGQKVEFLVSFYNNEISEKS EIFDDQFSVERPDGSNFTLKIRSTKLE DSAMYFCASSQYTGELFFGEGSRLT VLEDLKNVFPPEVAVFEPSEAEISHT QKATLVCLATGFYPDHVELSWWVN GKEVHSGVSTDPQPLKEQPALNDSR YCLSSRLRVSATFWQNPRNHFRCQV QFYGLSENDEWTQDRAKPVTQIVSA EAWGRADCGFTSESYQQGVLSATIL YEILLGKATLYAVLVSALVLMAMV KRKDSRG |
| 49 | R43P3G4 | alpha | CDR1 | DRGSQS |
| 50 | R43P3G4 | alpha | CDR2 | IY |
| 51 | R43P3G4 | alpha | CDR3 | CAVNGGDMRF |
| 52 | R43P3G4 | alpha | variable domain | MKSLRVLLVILWLQLSWVWSQQKE VEQNSGPLSVPEGAIASLNCTYSDRG SQSFFWYRQYSGKSPELIMFIYSNGD KEDGRFTAQLNKASQYVSLLIRDSQ PSDSATYLCAVNGGDMRFGAGTRL TVKP |
| 53 | R43P3G4 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 54 | R43P3 G4 | alpha | full-length | MKSLRVLLVILWLQLSWVWSQQKE VEQNSGPLSVPEGAIASLNCTYSDRG QSSFFWYRQYSGKSPELIMFIYSNGD KEDGRFTAQLNKASQYVSLLIRDSQ PSDSATYLCAVNGGDMRFGAGTRL TVKPNIQNPDPAVYQLRDSKSSDKS VCLFTDFDSQTNVSQSKDSDVYITD KTVLDMRSMDFKSNSAVAWSNKSD FACANAFNNSIIPEDTFFPSPESSCDV KLVEKSFETDTNLNFQNLSVIGFRIL LLKVAGFNLLMTLRLWSS |
| 55 | R43P3G4 | beta | CDR1 | SNHLY |
| 56 | R43P3G4 | beta | CDR2 | FYNNEI |
| 57 | R43P3G4 | beta | CDR3 | CASSGQGALEQYF |
| 58 | R43P3G4 | beta | variable domain | MDTWLVCWAIFSLLKAGLTEPEVTQ TPSHQVTQMGQEVILRCVPISNHLYF YWYRQILGQKVEFLVSFYNNEISEKS EIFDDQFSVERPDGSNFTLKIRSTKLE DSAMYFCASSGQGALEQYFGPGTRL TVT |
| 59 | R43P3G4 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 60 | R43P3G4 | beta | full-length | MDTWLVCWAIFSLLKAGLTEPEVTQ TPSHQVTQMGQEVILRCVPISNHLYF YWYRQILGQKVEFLVSFYNNEISEKS EIFDDQFSVERPDGSNFTLKIRSTKLE DSAMYFCASSGQGALEQYFGPGTRL TVTEDLKNVFPPEVAVFEPSEAEISH |

TABLE 1-continued

TCR sequences of the invention

| SEQ ID NO: | TCR | Chain | Region | Sequence |
|---|---|---|---|---|
| | | | | TQKATLVCLATGFYPDHVELSWWV NGKEVHSGVSTDPQPLKEQPALNDS RYCLSSRLRVSATFWQNPRNHFRCQ VQFYGLSENDEWTQDRAKPVTQIVS AEAWGRADCGFTSESYQQGVLSATI LYEILLGKATLYAVLVSALVLMAM VKRKDSRG |
| 61 | R44P3B3 | alpha | CDR1 | NSMFDY |
| 62 | R44P3B3 | alpha | CDR2 | ISS |
| 63 | R44P3B3 | alpha | CDR3 | CAASGLYNQGGKLIF |
| 64 | R44P3B3 | alpha | variable domain | MAMLLGASVLILWLQPDWVNSQQK NDDQQVKQNSPSLSVQEGRISILNCD YTNSMFDYFLWYKKYPAEGPTFLISI SSIKDKNEDGRFTVFLNKSAKHLSLH IVPSQPGDSAVYFCAASGLYNQGGK LIFGQGTELSVKP |
| 65 | R44P3B3 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 66 | R44P3B3 | alpha | full-length | MAMLLGASVLILWLQPDWVNSQQK NDDQQVKQNSPSLSVQEGRISILNCD YTNSMFDYFLWYKKYPAEGPTFLISI SSIKDKNEDGRFTVFLNKSAKHLSLH IVPSQPGDSAVYFCAASGLYNQGGK LIFGQGTELSVKPNIQNPDPAVYQLR DSKSSDKSVCLFTDFDSQTNVSQSK DSDVYITDKTVLDMRSMDFKSNSAV AWSNKSDFACANAFNNSIIPEDTFFP SPESSCDVKLVEKSFETDTNLNFQNL SVIGFRILLLKVAGFNLLMTLRLWSS |
| 67 | R44P3B3 | beta | CDR1 | LGHDT |
| 68 | R44P3B3 | beta | CDR2 | YNNKEL |
| 69 | R44P3B3 | beta | CDR3 | CASSLGDRGYEQYF |
| 70 | R44P3B3 | beta | variable domain | MGCRLLCCVVFCLLQAGPLDTAVSQ TPKYLVTQMGNDKSIKCEQNLGHDT MYWYKQDSKKFLKIMFSYNNKELII NETVPNRFSPKSPDKAHLNLHINSLE LGDSAVYFCASSLGDRGYEQYFGPG TRLTVT |
| 71 | R44P3B3 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 72 | R44P3B3 | beta | full-length | MGCRLLCCVVFCLLQAGPLDTAVSQ TPKYLVTQMGNDKSIKCEQNLGHDT MYWYKQDSKKFLKIMFSYNNKELII NETVPNRFSPKSPDKAHLNLHINSLE LGDSAVYFCASSLGDRGYEQYFGPG TRLTVTEDLKNVFPPEVAVFEPSEAE ISHTQKATLVCLATGFYPDHVELSW WVNGKEVHSGVSTDPQPLKEQPAL NDSRYCLSSRLRVSATFWQNPRNHF RCQVQFYGLSENDEWTQDRAKPVT |

TABLE 1-continued

TCR sequences of the invention

| SEQ ID NO: | TCR | Chain | Region | Sequence |
|---|---|---|---|---|
| | | | | QIVSAEAWGRADCGFTSESYQQGVL SATILYEILLGKATLYAVLVSALVLM AMVKRKDSRG |
| 73 | R44P3E7 | alpha | CDR1 | DSSSTY |
| 74 | R44P3E7 | alpha | CDR2 | IFS |
| 75 | R44P3E7 | alpha | CDR3 | CAEINNNARLMF |
| 76 | R44P3E7 | alpha | variable domain | MKTFAGFSFLFLWLQLDCMSRGED VEQSLFLSVREGDSSVINCTYTDSSS TYLYWYKQEPGAGLQLLTYIFSNMD MKQDQRLTVLLNKKDKHLSLRIADT QTGDSAIYFCAEINNNARLMFGDGT QLVVKP |
| 77 | R44P3E7 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 78 | R44P3E7 | alpha | full-length | MKTFAGFSFLFLWLQLDCMSRGED VEQSLFLSVREGDSSVINCTYTDSSS TYLYWYKQEPGAGLQLLTYIFSNMD MKQDQRLTVLLNKKDKHLSLRIADT QTGDSAIYFCAEINNNARLMFGDGT QLVVKPNIQNPDPAVYQLRDSKSSD KSVCLFTDFDSQTNVSQSKDSDVYIT DKTVLDMRSMDFKSNSAVAWSNKS DFACANAFNNSIIPEDTFFPSPESSCD VKLVEKSFETDTNLNFQNLSVIGFRI LLLKVAGFNLLMTLRLWSS |
| 79 | R44P3E7 | beta | CDR1 | PRHDT |
| 80 | R44P3E7 | beta | CDR2 | FYEKMQ |
| 81 | R44P3E7 | beta | CDR3 | CASSPPDQNTQYF |
| 82 | R44P3E7 | beta | variable domain | MLSPDLPDSAWNTRLLCHVMLCLL GAVSVAAGVIQSPRHLIKEKRETATL KCYPIPRHDTVYWYQQGPGQDPQFL ISFYEKMQSDKGSIPDRFSAQQFSDY HSELNMSSLELGDSALYFCASSPPDQ NTQYFGPGTRLTVL |
| 83 | R44P3E7 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 84 | R44P3E7 | beta | full-length | MLSPDLPDSAWNTRLLCHVMLCLL GAVSVAAGVIQSPRHLIKEKRETATL KCYPIPRHDTVYWYQQGPGQDPQFL ISFYEKMQSDKGSIPDRFSAQQFSDY HSELNMSSLELGDSALYFCASSPPDQ NTQYFGPGTRLTVLEDLKNVFPPEV AVFEPSEAEISHTQKATLVCLATGFY PDHVELSWWVNGKEVHSGVSTDPQ PLKEQPALNDSRYCLSSRLRVSATF WQNPRNHFRCQVQFYGLSENDEWT QDRAKPVTQIVSAEAWGRADCGFTS ESYQQGVLSATILYEILLGKATLYAV LVSALVLMAMVKRKDSRG |
| 85 | R49P2B7 | alpha | CDR1 | SSVPPY |

TABLE 1-continued

TCR sequences of the invention

| SEQ ID NO: | TCR | Chain | Region | Sequence |
|---|---|---|---|---|
| 86 | R49P2B7 | alpha | CDR2 | YTTG |
| 87 | R49P2B7 | alpha | CDR3 | CAVRIFGNEKLTF |
| 88 | R49P2B7 | alpha | variable domain | MLLLLVPVLEVIFTLGGTRAQSVTQL GSHVSVSEGALVLLRCNYSSSVPPYL FWYVQYPNQGLQLLLKYTTGATLV KGINGFEAEFKKSETSFHLTKPSAHM SDAAEYFCAVRIFGNEKLTFGTGTRL TIIP |
| 89 | R49P2B7 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 90 | R49P2B7 | alpha | full-length | MLLLLVPVLEVIFTLGGTRAQSVTQL GSHVSVSEGALVLLRCNYSSSVPPYL FWYVQYPNQGLQLLLKYTTGATLV KGINGFEAEFKKSETSFHLTKPSAHM SDAAEYFCAVRIFGNEKLTFGTGTRL TIIPNIQNPDPAVYQLRDSKSSDKSV CLFTDFDSQTNVSQSKDSDVYITDKT VLDMRSMDFKSNSAVAWSNKSDFA CANAFNNSIIPEDTFFPSPESSCDVKL VEKSFETDTNLNFQNLSVIGFRILLL KVAGFNLLMTLRLWSS |
| 91 | R49P2B7 | beta | CDR1 | MDHEN |
| 92 | R49P2B7 | beta | CDR2 | SYDVKM |
| 93 | R49P2B7 | beta | CDR3 | CASSLMGELTGELFF |
| 94 | R49P2B7 | beta | variable domain | MGIRLLCRVAFCFLAVGLVDVKVTQ SSRYLVKRTGEKVFLECVQDMDHE NMFWYRQDPGLGLRLIYFSYDVKM KEKGDIPEGYSVSREKKERFSLILES ASTNQTSMYLCASSLMGELTGELFF GEGSRLTVL |
| 95 | R49P2B7 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 96 | R49P2B7 | beta | full-length | MGIRLLCRVAFCFLAVGLVDVKVTQ SSRYLVKRTGEKVFLECVQDMDHE NMFWYRQDPGLGLRLIYFSYDVKM KEKGDIPEGYSVSREKKERFSLILES ASTNQTSMYLCASSLMGELTGELFF GEGSRLTVLEDLKNVFPPEVAVFEPS EAEISHTQKATLVCLATGFYPDHVE LSWWVNGKEVHSGVSTDPQPLKEQ PALNDSRYCLSSRLRVSATFWQNPR NHFRCQVQFYGLSENDEWTQDRAK PVTQIVSAEAWGRADCGFTSESYQQ GVLSATILYEILLGKATLYAVLVSAL VLMAMVKRKDSRG |
| 97 | R55P1G7 | alpha | CDR1 | NSAFQY |
| 98 | R55P1G7 | alpha | CDR2 | TY |
| 99 | R55P1G7 | alpha | CDR3 | CAMMGDTGTASKLTF |
| 100 | R55P1G7 | alpha | variable domain | MMKSLRVLLVILWLQLSWVWSQQK EVEQDPGPLSVPEGAIVSLNCTYSNS |

TABLE 1-continued

TCR sequences of the invention

| SEQ ID NO: | TCR | Chain | Region | Sequence |
|---|---|---|---|---|
| | | | | AFQYFMWYRQYSRKGPELLMYTYS SGNKEDGRFTAQVDKSSKYISLFIRD SQPSDSATYLCAMMGDTGTASKLTF GTGTRLQVTL |
| 101 | R55P1G7 | alpha | constant domain | DIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 102 | R55P1G7 | alpha | full-length | MMKSLRVLLVILWLQLSWVWSQQK EVEQDPGPLSVPEGAIVSLNCTYSNS AFQYFMWYRQYSRKGPELLMYTYS SGNKEDGRFTAQVDKSSKYISLFIRD SQPSDSATYLCAMMGDTGTASKLTF GTGTRLQVTLDIQNPDPAVYQLRDS KSSDKSVCLFTDFDSQTNVSQSKDS DVYITDKTVLDMRSMDFKSNSAVA WSNKSDFACANAFNNSIIPEDTFFPS PESSCDVKLVEKSFETDTNLNFQNLS VIGFRILLLKVAGFNLLMTLRLWSS |
| 103 | R55P1G7 | beta | CDR1 | MDHEN |
| 104 | R55P1G7 | beta | CDR2 | SYDVKM |
| 105 | R55P1G7 | beta | CDR3 | CASSFGGYEQYF |
| 106 | R55P1G7 | beta | variable domain | MGIRLLCRVAFCFLAVGLVDVKVTQ SSRYLVKRTGEKVFLECVQDMDHE NMFWYRQDPGLGLRLIYFSYDVKM KEKGDIPEGYSVSREKKERFSLILES ASTNQTSMYLCASSFGGYEQYFGPG TRLTVT |
| 107 | R55P1G7 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 108 | R55P1G7 | beta | full-length | MGIRLLCRVAFCFLAVGLVDVKVTQ SSRYLVKRTGEKVFLECVQDMDHE NMFWYRQDPGLGLRLIYFSYDVKM KEKGDIPEGYSVSREKKERFSLILES ASTNQTSMYLCASSFGGYEQYFGPG TRLTVTEDLKNVFPPEVAVFEPSEAE ISHTQKATLVCLATGFYPDHVELSW WVNGKEVHSGVSTDPQPLKEQPAL NDSRYCLSSRLRVSATFWQNPRNHF RCQVQFYGLSENDEWTQDRAKPVT QIVSAEAWGRADCGFTSESYQQGVL SATILYEILLGKATLYAVLVSALVLM AMVKRKDSRG |
| 109 | R59P2A7 | alpha | CDR1 | DRGSQS |
| 110 | R59P2A7 | alpha | CDR2 | IY |
| 111 | R59P2A7 | alpha | CDR3 | CAVQPHDMRF |
| 112 | R59P2A7 | alpha | variable domain | MKSLRVLLVILWLQLSWVWSQQKE VEQNSGPLSVPEGAIASLNCTYSDRG SQSFFWYRQYSGKSPELIMSIYSNGD KEDGRFTAQLNKASQYVSLLIRDSQ PSDSATYLCAVQPHDMRFGAGTRLT VKP |

TABLE 1-continued

TCR sequences of the invention

| SEQ ID NO: | TCR | Chain | Region | Sequence |
|---|---|---|---|---|
| 113 | R59P2A7 | alpha | constant domain | NIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |
| 114 | R59P2A7 | alpha | full-length | MKSLRVLLVILWLQLSWVWSQQKE VEQNSGPLSVPEGAIASLNCTYSDRG SQSFFWYRQYSGKSPELIMSIYSNGD KEDGRFTAQLNKASQYVSLLIRDSQ PSDSATYLCAVQPHDMRFGAGTRLT VKPNIQNPDPAVYQLRDSKSSDKSV CLFTDFDSQTNVSQSKDSDVYITDKT VLDMRSMDFKSNSAVAWSNKSDFA CANAFNNSIIPEDTFFPSPESSCDVKL VEKSFETDTNLNFQNLSVIGFRILLL KVAGFNLLMTLRLWSS |
| 115 | R59P2A7 | beta | CDR1 | GTSNPN |
| 116 | R59P2A7 | beta | CDR2 | SVGIG |
| 117 | R59P2A7 | beta | CDR3 | CAWSGLVAEQFF |
| 118 | R59P2A7 | beta | variable domain | MLCSLLALLLGTFFGVRSQTIHQWP ATLVQPVGSPLSLECTVEGTSNPNLY WYRQAAGRGLQLLFYSVGIGQISSE VPQNLSASRPDRQFILSSKKLLLSD SGFYLCAWSGLVAEQFFGPGTRLTV L |
| 119 | R59P2A7 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCQVQF YGLSENDEWTQDRAKPVTQIVSAEA WGRADCGFTSESYQQGVLSATILYEI LLGKATLYAVLVSALVLMAMVKRK DSRG |
| 120 | R59P2A7 | beta | full-length | MLCSLLALLLGTFFGVRSQTIHQWP ATLVQPVGSPLSLECTVEGTSNPNLY WYRQAAGRGLQLLFYSVGIGQISSE VPQNLSASRPDRQFILSSKKLLLSD SGFYLCAWSGLVAEQFFGPGTRLTV LEDLKNVFPPEVAVFEPSEAEISHTQ KATLVCLATGFYPDHVELSWWVNG KEVHSGVSTDPQPLKEQPALNDSRY CLSSRLRVSATFWQNPRNHFRCQVQ FYGLSENDEWTQDRAKPVTQIVSAE AWGRADCGFTSESYQQGVLSATILY EILLGKATLYAVLVSALVLMAMVK RKDSRG |
| 121 | 1G4 | alpha | CDR1 | DSAIYN |
| 122 | 1G4 | alpha | CDR2 | IQS |
| 123 | 1G4 | alpha | CDR3 | CAVRPTSGGSYIPTF |
| 124 | 1G4 | alpha | variable domain | METLLGLLILWLQLQWVSSKQEVTQ IPAALSVPEGENLVLNCSFTDSAIYN LQWFRQDPGKGLTSLLLIQSSQREQT SGRLNASLDKSSGRSTLYIAASQPGD SATYLCAVRPTSGGSYIPTFGRGTSLI VHP |
| 125 | 1G4 | alpha | constant domain | YIQNPDPAVYQLRDSKSSDKSVCLFT DFDSQTNVSQSKDSDVYITDKTVLD MRSMDFKSNSAVAWSNKSDFACAN AFNNSIIPEDTFFPSPESSCDVKLVEK SFETDTNLNFQNLSVIGFRILLLKVA GFNLLMTLRLWSS |

TABLE 1-continued

TCR sequences of the invention

| SEQ ID NO: | TCR | Chain | Region | Sequence |
|---|---|---|---|---|
| 126 | 1G4 | alpha | full-length | METLLGLLILWLQLQWVSSKQEVTQ IPAALSVPEGENLVLNCSFTDSAIYN LQWFRQDPGKGLTSLLLIQSSQREQT SGRLNASLDKSSGRSTLYIAASQPGD SATYLCAVRPTSGGSYIPTFGRGTSLI VHPYIQNPDPAVYQLRDSKSSDKSV CLFTDFDSQTNVSQSKDSDVYITDKT VLDMRSMDFKSNSAVAWSNKSDFA CANAFNNSIIPEDTFFPSPESSCDVKL VEKSFETDTNLNFQNLSVIGFRILLL KVAGFNLLMTLRLWSS |
| 127 | 1G4 | beta | CDR1 | MNHEY |
| 128 | 1G4 | beta | CDR2 | SVGAGI |
| 129 | 1G4 | beta | CDR3 | CASSYVGNTGELFF |
| 130 | 1G4 | beta | variable domain | MSIGLLCCAALSLLWAGPVNAGVTQ TPKFQVLKTGQSMTLQCAQDMNHE YMSWYRQDPGMGLRLIHYSVGAGI TDQGEVPNGYNVSRSTTEDFPLRLLS AAPSQTSVYFCASSYVGNTGELFFG EGSRLTVL |
| 131 | 1G4 | beta | constant domain | EDLKNVFPPEVAVFEPSEAEISHTQK ATLVCLATGFYPDHVELSWWVNGK EVHSGVSTDPQPLKEQPALNDSRYC LSSRLRVSATFWQNPRNHFRCVQF YGLSENDEWTQDRAKPVTQIVSAEA WGRADCGFTSESYQQGVLSATILYEI LLGKATLYAVLVSALVLMAMVKRK DSRG |
| 132 | 1G4 | beta | full-length | MSIGLLCCAALSLLWAGPVNAGVTQ TPKFQVLKTGQSMTLQCAQDMNHE YMSWYRQDPGMGLRLIHYSVGAGI TDQGEVPNGYNVSRSTTEDFPLRLLS AAPSQTSVYFCASSYVGNTGELFFG EGSRLTVLEDLKNVFPPEVAVFEPSE AEISHTQKATLVCLATGFYPDHVELS WWVNGKEVHSGVSTDPQPLKEQPA LNDSRYCLSSRLRVSATFWQNPRNH FRCVQFYGLSENDEWTQDRAKPV TQIVSAEAWGRADCGFTSESYQQGV LSATILYEILLGKATLYAVLVSALVL MAMVKRKDSRG |

TABLE 2

Peptide sequences of the invention

| Peptide Code | Sequence | SEQ ID NO: |
|---|---|---|
| SPINK2-001 | ALSVLRLAL | 133 |
| SPINK2-001_A2 | AASVLRLAL | 134 |
| SPINK2-001_A3 | ALAVLRLAL | 135 |
| SPINK2-001_A4 | ALSALRLAL | 136 |
| SPINK2-001_A5 | ALSVARLAL | 137 |
| SPINK2-001_A6 | ALSVLALAL | 138 |
| SPINK2-001_A7 | ALSVLRAAL | 139 |
| SPINK2-001_A9 | ALSVLRLAA | 140 |
| SPINK2-001_T1 | TLSVLRLAL | 141 |
| SPINK2-001_T2 | ATSVLRLAL | 142 |
| SPINK2-001_T3 | ALTVLRLAL | 143 |
| SPINK2-001_T4 | ALSTLRLAL | 144 |
| SPINK2-001_T5 | ALSVTRLAL | 145 |
| SPINK2-001_T6 | ALSVLTLAL | 146 |
| SPINK2-001_T7 | ALSVLRTAL | 147 |
| SPINK2-001_T8 | ALSVLRLTL | 148 |

TABLE 2-continued

Peptide sequences of the invention

| Peptide Code | Sequence | SEQ ID NO: |
|---|---|---|
| SPINK2-001_T9 | ALSVLRLAT | 149 |
| CYP-003 | ALMNMKLAL | 150 |
| BAG6-001 | ALSDLRCNL | 151 |
| XRCC5-001 | ALSSLIHAL | 152 |
| TMEM147-001 | ALSTLALYV | 153 |
| SEC-001 | ALSVLADFL | 154 |
| GMPPA-001 | ALYASRLYL | 155 |
| EXOC4-002 | GLSDLRLEL | 156 |
| ARFGAP3-001 | IVSSLRLAY | 157 |
| ANKRD29-002 | YLDVIRLLL | 158 |
| NYESO1-001 | SLLMWITQV | 159 |

EXAMPLES

Ten SPINK2-001-specific TCRs (R39P1C12, R39P1F5, R40P1C2, R41P3E6, R43P3G4, R44P3B3, R44P3E7, R49P2B7, R55P1G7 and R59P2A7, see Table 1), each encoding tumor specific TCR-alpha and TCR-beta chains, were isolated and amplified from T-cells of healthy donors. Cells from healthy donors were in vitro stimulated according to a method previously described (Walter et al., 2003 J Immunol., November 15; 171(10):4974-8) and target-specific cells were single-cell sorted using HLA-A*02 multimers and then used for subsequent TCR isolation. TCR sequences were isolated via 5' RACE by standard methods as described by e.g. Molecular Cloning a laboratory manual fourth edition by Green and Sambrook. The alpha and beta variable regions of TCRs R39P1C12, R39P1F5, R40P1C2, R41P3E6, R43P3G4, R44P3B3, R44P3E7, R49P2B7, R55P1G7 and R59P2A7 were sequenced and expression constructs were generated by gene synthesis for further functional characterization.

R41P3E6, R43P3G4, R55P1G7 and R59P2A7 are derived from HLA-A*02 negative donor (allo-reactive setting) and R39P1C12, R39P1F5, R40P1C2, R44P3B3, R44P3E7 and R49P2B7 are derived from a HLA-A*02 positive donor.

TCRs of interest were expressed in human T cells, e.g. through mRNA electroporation. The T cells were assessed for IFN-γ release after co-culture with different target cells, such as T2 cells loaded with different peptides as well as tumor cell lines. For T-cell activation, data is either shown as absolute IFNγ levels or as background subtracted data, indicated below. Efficacy of CD8+ T cells expressing TCRs R55P1G7 and R44P3B3 was determined e.g. by T cell activation studies (IFNγ release) using different tumor cell lines as target cells.

Background subtraction method for IFNγ release:
Meanbg(TCRoi; co)=[mean(TCRoi; co)−mean(TCRoi; effector only)]−[mean(mock; co)mean(mock; effector only)]
The respective SDbg was calculated:
SDbg(TCRoi; co)=[SD(TCRoi; co)$^2$+SD(TCRoi; effector only)$^2$+SD(mock;co)$^2$+SD(mock; effector only)$^2$]$^{[1/2]}$
TCRoi=effector cells expressing TCR of interest
Mock=effector cells without exogenous TCR expression
Co=effector cells co-cultured with target cells
Effector only=effector cells not co-cultured
Mean(bg)=mean IFNγ release (background subtracted)
SD(bg)=standard deviation (background subtracted)
BLI (Biolayer interferometry) binding analysis for SPINK2-001 TCRs, expressed as soluble TCRs according to a previously described method (Willcox B E et al., 1999 Protein Sci., November; 8(11):2418-23), and HLA-A*02/SPINK2-001 complex was used for affinity determination. BLI binding data for 1G4 TCR and HLA-A*02/NYESO1-001 are used as control.

Example 1: T-Cell Receptor R39P1C12

TCR R39P1C12 (SEQ ID NOs: 1-12) is restricted towards HLA-A*02-presented SPINK2-001 (SEQ ID NO: 133) (see FIG. 11).

R39P1C12 specifically recognizes SPINK2-001 as human primary CD8+ T-cells re-expressing this TCR release IFNγ upon co-incubation with HLA-A*02+ target cells, loaded either with SPINK2-001 peptide or alanine or threonine substitution variants of SPINK2-001 (FIG. 1) or different peptides showing high degree of sequence similarity to SPINK2-001 (FIG. 11). NYESO1-001 peptide is used as negative control. TCR R39P1C12 has an EC$_{50}$ of 0.81 nM (FIG. 21) and an affinity of 18 μM (R$^2$=0.9956) (FIG. 33).

Example 2: T-Cell Receptor R39P1F5

TCR R39P1F5 (SEQ ID NOs: 13-24) is restricted towards HLA-A*02-presented SPINK2-001 (SEQ ID NO: 133) (see FIG. 12).

R39P1F5 specifically recognizes SPINK2-001 as human primary CD8+ T-cells re-expressing this TCR release IFNγ upon co-incubation with HLA-A*02+ target cells, loaded either with SPINK2-001 peptide or alanine or threonine substitution variants of SPINK2-001 (FIG. 2) or different peptides showing high degree of sequence similarity to SPINK2-001 (FIG. 12). NYESO1-001 peptide is used as negative control. TCR R39P1F5 has an EC$_{50}$ of 1.52 nM (FIG. 22) and an affinity of 34 μM (R$^2$=0.9962) (FIG. 33).

Example 3: T-Cell Receptor R40P1C2

TCR R40P1C2 (SEQ ID NOs: 25-36) is restricted towards HLA-A*02-presented SPINK2-001 (SEQ ID NO: 133) (see FIG. 13).

R40P1C2 specifically recognizes SPINK2-001 as human primary CD8+ T-cells re-expressing this TCR release IFNγ upon co-incubation with HLA-A*02+ target cells, loaded either with SPINK2-001 peptide or alanine or threonine substitution variants of SPINK2-001 (FIG. 3) or different peptides showing high degree of sequence similarity to SPINK2-001 (FIG. 13). NYESO1-001 peptide is used as negative control. TCR R40P1C2 has an EC$_{50}$ of 1.94 nM (FIG. 23).

Example 4: T-Cell Receptor R41P3E6

TCR R41P3E6 (SEQ ID NOs: 37-48) is restricted towards HLA-A*02-presented SPINK2-001 (SEQ ID NO: 133) (see FIG. 14).

R41P3E6 specifically recognizes SPINK2-001 as human primary CD8+ T-cells re-expressing this TCR release IFNγ upon co-incubation with HLA-A*02+ target cells and bind HLA-A*02 tetramers (FIG. 31), respectively, loaded either with SPINK2-001 peptide or alanine or threonine substitution variants of SPINK2-001 (FIG. 4) or different peptides showing high degree of sequence similarity to SPINK2-001 (FIG. 14). NYESO1-001 peptide is used as negative control. TCR R41P3E6 has an $EC_{50}$ of 1.03 nM (FIG. 24) and an affinity of 13 μM ($R^2$=0.9892) (FIG. 33).

Example 5: T-Cell Receptor R43P3G4

TCR R43P3G4 (SEQ ID NOs: 49-60) is restricted towards HLA-A*02-presented SPINK2-001 (SEQ ID NO: 133) (see FIG. 15).

R43P3G4 specifically recognizes SPINK2-001 as human primary CD8+ T-cells re-expressing this TCR release IFNγ upon co-incubation with HLA-A*02+ target cells, loaded either with SPINK2-001 peptide or alanine or threonine substitution variants of SPINK2-001 (FIG. 5) or different peptides showing high degree of sequence similarity to SPINK2-001 (FIG. 15).

NYESO1-001 peptide is used as negative control. TCR R43P3G4 has an $EC_{50}$ of 1.34 nM (FIG. 25).

Example 6: T-Cell Receptor R44P3B3

TCR R44P3B3 (SEQ ID NOs: 61-72) is restricted towards HLA-A*02-presented SPINK2-001 (SEQ ID NO: 133) (see FIG. 16).

R44P3B3 specifically recognizes SPINK2-001 as human primary CD8+ T-cells re-expressing this TCR release IFNγ upon co-incubation with HLA-A*02+ target cells and bind HLA-A*02 tetramers (FIG. 31), respectively, loaded either with SPINK2-001 peptide or alanine or threonine substitution variants of SPINK2-001 (FIG. 6) or different peptides showing high degree of sequence similarity to SPINK2-001 (FIG. 16). NYESO1-001 peptide is used as negative control. TCR R44P3B3 has an $EC_{50}$ of 1.06 nM (FIG. 26) and an affinity of 37 μM ($R^2$=0.9947) (FIG. 33).

For CD8+ T cells expressing TCR R44P3B3, an activity towards the SPINK2-001-overexpressing A375 tumor cells was observed (FIG. 32), but not towards the wildtype A375 tumor cell line. A375 cells endogenously express HLA-A2.

T-cell activation upon co-culture with cell lines expressing HLA-A*02 and SPINK2-001 reflects the recognition of endogenously presented target pHLA (peptide presented on human leukocyte antigen) by TCR R44P3B3.

Example 7: T-Cell Receptor R44P3E7

TCR R44P3E7 (SEQ ID NOs: 73-84) is restricted towards HLA-A*02-presented SPINK2-001 (SEQ ID NO: 133) (see FIG. 17).

Figure 27:
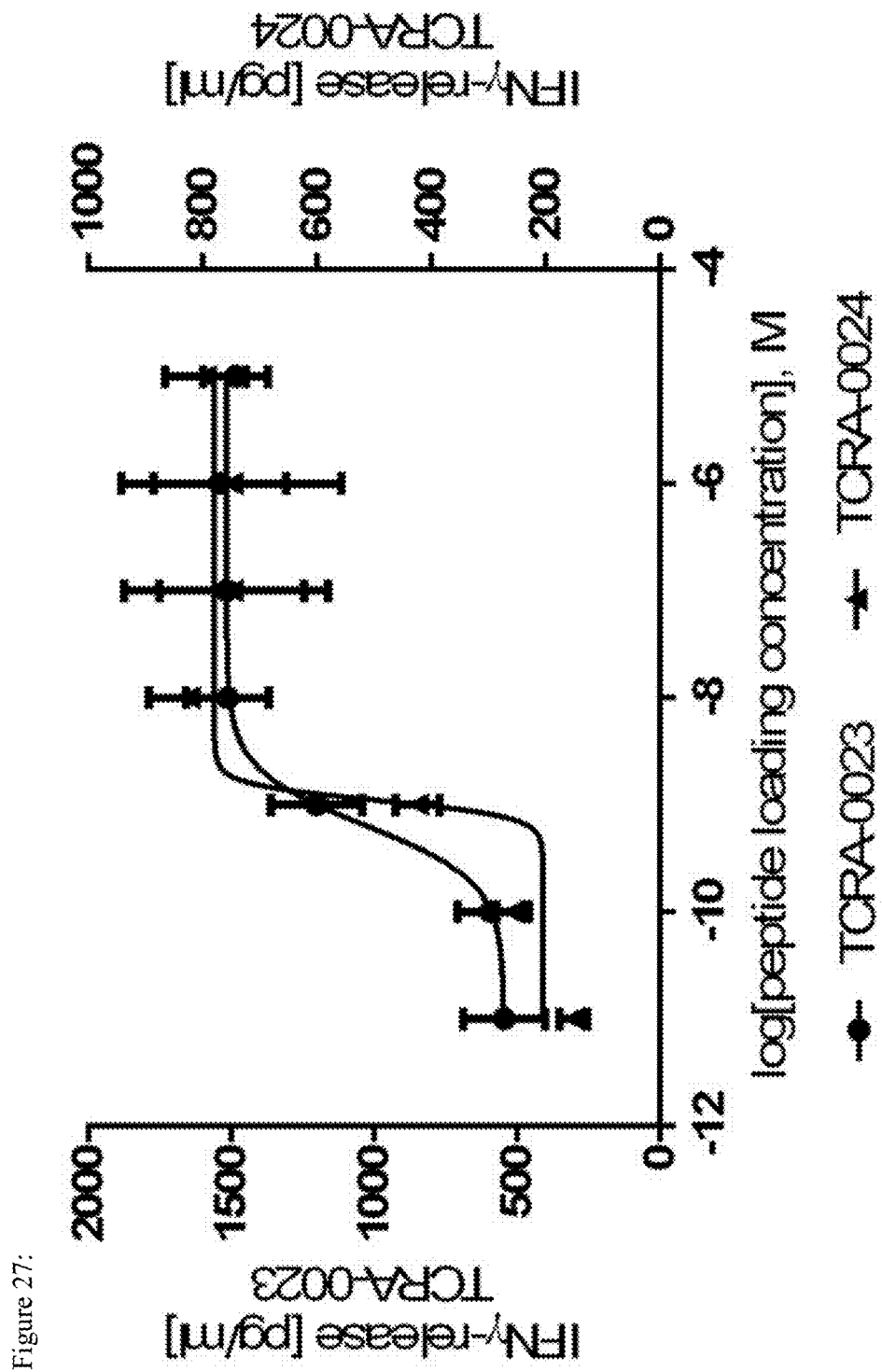

R44P3E7 specifically recognizes SPINK2-001 as human primary CD8+ T-cells re-expressing this TCR release IFNγ upon co-incubation with HLA-A*02+ target cells, loaded either with SPINK2-001 peptide or alanine or threonine substitution variants of SPINK2-001 (FIG. 7) or different peptides showing high degree of sequence similarity to SPINK2-001 (FIG. 17). NYESO1-001 peptide is used as negative control. TCR R44P3E7 has an $EC_{50}$ of 0.86 nM (FIG. 27).

Example 8: T-Cell Receptor R49P2A7

TCR R49P2A7 (SEQ ID NOs: 85-96) is restricted towards HLA-A*02-presented SPINK2-001 (SEQ ID NO: 133) (see FIG. 18).

R49P2A7 specifically recognizes SPINK2-001 as human primary CD8+ T-cells re-expressing this TCR release IFNγ upon co-incubation with HLA-A*02+ target cells and bind HLA-A*02 tetramers (FIG. 31), respectively, loaded either with SPINK2-001 peptide or alanine or threonine substitution variants of SPINK2-001 (FIG. 8) or different peptides showing high degree of sequence similarity to SPINK2-001 (FIG. 18). NYESO1-001 peptide is used as negative control. TCR R49P2A7 has an $EC_{50}$ of >83.24 nM (FIG. 28).

Example 9: T-Cell Receptor R55P1G7

TCR R55P1G7 (SEQ ID NOs: 97-108) is restricted towards HLA-A*02-presented SPINK2-001 (SEQ ID NO: 133) (see FIG. 19).

R55P1G7 specifically recognizes SPINK2-001 as human primary CD8+ T-cells re-expressing this TCR release IFNγ upon co-incubation with HLA-A*02+ target cells and bind HLA-A*02 tetramers (FIG. 31), respectively, loaded either with SPINK2-001 peptide or alanine or threonine substitution variants of SPINK2-001 (FIG. 9) or different peptides showing high degree of sequence similarity to SPINK2-001 (FIG. 19). NYESO1-001 peptide is used as negative control. TCR R55P1G7 has an $EC_{50}$ of 91.5 pM (FIG. 29) and an affinity of 4.3 μM ($R^2$=0.9765) (FIG. 33).

For CD8+ T cells expressing TCR R55P1G7, an activity towards the SPINK2-001-overexpressing A375 tumor cells was observed (FIG. 32), but not towards the wildtype A375 tumor cell line. The A375 cells endogenously express HLA-A2.

T-cell activation upon co-culture with cell lines expressing HLA-A*02 and SPINK2-001 reflects the recognition of endogenously presented target pHLA (peptide presented on human leukocyte antigen) by TCR R55P1G7.

Example 10: T-Cell Receptor R59P2A7

TCR R59P2A7 (SEQ ID NOs: 109-120) is restricted towards HLA-A*02-presented SPINK2-001 (SEQ ID NO: 133) (see FIG. 20).

R59P2A7 specifically recognizes SPINK2-001 as human primary CD8+ T-cells re-expressing this TCR release IFNγ upon co-incubation with HLA-A*02+ target cells, loaded either with SPINK2-001 peptide or alanine or threonine substitution variants of SPINK2-001 (FIG. 10) or different peptides showing high degree of sequence similarity to SPINK2-001 (FIG. 20). NYESO1-001 peptide is used as negative control. TCR R59P2A7 has an $EC_{50}$ of 0.86 nM (FIG. 30).

The invention claimed is:

1. A method of treating an HLA-A*02-positive patient who has acute myeloid leukemia, comprising administering to the patient a population of transformed CD8+cells expressing at least one vector encoding a T cell receptor (TCR),
 wherein the TCR comprises SEQ ID NO: 1, SEQ ID NO: 2, SEQ ID NO: 3, SEQ ID NO: 7, SEQ ID NO: 8, and SEQ ID NO: 9,
 wherein the TCR is capable of binding to a peptide consisting of the amino acid sequence of ALSVLRLAL (SEQ ID NO: 133) in a complex with an MHC class I molecule.

2. The method of claim 1, wherein the population of transformed cells are produced by a method comprising
 isolating a cell from a subject,
 transforming the cell with at least one vector encoding the TCR to produce a transformed cell, and
 expanding the transformed cell to produce the population of transformed cells.

3. The method of claim 2, wherein the subject is the patient.

4. The method of claim 2, wherein the subject is a healthy donor.

5. The method of claim 1, wherein the TCR comprises an α chain comprising the amino acid sequence of SEQ ID NO: 6 and a β chain comprising the amino acid sequence of SEQ ID NO: 12.

6. The method of claim 1, wherein the population of transformed cells are administered in the form of a pharmaceutical composition.

7. The method of claim 6, wherein the pharmaceutical composition comprises a chemotherapeutic agent selected from the group consisting of asparaginase, busulfan, carboplatin, cisplatin, daunorubicin, doxorubicin, fluorouracil, gemcitabine, hydroxyurea, methotrexate, paclitaxel, rituximab, vinblastine, and vincristine.

8. The method of claim 1, wherein the TCR comprises:
 a CDR1α chain comprising the amino acid sequence of SEQ ID NO: 1,
 a CDR2α chain comprising the amino acid sequence of SEQ ID NO: 2,
 a CDR3α chain comprising the amino acid sequence of SEQ ID NO: 3,
 a CDR1β chain comprising the amino acid sequences of SEQ ID NO: 7,
 a CDR2β chain comprising the amino acid sequence of SEQ ID NO: 8, and
 a CDR3β chain comprising the amino acid sequence of SEQ ID NO: 9.

9. The method of claim 1, wherein the TCR comprises
 a CDR1α chain consisting of the amino acid sequence of SEQ ID NO: 1,
 a CDR2α chain comprising the amino acid sequence of SEQ ID NO: 2,
 a CDR3α chain consisting of the amino acid sequence of SEQ ID NO: 3,
 a CDR1β chain consisting of the amino acid sequence of SEQ ID NO: 7,
 a CDR2β chain comprising the amino acid sequence of SEQ ID NO: 8, and
 a CDR3β chain consisting of the amino acid sequence of SEQ ID NO: 9.

10. The method of claim 1, wherein the TCR comprises
 a CDR1α chain comprising the amino acid sequence of SEQ ID NO: 1,
 a CDR2α chain comprising the amino acid sequence of SEQ ID NO: 2,
 a CDR3α chain consisting of the amino acid sequence of SEQ ID NO: 3,
 a CDR1β chain comprising the amino acid sequence of SEQ ID NO: 7,
 a CDR2β chain comprising the amino acid sequence of SEQ ID NO: 8, and
 a CDR3β chain consisting of the amino acid sequence of SEQ ID NO: 9.

11. The method of claim 1, wherein the TCR comprises
 a CDR1α chain comprising the amino acid sequence of SEQ ID NO: 1,
 a CDR2α chain comprising the amino acid sequence of SEQ ID NO: 2,
 a CDR3α chain comprising the amino acid sequence of SEQ ID NO: 3,
 a CDR1β chain comprising the amino acid sequence of SEQ ID NO: 7,
 a CDR2β chain consisting of the amino acid sequence of SEQ ID NO: 8, and
 a CDR3β chain comprising the amino acid sequence of SEQ ID NO: 9.

12. The method of claim 1, wherein the TCR comprises
 a CDR1α chain consisting of the amino acid sequence of SEQ ID NO: 1, a CDR2α chain comprising the amino acid sequence of SEQ ID NO: 2,
a CDR3α chain comprising the amino acid sequence of SEQ ID NO: 3,
a CDR1β chain consisting of the amino acid sequence of SEQ ID NO: 7,
a CDR2β chain comprising the amino acid sequence of SEQ ID NO: 8, and
a CDR3β chain comprising the amino acid sequence of SEQ ID NO: 9.

13. The method of claim 1, wherein the TCR comprises
a CDR1α chain consisting of the amino acid sequence of SEQ ID NO: 1,
a CDR2α chain consisting of the amino acid sequence of SEQ ID NO: 2,
a CDR3α chain consisting of the amino acid sequence of SEQ ID NO: 3,
a CDR1β chain consisting of the amino acid sequence of SEQ ID NO: 7,
a CDR2β chain consisting of the amino acid sequence of SEQ ID NO: 8, and
a CDR3β chain consisting of the amino acid sequence of SEQ ID NO: 9.

14. The method of claim 1, wherein the TCR comprises an α chain variable region having 80% sequence identity to the amino acid sequence of SEQ ID NO: 4 and a β chain variable region having 80% sequence identity to the amino acid sequence SEQ ID NO: 10.

15. The method of claim 1, wherein the TCR comprises an α chain variable region having 95% sequence identity to the amino acid sequence of SEQ ID NO: 4 and a β chain variable region having 95% sequence identity to the amino acid sequence SEQ ID NO: 10.

16. The method of claim 14, wherein in α chain variable region or the β chain variable region comprises an amino acid at position 44 according to the IMGT numbering substituted with another suitable amino acid thereby improving stability and/or pairing of said chains.

17. The method of claim 1, wherein the TCR comprises an α chain constant region having 80% sequence identity to the amino acid sequence of SEQ ID NO: 5 and a β chain constant region having 80% sequence identity to the amino acid sequence SEQ ID NO: 11.

18. The method of claim 1, wherein the TCR comprises an α chain constant region having 95% sequence identity to the amino acid sequence of SEQ ID NO: 5 and a β chain constant region having 95% sequence identity to the amino acid sequence SEQ ID NO: 11.

19. The method of claim 1, wherein the TCR comprises an α chain having at least 80% sequence identity to the amino acid sequence of SEQ ID NO: 6 and a β chain having at least 80% sequence identity to the amino acid sequence SEQ ID NO: 12.

20. The method of claim 1, wherein the TCR comprises an α chain having at least 95% sequence identity to the amino acid sequence of SEQ ID NO: 6 and a β chain having at least 95% sequence identity to the amino acid sequence SEQ ID NO: 12.

* * * * *